US008202704B2

(12) United States Patent
Foreman et al.

(10) Patent No.: US 8,202,704 B2
(45) Date of Patent: Jun. 19, 2012

(54) TRICHODERMA GENES

(75) Inventors: Pamela Foreman, Los Altos, CA (US);
Frits Goedegebuur, Vlaardingen (NL);
Pieter Van Solingen, Naaldwijk (NL);
Michael Ward, San Francisco, CA (US)

(73) Assignee: Danisco US Inc., Palo Alto, CA (US)

(*) Notice: Subject to any disclaimer, the term of this patent is extended or adjusted under 35 U.S.C. 154(b) by 0 days.

(21) Appl. No.: 13/029,919

(22) Filed: Feb. 17, 2011

(65) Prior Publication Data

US 2011/0287511 A1 Nov. 24, 2011

Related U.S. Application Data

(62) Division of application No. 12/683,108, filed on Jan. 6, 2010, now Pat. No. 7,923,235, which is a division of application No. 10/555,358, filed as application No. PCT/US2004/016881 on May 28, 2004, now Pat. No. 7,666,648.

(60) Provisional application No. 60/474,411, filed on May 29, 2003, provisional application No. 60/475,826, filed on Jun. 3, 2003.

(51) Int. Cl.
*C12P 21/06* (2006.01)
*C12N 9/00* (2006.01)
*C12N 9/24* (2006.01)
*C12N 1/20* (2006.01)
*C12N 15/00* (2006.01)

(52) U.S. Cl. .... 435/69.1; 435/183; 435/200; 435/252.3; 435/320.1; 536/23.2

(58) Field of Classification Search .......................... None
See application file for complete search history.

(56) References Cited

U.S. PATENT DOCUMENTS

| 4,797,361 A | 1/1989 | Montenecourt |
| 5,246,853 A | 9/1993 | Clarkson et al. |
| 5,475,101 A | 12/1995 | Ward et al. |
| 5,650,322 A | 7/1997 | Clarkson et al. |
| 5,874,276 A | 2/1999 | Fowler et al. |
| 6,268,328 B1 | 7/2001 | Mitchinson et al. |
| 6,286,196 B1 | 9/2001 | Vogel |
| 6,408,208 B1 | 6/2002 | Sun |
| 6,486,112 B1 | 11/2002 | Bettiol et al. |
| 7,666,648 B2 | 2/2010 | Foreman et al. |
| 7,923,235 B2 | 4/2011 | Foreman et al. |

FOREIGN PATENT DOCUMENTS

| EP | 0 507 369 | 10/1992 |
| WO | WO 92/06209 A | 4/1992 |
| WO | WO 94/28117 A | 12/1994 |
| WO | WO 95/16782 A | 6/1995 |
| WO | WO 96/06935 A | 3/1996 |
| WO | WO 97/13853 A | 4/1997 |
| WO | WO 98/31821 A | 7/1998 |
| WO | WO 01/46357 A | 6/2001 |
| WO | WO 03/031477 A | 4/2003 |
| WO | WO 2005/030998 A | 4/2005 |

OTHER PUBLICATIONS

Altschul, S.F. et al. "Basic local alignment search tool." *J. Mol. Biol* 215(3):403-410, 1990.
Altschul, S.F. et al. "Gapped BLAST and PSI-BLAST: a new generation of protein database search programs." *Nucleic Acids Res.* 25(27):3389-3402, 1997.
Aro, N. et al. "ACEII, a Novel Transcriptional Activator Involved in Regulation of Cellulase and Xylanase Genes of *Trichoderma reesei*." *Journal of Biological Chemistry* 276(26):24309-24314, 2001.
Bergès, T. et al. "Isolation of uridine auxotrophs from *Trichoderma reesei* and efficient transformation with the cloned ura3 and ura5 genes." *Current Genetics* 19(5):359-365, 1991.
Bhikhabhai, R. et al. "Isolation of cellulolytic enzymes from *Trichoderma reesei* QM 9414." *J. Appl. Biochem.* 6(5-6):336-45, 1984.
Biely, P. et al. "Acetyl xylan esterases in fungal cellulolytic systems." *FEBS Letters* 186(1):80-84, 1985.
Birch, P.R.J. "Targeted differential display of abundantly expressed sequences from the basidiomycete *Phanerochaete chrysosporium* which contain regions coding for fungal cellulose-binding domains." *Current Genetics* 33(1):70-76, 1998.
Brosius, J. "Superpolylinkers in cloning and expression vectors." *DNA* 8(10):759-777, 1989.
Brumbauer, A. et al. "Fractionation of cellulase and β-glucosidase in a *Trichoderma reesei* culture liquid by use of two-phase partitioning." *Bioseparation* 7(6):287-295, 1999.
Campbell, E.I. et al. "Improved transformation efficiency of *Aspergillus niger* using the homologous No. gene for nitrate reductase." *Current Genetics* 16(1):53-56, 1989.
Chen, C.M. et al. "Nucleotide Sequence and Deduced Primary Structure of Cellobiohydrolase II from *Trichoderma reesei*." *Nat Biotech* 5(3):274-278, 1987.
Chica, R.A. et al. "Semi-rational approaches to engineering enzyme activity: combining the benefits of directed evolution and rational design." *Current Opinion in Biotechnology* 16(4):378-384, 2005.
Database EMBL. "*Aspergillus sojae* arf mRNA for α-L-arabinofuranosidase, complete cds." Accession No. AB033289, 1999.
Database EMBL. "TrEST-A4294 TrEST-A *Hypocrea jecorina* cDNA clone Tr-A4294 5' similar to hypothetical protein [Neurospora crassa], mRNA sequence." Accession No. BM077051, 2002.
Database EMBL. "tric010xi01 *T.reesei* mycelial culture, Version 3 april *Hypocrea jecorina* cDNA clone tric010xi01, mRNA sequence." Accession No. CB897267, 2003.
Database EMBL. "tric018xa22 *T.reesei* mycelial culture, Version 3 april *Hypocrea jecorina* cDNA clone tric018xa22, mRNA sequence." Accession No. CB899258, 2003.

(Continued)

*Primary Examiner* — Christian Fronda
(74) *Attorney, Agent, or Firm* — Danisco US Inc.

(57) ABSTRACT

Described herein are novel gene sequences isolated from *Trichoderma reesei*. Two genes encoding proteins comprising a cellulose binding domain, one encoding an arabionfuranosidase and one encoding an acetylxylanesterase are described. The sequences, CIP1 and CIP2, contain a cellulose binding domain. These proteins are especially useful in the textile and detergent industry and in pulp and paper industry.

17 Claims, 22 Drawing Sheets

OTHER PUBLICATIONS

Database EMBL. "tric028xe15 *T.reesei* mycelial culture, Version 3 april *Hypocrea jecorina* cDNA clone tric028xe15, mRNA sequence." Accession No. CB901909, 2003.

Database EMBL. "tric029xo22 *T.reesei* mycelial culture, Version 3 april *Hypocrea jecorina* cDNA clone tric029xo22, mRNA sequence." Accession No. CB902338, 2003.

Database EMBL. "tric030xn12 *T.reesei* mycelial culture, Version 3 april *Hypocrea jecorina* cDNA clone tric030xn12, mRNA sequence." Accession No. CB902576, 2003.

Database EMBL. "tric034xk04 *T.reesei* mycelial culture, Version 3 april *Hypocrea jecorina* cDNA clone tric034xk04, mRNA sequence." Accession No. C8903438, 2003.

Database EMBL. "tric035xa22 *T.reesei* mycelial culture, Version 3 april *Hypocrea jecorina* cDNA clone tric035xa22, mRNA sequence." Accession No. C8903527, 2003.

Database EMBL. "tric038xl21 *T.reesei* mycelial culture, Version 3 april *Hypocrea jecorina* cDNA clone tric038xl21, mRNA sequence." Accession No. C8904545, 2003.

Database EMBL. "tric040xk24 *T.reesei* mycelial culture, Version 3 april *Hypocrea jecorina* cDNA clone tric040xk24, mRNA sequence." Accession No. C8904950, 2003.

Database EMBL. "tric080xd15 *T.reesei* mycelial culture, Version 3 april *Hypocrea jecorina* cDNA clone tric080xd15, mRNA sequence." Accession No. C8906767, 2003.

Database EMBL. "tric082xo13 *T.reesei* mycelial culture, Version 3 april *Hypocrea jecorina* cDNA clone tric082xo13, mRNA sequence." Accession No. C8907643, 2003.

Database GenPept. "Alpha-N-arabinofuranosidase (EC 3.2.1.55), STX-IV-Streptomyces thermoviolaceus." Accession No. JC7820, 2002.

Database Genseq. "*Trichoderma reesei* EST SEQ ID No. 7425." Accession No. AAF14902, 2001.

Database UniProt. "Putative secreted hydrolase." Accession No. 069962, 1998.

Database UniProt. "Cip1." Accession No. Q7Z9M9, 2003.

Davies, G. et al. "Structures and mechanisms of glycosyl hydrolases." *Structure* 3(9):853-859, 1995.

Derisi, J. et al. "Use of a cDNA microarray to analyse gene expression patterns in human cancer." *Nature Genetics* 14(4):457-460, 1996.

Deutscher, M.P. "Rethinking your purification procedure." in *Guide to Protein Purification*, Methods in Enzymology, No. 182, ed. M.P. Deutscher, New York, NY, Academic Press, pp. 779-780, 1990.

Ellouz, S. et al. "Analytical separation of *Trichoderma reesei* cellulases by ion-exchange fast protein liquid chromatography." *J. Chromatography* 396:307-317, 1987.

Fliess, A. et al. "Characterization of cellulases by HPLC separation." *Eur. J. Appl. Microbiol. Biotechnol.* 17(5):314-318, 1983.

Foreman, P.K. et al. "Transcriptional Regulation of Biomass-degrading Enzymes in the Filamentous Fungus *Trichoderma reesei*." *J. Biol. Chem.* 278(34):31988-31997, 2003.

Goedegebuur, F. et al. "Cloning and relational analysis of 15 novel fungal endoglucanases from family 12 glycosyl hydrolase." *Current Genetics* 41(2):89-98, 2002.

Goyal, A. et al. "Characteristics of fungal cellulases." *Biores. Technol* 36:37-50, 1991.

Gutiérrez, R. et al. "Acetyl xylan esterase II from *Penicillium purpurogenum* is similar to an esterase from *Trichoderma reesei* but lacks a cellulose binding domain." *FEBS Letters* 423(1):35-38, 1998.

Hari Krishna, S. et al. "Simultaneous saccharification and fermentation of lignocellulosic wastes to ethanol using a thermotolerant yeast." *Bioresource Technology* 77(2):193-196, 2001.

Van Hartingsveldt, W. et al. "Development of a homologous transformation system for *Aspergillus niger* based on the *pyrG* gene." *Molecular and General Genetics* 206(1):71-75, 1987.

Hartley, J.L. et al. "DNA cloning using in vitro site-specific recombination." *Genome Research* 10(11):1788-1795, 2000.

Henrissat, B. "A classification of glycosyl hydrolases based on amino acid sequence similarities." *Biochemical Journal* 280:309-316, 1991.

Henrissat, B. et al. "New families in the classification of glycosyl hydrolases based on amino acid sequence similarities." *Biochemical J.* 293:781-788, 1993.

Henrissat, B. et al. "Updating the sequence-based classification of glycosyl hydrolases.." *Biochemical Journal* 316:695-696, 1996.

Hu, Q.J. et al. "Antibodies specific for the human retinoblastoma protein identify a family of related polypeptides." *Mol. Cell. Biol.* 11(11):5792-5799, 1991.

Hughes, T.R. et al. "Expression profiling using microarrays fabricated by an ink-jet oligonucleotide synthesizer." *Nature Biotechnology* 19(4):342-347, 2001.

Ilmen, M. et al. "Regulation of cellulase gene expression in the filamentous fungus *Trichoderma reesei*." *Appl. Environ. Microbiol.* 63(4):1298-1306, 1997.

Li, X.-L. et al. "Identification of genes encoding microbial glucuronoyl esterases." *FEBS Letters* 581(21):4029-4035, 2007.

Margolles-Clark, E. et al. "Cloning of genes encoding α-L-arabinofuranosidase and β-xylosidase from *Trichoderma reesei* by expression in *Saccharomyces cerevisiae*." *Appl. Environ. Microbiol.* 62(10):3840-3846, 1996.

Margolles-Clark, E. et al. "Acetyl xylan esterase from *Trichoderma reesei* contains an active-site serine residue and a cellulose-binding domain." *Eur. J. Biochem. / FEBS* 237(3):553-560, 1996.

Medve, J. et al. "Ion-exchange chromatographic purification and quantitative analysis of *Trichoderma reesei* cellulases cellobiohydrolase I, II and endoglucanase II by fast protein liquid chromatography." *J. Chromat. A*, 808(1-2):153-165, 1998.

Nogawa, M. et al. "An α-L-Arabinofuranosidase from *Trichoderma reesei* Containing a Noncatalytic Xylan-Binding Domain." *Appl. Environ. Microbiol.* 65(9):3964-3968, 1999.

Ohmiya, K. et al. "Structure of cellulases and their applications." *Biotechnol. Genet. Eng. Rev.*, 14:365-414, 1997.

Ouyang, J. et al. "A complete protein pattern of cellulase and hemicellulase genes in the filamentous fungus *Trichoderma reesei*." *Biotechnology Journal* 1(11):1266-1274, 2006.

Penttilä, M. et al. "Homology between cellulase genes of *Trichoderma reesei*: complete nucleotide sequence of the endoglucanase I gene." *Gene* 45(3):253-63, 1986.

Pourquié, J. et al. "Scale up of cellulase production and utilization." in *Biochemistry and Genetics of Cellulose Degradation*, eds. J.P. Aubert et al. London: Academic Press, pp. 71-86, 1988.

Poutanen, K. et al. "Deacetylation of xylans by acetyl esterases of *Trichoderma reesei*." *Applied Microbiology and Biotechnology* 33(5):506-510, 1990.

Saha, B.C. "α-L-Arabinofuranosidases: biochemistry, molecular biology and application in biotechnology." *Biotechnology Advances* 18(5):403-423, 2000.

Saloheimo, M. et al. "EGIII, a new endoglucanase from *Trichoderma reesei*: the characterization of both gene and enzyme." *Gene* 63(1):11-22, 1988.

Scopes, R.K. et al. "Purification of all glycolytic enzymes from one muscle extract." in *Carbohydrate Metabolism—Part E*, Methods in Enzymology, No. 90, ed. W.A. Wood. New York: Academic Press, pp. 479-490, 1982.

Sen, S. et al. "Developments in Directed Evolution for Improving Enzyme Functions." *Applied Biochemistry and Biotechnology* 143(3):212-223, 2007.

Sheir-Neiss, G. et al. "Characterization of the secreted cellulases of *Trichoderma reesei* wild type and mutants during controlled fermentations." *Applied Microbiology and Biotechnology* 20(1):46-53, 1984.

Shoemaker, S. et al. "Molecular Cloning of Exo-Cellobiohydrolase I Derived from *Trichoderma reesei* Strain L27." *Nat Biotech* 1(8):691-696, 1983.

Smith, J.L. et al. "Sequence of the cloned *pyr4* gene of *Trichoderma reesei* and its use as a homologous selectable marker for transformation." *Current Genetics* 19(1):27-33, 1991.

Sundberg, M. et al. "Purification and properties of two acetylxylan esterases of *Trichoderma reesei*." *Biotechnol. Appl. Biochem.* 13(1):1-11, 1991.

Te'o, V.S.J. et al. "Codon optimization of xylanase gene *xynB* from the thermophilic bacterium *Dictyoglomus thermophilum* for expression in the filamentous fungus *Trichoderma reesei*." *FEMS Microbiology Letters* 190(1):13-19, 2000.

Tomaz, C.T. et al. "Studies on the chromatographic fractionation of *Trichoderma reesei* cellulases by hydrophobic interaction." *J. Chromat. A*, 865(1-2):123-128, 1999.

Tsujibo, H. et al. "Molecular cloning of the gene encoding a novel β-N-acetylhexosaminidase from a marine bacterium, *Alteromonas* sp. strain O-7, and characterization of the cloned enzyme." *Bioscience, Biotech. Biochem.* 66(2):471-475, 2002.

Udenfriend, S. et al. "Prediction of ω-site in nascent precursor of glycosylphosphatidylinositol protein." in *Lipid Modifications of Proteins*, Methods in Enzymology, No. 250, eds. P.J. Casey et al., New York: Academic Press, pp. 571-582, 1995.

Van Arsdell, J.N. et al. "Cloning, Characterization, and Expression in *Saccharomyces cerevisiae* of Endoglucanase I from *Trichoderma reesei*." *Nat Biotech* 5(1):60-64, 1987.

Van Den Hondel, C. et al. "Heterologous gene expression in filamentous fungi." in *More Gene Manipulations in Fungi*, eds. J.W. Bennett et al., San Diego, CA: Academic Press, pp. 396-428, 1991.

Van Tilbeurgh, H. et al. "Separation of endo- and exo-type cellulases using a new affinity chromatography method." *FEBS Letters* 169(2):215-218, 1984.

Ward, M. et al. "Use of *Aspergillus* overproducing mutants, cured for integrated plasmid, to overproduce heterologous proteins." *Appl. Microbiol. and Biotech.* 39(6):738-743, 1993.

Whisstock et al., "Prediction of Protein Function From Protein Sequence and Structure," Quarterly Reviews of Biophysics 36:3 (2003) pp. 307-340.

Wilson, E.M. et al. "Expression vector pT7: TKII for the synthesis of authentic biologically active RNA encoding vaccinia virus thymidine kinase." *Gene* 77(1):69-78, 1989.

International Preliminary Report on Patentability and Written Opinion of the International Searching Authority of International Application No. PCT/US2004/016881 dated Aug. 22, 2006.

Figure 1
cip1 cDNA sequence (SEQ ID NO: 1)

```
GACTAGTTCA TAATACAGTA GTTGAGTTCA TAGCAACTTC ACTCTCTAGC      50
TGAACAAATT ATCTGCGCAA ACATGGTTCG CCGGACTGCT CTGCTGGCCC     100
TTGGGGCTCT CTCAACGCTC TCTATGGCCC AAATCTCAGA CGACTTCGAG     150
TCGGGCTGGG ATCAGACTAA ATGGCCCATT TCGGCACCAG ACTGTAACCA     200
GGGCGGCACC GTCAGCCTCG ACACCACAGT AGCCCACAGC GGCAGCAACT     250
CCATGAAGGT CGTTGGTGGC CCCAATGGCT ACTGTGGACA CATCTTCTTC     300
GGCACTACCC AGGTGCCAAC TGGGGATGTA TATGTCAGAG CTTGGATTCG     350
GCTTCAGACT GCTCTCGGCA GCAACCACGT CACATTCATC ATCATGCCAG     400
ACACCGCTCA GGGAGGGAAG CACCTCCGAA TTGGTGGCCA AAGCCAAGTT     450
CTCGACTACA ACCGCGAGTC CGACGATGCC ACTCTTCCGG ACCTGTCTCC     500
CAACGGCATT GCCTCCACCG TCACTCTGCC TACCGGCGCG TTCCAGTGCT     550
TCGAGTACCA CCTGGGCACT GACGGAACCA TCGAGACGTG GCTCAACGGC     600
AGCCTCATCC CGGGCATGAC CGTGGGCCCT GGCGTCGACA ATCCAAACGA     650
CGCTGGCTGG ACGAGGGCCA GCTATATTCC GGAGATCACC GGTGTCAACT     700
TTGGCTGGGA GGCCTACAGC GGAGACGTCA ACACCGTCTG GTTCGACGAC     750
ATCTCGATTG CGTCGACCCG CGTGGGATGC GGCCCCGGCA GCCCCGGCGG     800
TCCTGGAAGC TCGACGACTG GGCGTAGCAG CACCTCGGGC CCGACGAGCA     850
CTTCGAGGCC AAGCACCACC ATTCCGCCAC CGACTTCCAG GACAACGACC     900
GCCACGGGTC CGACTCAGAC ACACTATGGC CAGTGCGGAG GGATTGGTTA    1000
CAGCGGGCCT ACGGTCTGCG CGAGCGGCAC GACCTGCCAG GTCCTGAACC    1050
CATACTACTC CCAGTGCTTA TAAGGGGATG AGCATGGAGT GAAGTGAAGT    1100
GAAGTGGAGA GAGTTGAAGT GGCATTGCGC TGGGCTGGGT AGATAAAAGT    1150
CAGCAGCTAT GAATACTCTA TGTGATGCTC ATTGGCGTGT ACGTTTTAAA    1200
AAAAAAAAAA AAAAAAAAAA AAAAAAAAAA AAAAAAAAAA AAAAAAAAAA    1250
AAAAAAAAAG GGGGCGGCCG C                                   1271
```

Figure 2
cip1 coding sequence (SEQ ID NO:2)

```
ATGGTTCGCC GGACTGCTCT GCTGGCCCTT GGGGCTCTCT CAACGCTCTC      50
TATGGCCCAA ATCTCAGACG ACTTCGAGTC GGGCTGGGAT CAGACTAAAT     100
GGCCCATTTC GGCACCAGAC TGTAACCAGG GCGGCACCGT CAGCCTCGAC     150
ACCACAGTAG CCCACAGCGG CAGCAACTCC ATGAAGGTCG TTGGTGGCCC     200
CAATGGCTAC TGTGGACACA TCTTCTTCGG CACTACCCAG GTGCCAACTG     250
GGGATGTATA TGTCAGAGCT GGATTCGGC TTCAGACTGC TCTCGGCAGC      300
AACCACGTCA CATTCATCAT CATGCCAGAC ACCGCTCAGG GAGGGAAGCA     350
CCTCCGAATT GGTGGCCAAA GCCAAGTTCT CGACTACAAC CGCGAGTCCG     400
ACGATGCCAC TCTTCCGGAC CTGTCTCCCA ACGGCATTGC CTCCACCGTC     450
ACTCTGCCTA CCGGCGCGTT CCAGTGCTTC GAGTACCACC TGGGCACTGA     500
CGGAACCATC GAGACGTGGC TCAACGGCAG CCTCATCCCG GGCATGACCG     550
TGGGCCCTGG CGTCGACAAT CCAAACGACG CTGGCTGGAC GAGGGCCAGC     600
TATATTCCGG AGATCACCGG TGTCAACTTT GGCTGGGAGG CCTACAGCGG     650
AGACGTCAAC ACCGTCTGGT CGACGACAT CTCGATTGCG TCGACCCGCG      700
TGGATGCGG CCCCGGCAGC CCCGGCGGTC CTGGAAGCTC GACGACTGGG      750
CGTAGCAGCA CCTCGGGCCC GACGAGCACT TCGAGGCCAA GCACCACCAT     800
TCCGCCACCG ACTTCCAGGA CAACGACCGC CACGGGTCCG ACTCAGACAC     850
ACTATGGCCA GTGCGGAGGG ATTGGTTACA GCGGGCCTAC GGTCTGCGCG     900
AGCGGCACGA CCTGCCAGGT CCTGAACCCA TACTACTCCC AGTGCTTATA     950
A                                                         951
```

Figure 3A
CIP1 protein sequence (SEQ ID NO:3)

```
MVRRTALLAL GALSTLSMAQ ISDDFESGWD QTKWPISAPD CNQGGTVSLD    50
TTVAHSGSNS MKVVGGPNGY CGHIFFGTTQ VPTGDVYVRA WIRLQTALGS   100
NHVTFIIMPD TAQGGKHLRI GGQSQVLDYN RESDDATLPD LSPNGIASTV   150
TLPTGAFQCF EYHLGTDGTI ETWLNGSLIP GMTVGPGVDN PNDAGWTRAS   200
YIPEITGVNF GWEAYSGDVN TVWFDDISIA STRVGCGPGS PGGPGSSTTG   250
RSSTSGPTST SRPSTTIPPP TSRTTTATGP TQTHYGQCGG IGYSGPTVCA   300
SGTTCQVLNP YYSQCL                                       316
```

Figure 3B
CIP1 signal sequence (SEQ ID NO:4)

```
MVRRTALLAL GALSTLSMA                                     19
```

Figure 3C
CIP1 mature protein sequence (SEQ ID NO:5)

```
QISDDFESGW DQTKWPISAP DCNQGGTVSL DTTVAHSGSN SMKVVGGPNG    50
YCGHIFFGTT QVPTGDVYVR AWIRLQTALG SNHVTFIIMP DTAQGGKHLR   100
IGGQSQVLDY NRESDDATLP DLSPNGIAST VTLPTGAFQC FEYHLGTDGT   150
IETWLNGSLI PGMTVGPGVD NPNDAGWTRA SYIPEITGVN FGWEAYSGDV   200
NTVWFDDISI ASTRVGCGPG SPGGPGSSTT GRSSTSGPTS TSRPSTTIPP   250
PTSRTTTATG PTQTHYGQCG GIGYSGPTVC ASGTTCQVLN PYYSQCL     297
```

Figure 4: Full length sequence of *cip2* (SEQ ID NO:6)

```
   1  ATGGCTTCCC GCTTCTTTGC TCTTCTCCTT TTAGCGATCC CAATCCAGGC
  51  CCAATCTCCA GTCTGGGGAC AATGTGGTGG AATTGGTTGG TCTGGCCCAA
 101  CAACTTGTGT TGGAGGTGCG ACTTGTGTAT CATATAACCC TTATTACTCG
 151  CAATGTATTC CCAGTACACA GGCTTCATCG AGCATAGCCT CTACAACGCT
 201  GGTCACATCA TTTACGACCA CCACTGCTAC GAGGACTTCG GCATCAACGC
 251  CTCCAGCGAG CAGTACAGGT GCAGGCGGCG CAACATGCTC AGCACTGCCG
 301  GGCTCCATTA CCCTGAGATC CAACGCAAAG CTCAACGATC TGTTTACAAT
 351  GTTCAATGGA GATAAGGTCA CCACGAAAGA CAAATTCTCG TGCCGCCAGG
 401  CAGAGATGTC GGAGCTAATA CAACGATATG AGCTCGGCAC CCTGCCCGGA
 451  CGACCAAGCA CTCTCACAGC CTCATTCTCG GGCAATACGT TGACCATCAA
 501  TTGCGGAGAG GCCGGAAAGT CAATTTCATT CACAGTCACG ATCACTTATC
 551  CATCTTCCGG AACAGCACCA TACCCTGCGA TTATCGGCTA TGGAGGCGGC
 601  AGTCTTCCAG CTCCCGCCGG GGTTGCCATG ATCAACTTTA CAATGACAA
 651  CATAGCAGCC AAGTTAATA CAGGCAGCCG CGGACAGGGC AAGTTCTACG
 701  ATCTCTACGG GAGCTCGCAC TCCGCGGGCG CCATGACCGC ATGGGCCTGG
 751  GGAGTAAGCC GAGTCATTGA TGCTCTTGAG CTTGTACCAG GCGCAAGAAT
 801  AGACACCACC AAGATTGGCG TGACGGGGTG TTCACGAAAT GGCAAAGGCG
 851  CAATGGTCGC AGGTGCTTTC GAGAAACGAA TCGTTCTGAC ACTTCCCCAG
 901  GAGTCGGGCG CCGGTGGCTC TGCGTGCTGG AGGATTTCAG ACTACTTAAA
 951  GTCCCAAGGA GCCAATATCC AGACCGCGTC TGAGATCATT GGCGAAGACC
1001  CCTGGTTCTC GACTACTTTC AACAGCTACG TCAACCAAGT GCCGGTGTTG
1051  CCGTTTGACC ACCATTCGCT TGCTGCCTTG ATAGCCCCGA GAGGATTATT
1101  CGTCATCGAC AACAATATTG ACTGGCTCGG CCCACAAAGC TGCTTTGGCT
1151  GTATGACAGC TGCTCACATG GCATGGCAAG CTTTGGGTGT CTCGGACCAC
1201  ATGGGCTATT CGCAGATTGG AGCTCACGCA CACTGCGCGT TCCCATCAAA
1251  CCAGCAATCG CAACTTACTG CCTTTGTTCA GAATTCTTG CTGGGCCAGT
1301  CCACAAATAC GGCGATTTTC CAAAGCGACT TTTCGGCCAA TCAAAGCCAA
1351  TGGATCGACT GGACAACCCC AACGCTGAGT TGA
```

Figure 5A: CIP2 protein sequence (SEQ ID NO:7)

```
  1   MASRFFALLL LAIPIQAQSP VWGQCGGIGW SGPTTCVGGA TCVSYNPYYS
 51   QCIPSTQASS SIASTTLVTS FTTTTATRTS ASTPPASSTG AGGATCSALP
101   GSITLRSNAK LNDLFTMFNG DKVTTKDKFS CRQAEMSELI QRYELGTLPG
151   RPSTLTASFS GNTLTINCGE AGKSISFTVT ITYPSSGTAP YPAIIGYGGG
201   SLPAPAGVAM INFNNDNIAA QVNTGSRGQG KFYDLYGSSH SAGAMTAWAW
251   GVSRVIDALE LVPGARIDTT KIGVTGCSRN GKGAMVAGAF EKRIVLTLPQ
301   ESGAGGSACW RISDYLKSQG ANIQTASEII GEDPWFSTTF NSYVNQVPVL
351   PFDHHSLAAL IAPRGLFVID NNIDWLGPQS CFGCMTAAHM AWQALGVSDH
401   MGYSQIGAHA HCAFPSNQQS QLTAFVQKFL LGQSTNTAIF QSDFSANQSQ
451   WIDWTTPTLS
```

Figure 5B: CIP2 signal sequence (SEQ ID NO:8)

```
  1   MASRFFALLL LAIPIQA
```

Figure 5C: CIP2 mature protein sequence (SEQ ID NO:9)

```
  1   QSPVWGQCGG IGWSGPTTCV GGATCVSYNP YYSQCIPSTQ ASSSIASTTL
 51   VTSFTTTTAT RTSASTPPAS STGAGGATCS ALPGSITLRS NAKLNDLFTM
101   FNGDKVTTKD KFSCRQAEMS ELIQRYELGT LPGRPSTLTA SFSGNTLTIN
151   CGEAGKSISF TVTITYPSSG TAPYPAIIGY GGGSLPAPAG VAMINFNNDN
201   IAAQVNTGSR GQGKFYDLYG SSHSAGAMTA WAWGVSRVID ALELVPGARI
251   DTTKIGVTGC SRNGKGAMVA GAFEKRIVLT LPQESGAGGS ACWRISDYLK
301   SQGANIQTAS EIIGEDPWFS TTFNSYVNQV PVLPFDHHSL AALIAPRGLF
351   VIDNNIDWLG PQSCFGCMTA AHMAWQALGV SDHMGYSQIG AHAHCAFPSN
401   QQSQLTAFVQ KFLLGQSTNT AIFQSDFSAN QSQWIDWTTP TLS
```

**Figure 6: Alignment of Cip2 with *R.flavefaciens* cesA CAB55348**

Cip2 has a predicted N-terminal signal sequence of 17 amino acids followed by 36 amino acids comprising a carbohydrate binding module of family CBM1 and a linker region which ends at approximately amino acid 95.

```
                                    1                                                50
R.flavefaciens cesA   (SEQ ID NO: 18)  (1) MKKHFVVGFTTKRFLRTGTSLALSTSTLSLLPSAPRLSSAAGTTKTMPLG
       CIP2 040302   (SEQ ID NO:  7)  (1) -------------------------------------------------
         Consensus   (SEQ ID NO: 19)  (1)
                                    51                                               100
R.flavefaciens cesA   (51)  DSITYGMADEGGYRKYLSYFLQQKGYTNVDLVGPEGKDSASFNYNGQSVK
       CIP2 040302    (1)  -------------------------------------------------
         Consensus   (51)
                                   101                                               150
R.flavefaciens cesA  (101)  YDDNHAGYSGYTITNLPGGWFGQLNGILETMQGGDYIKKYSPDIILLQIG
       CIP2 040302    (1)  -------------------------------------------------
         Consensus  (101)
                                   151                                               200
R.flavefaciens cesA  (151)  TNDVSNGHLDGSEERLHKLLDYLRENMPSNGKVFLTTIPDLGNSGWGGNS
       CIP2 040302    (1)  -------------------------------------------------
         Consensus  (151)
                                   201                                               250
R.flavefaciens cesA  (201)  NGDIAKYNELIKKVANDYSSKNVIYADIHSVIDASKDLADGVHPNAGGYE
       CIP2 040302    (1)  -------------------------------------------------
         Consensus  (201)
                                   251                                               300
R.flavefaciens cesA  (251)  KMGKYWLEQIEGYLKASDGPQQTQPTQFSQGDSGPELIYGDLDGDKTITS
       CIP2 040302    (1)  -----MASRFFALLLLAIPIQAQSPVWGQCGGIG---------------
         Consensus  (251)       A  L   A    Q    P      G G
                                   301                                               350
R.flavefaciens cesA  (301)  FDAVIMRKGLINDFKDNNVKKAADIDQNGKAEVADLVQLQSFIIGKIKEF
       CIP2 040302   (30)  WSGPTTCVGGATCVSYNPYYSQCIPSTQASSSIASTTLVTSFTTTTATRT
         Consensus  (301)  F A    G    N        NA A IA   L SF
                                   351                                               400
R.flavefaciens cesA  (351)  TVAEKTVTEKPVFEKSYN-FPAVNQLKSSKDIPDPFIFMDGSKVESTDDW
       CIP2 040302   (80)  SASTPPASSTGAGGATCSALPGSITLRSNAKLNDLFTMFNGDKVTTKDKF
         Consensus  (351)  S A    S       S     PA   LKS    I D F   G KV  S D F
                                   401                                               450
R.flavefaciens cesA  (400)  WKRQSEISCMYEYYMYGKWIDGSDDETTYSISGNSMTINVKRKSTGKTAS
       CIP2 040302  (130)  SCRQAEMSELIQRYELGTLPG-RPSTLTASFSGNTLTINCG--EAGKSIS
         Consensus  (401)    RQAEIS L   Y  G          T S SGNSLTIN    GKS S
                                   451                                               500
R.flavefaciens cesA  (450)  FKAVINLPKNVRHEGGAPVILGMHKGTSFSTATSNGYAVTTYDSDGMFSA
       CIP2 040302  (177)  FTVTITYPS    SGTAFYPAIIGYGGGSLPAPAGVAMINFNNDNIAAQ
         Consensus  (451)  F    I P      G     AI    S    G AMI  F D I  A
                                   501                                               550
R.flavefaciens cesA  (500)  PGTAQDNNQHKGAFYDLYFYGRNWDEQTGDLMAWSWGISRILDALYNGAA
       CIP2 040302  (222)  VNTGSRG---QGKFYDLYGS----SHSAGAMTAWAWGVSRVIDALELVPG
         Consensus  (501)      TA   G   FYDLY        G L  AWAWGISRIIDAL   A
                                   551                                               600
R.flavefaciens cesA  (550)  KELNINPDSSIVTGVSRYGKAASVCGAFDTRIKMCAPSCSGAGGLALYRY
       CIP2 040302  (265)  ARIDTTKIG--VTGCSRNGKGAMVAGAFEKRIVLTLPQESGAGGSACWRI
         Consensus  (551)    I         VTG SR GKAA V GAFD RI L  P  SGAGG A WR
                                   601                                               650
R.flavefaciens cesA  (600)  SSVGKTYDFSSKGGSSSYTYKENEPLGSLQASGEQGWFNGRFMEFRN-AE
       CIP2 040302  (313)  SDYLKSQGANIQTAS--------------EIIGEDPWFSTTFNSYVNQVP
         Consensus  (601)  S   KS   AS                    GE  WF   F  F N
                                   651                                               700
R.flavefaciens cesA  (649)  QFPMDQHMLGALCCDPDRYLFIIGSCESEDWVNAPSVWMAYLGMKHVWDY
       CIP2 040302  (349)  VLPFDHHSLAALIAPRGLFVIDN----NIDWLGPQSCFGCMTAAHMAWQA
         Consensus  (651)     P D H LAAL    FL        DWL  S F  A      W
                                   701                                               750
R.flavefaciens cesA  (699)  VGISDHLAINIHKSGHAVIAEDIEKMVQYFDYHVYGIQPKMNLEELQTSV
       CIP2 040302  (395)  LGVSDHMGYSQIGAHAHCAFPSNQQSQLTAFVQKFLLGQSTNTAIFQSDF
         Consensus  (701)  LGISDHLA     A                    F I     N   QS
                                   751           770
R.flavefaciens cesA  (749)  FALPKNKDSFADTFASKWLY
       CIP2 040302  (445)  SANQSQWIDWTTPTLS----
         Consensus  (751)   A    N F   S
```

Figure 7: abf2 nucleic acid sequence (SEQ ID NO:10)

```
  1    ATGGAGCTTA AAGCACTCAG TGCCGTTGTG CTGAGCTTTG TAACTCTTGT
 51    CGCGGCAGCA CCGGCGACCT GCACGCTTCC GTCCACATAC CGCTGGAATT
101    CGACCGGTGC TTTAGCCAGC CCGAAATCAG GCTGGGTCTC GCTGAAAGAC
151    TTCTCCCATG TCATTTATAA TGGCCAGCAT CTTGTATGGG GCTCGACTCA
201    TGACACAGGA ACAATCTGGG GTTCAATGAA CTTTGGTCTG TTCAGTGACT
251    GGTCCAATAT GGCAACGGCA AGCCAGAACA AAATGACTCC CGGCACTGTT
301    GCTCCTACCG TCTTCTACTT TGCCCCGAAG AATATTTGGG TACTCGCCTA
351    TCAATGGGGC CCGACCACGT TTTCCTACCT GACGTCAAGC AACCCCTCCA
401    GCGTCAATGG ATGGTCGTCA CCACAGCCTC TCTTCTCCGG CAGTATCTCA
451    GGCTCCAGCC CGCTGGATCA GACGGTCATT GGCGACAGCA CGAACATGTA
501    TCTGTTCTTC GCGGGGGACG ACGGGAAAAT CTACAGGGCG AGCATGCCTA
551    TCGGTAACTT CCCCGGAAGC TTCGGTTCGA CGTCAACGGT GGTCCTGAGC
601    GATGAAAGGA ACAATCTGTT TGAGGCAGTT CAGGTCTATA CCGTCTCAGG
651    GCAGAAGCAA TATCTCATGA TTGTCGAGGC AATAGGCGCA AATGGCCGGT
701    ATTTCCGGTC CTTCACAGCG ACAAACCTCG GCGGCACATG GACTCCGCAA
751    GCCACCAGCG AAAGTCAGCC GTTTGCCGGT AAGCAAACA GTGGCGCTAC
801    CTGGACAAAC GACATCAGTC ATGGTGATCT AATTCGTAGC AACCCTGATC
851    AGACAATGAC TATCGACCCT TGCAATCTGC AGTTCTTGTA CCAGGGGAGA
901    GCGACAAACT CTGGCGGCGA CTACGGCCTC TTGCCCTATC GACCAGGGCT
951    GCTAACTCTC CAGCGC
```

Figure 8A: Abf2 amino acid sequence   (SEQ ID NO:11)

```
  1    MELKALSAVV LSFVTLVAAA PATCTLPSTY RWNSTGALAS PKSGWVSLKD
 51    FSHVIYNGQH LVWGSTHDTG TIWGSMNFGL FSDWSNMATA SQNKMTPGTV
101    APTVFYFAPK NIWVLAYQWG PTTFSYLTSS NPSSVNGWSS PQPLFSGSIS
151    GSSPLDQTVI GDSTNMYLFF AGDDGKIYRA SMPIGNFPGS FGSTSTVVLS
201    DERNNLFEAV QVYTVSGQKQ YLMIVEAIGA NGRYFRSFTA TNLGGTWTPQ
251    ATSESQPFAG KANSGATWTN DISHGDLIRS NPDQTMTIDP CNLQFLYQGR
301    ATNSGGDYGL LPYRPGLLTL QR
```

Figure 8B: Abf2 signal sequence   (SEQ ID NO:12)

```
  1    MELKALSAVV LSFVTLVAA
```

Figure 8C: Abf2 mature protein sequence   (SEQ ID NO:13)

```
  1    APATCTLPST YRWNSTGALA SPKSGWVSLK DFSHVIYNGQ HLVWGSTHDT
 51    GTIWGSMNFG LFSDWSNMAT ASQNKMTPGT VAPTVFYFAP KNIWVLAYQW
101    GPTTFSYLTS SNPSSVNGWS SPQPLFSGSI SGSSPLDQTV IGDSTNMYLF
151    FAGDDGKIYR ASMPIGNFPG SFGSTSTVVL SDERNNLFEA VQVYTVSGQK
201    QYLMIVEAIG ANGRYFRSFT ATNLGGTWTP QATSESQPFA GKANSGATWT
251    NDISHGDLIR SNPDQTMTID PCNLQFLYQG RATNSGGDYG LLPYRPGLLT
301    LQR
```

Figure 9: GH62 family alignment:
Abf2 is a member of the glycosyl hydrolase family 62. It is predicted to have an N-terminal signal sequence of 19 amino acids.

```
                                      1                                                    50
      C.carbonum ARF1 (SEQ ID NO:20)  (1)  ------MRFVPDLSFSAAAVALLASTASAQ--------------------
S. thermoviolaceus stxIV (SEQ ID NO:21) (1) MSFHRSLPFRPKRLFGVLAPLLLAGVMSTQPAGAATVVPSDDVQGTGRQS
                 Abf2 (SEQ ID NO:11)  (1)  ---------MELKALSAVVLSFVTLVAAAP--------------------
            Consensus (SEQ ID NO:23)  (1)        L FMP KAFSALALALLA VASAQ
                                      51                                                   100
      C.carbonum ARF1 (SEQ ID NO:20) (25)  ------------SCKLPTSYKWTSSGALAQPKSGWANLKDFTISSLNGKHLV
S. thermoviolaceus stxIV (SEQ ID NO:21) (51) QLTDGFGTRASCELPSTYRWTSTGALAQPRSGWVSLKDFTVVPYNGQHLV
                 Abf2 (SEQ ID NO:11) (22)  ---------ATCTLPSTYRWNSTGALASPKSGWVSLKDFSHVIYNGQHLV
            Consensus (SEQ ID NO:23) (51)             ASC LPSTYRWTSTGALAQPKSGWVSLKDFTIV YNGQHLV
                                      101                                                  150
      C.carbonum ARF1                (65)  YATDHDTGSKYGSMAFSPTGSFSEMASASQTATFFTAVAPTLFRFAPKNI
S. thermoviolaceus stxIV            (101)  YATTHDTGTRWGSMNFEPFGDWSQMATARQNAMNSPTVAPTLFYFAPKDI
                 Abf2               (63)   WGSTHDTGTIWGSMNFGLFSDWSNMATASQNKMTPGTVAPTVFYFAPKNI
            Consensus               (101)  YATTHDTGTKWGSMNF PFGDWSNMATASQNAM   TVAPTLFYFAPKNI
                                      151                                                  200
      C.carbonum ARF1               (115)  WVLAYQWGPTTFSYRTSSDPTNPNSWGGVQTLFSGKISGSSTGAIDQTVI
S. thermoviolaceus stxIV            (151)  WVLAYQWGGSAFSYRTSHDPTDPNGWSSEQVLFSGSIADSATGPIDCTLI
                 Abf2               (113)  WVLAYQWGPTTFSYLTSSNPSSVNGWSSPQPLFSGSISGS--SPLDQTVI
            Consensus               (151)  WVLAYQWGPTTFSYRTSSDPT PNGWSS Q LFSGSISGSATGPIDQTVI
                                      201                                                  250
      C.carbonum ARF1               (165)  GDAINMYLFFAGDNGKIYRSSMPKANFPGSFGTASTVIMSDSTNNLFEAV
S. thermoviolaceus stxIV            (201)  GDDTHMYLFFAGDNGKIYRASMPIGDFPGSFGSTATVVMSDTRNNLFEAP
                 Abf2               (161)  GDSTNMYLFFAGDDGKIYRASMPIGNFPGSFGSTSTVVLSDERNNLFEAV
            Consensus               (201)  GDATNMYLFFAGDNGKIYRASMPIGNFPGSFGSTSTVVMSDSRNNLFEAV
                                      251                                                  300
      C.carbonum ARF1               (215)  QVYTVKGGG-YLMIVEAVGSGG-RYFRSFTASSLSGSWTPNAATESNPFA
S. thermoviolaceus stxIV            (251)  QVYKLQGQNRYLMIVEAIGACGQRYFRSFTATSLDGEWTPQATSESNPFA
                 Abf2               (211)  QVYTVSCQKQYLMIVEAICANG-RYFRSFTATNLCGTWTPQATSESQPFA
            Consensus               (251)  QVYTV GQ  YLMIVEAIGANG RYFRSFTATSL GSWTPQATSESNPFA
                                      301                                                  350
      C.carbonum ARF1               (263)  GKANSGATWTNDISHGDLVKVTNDETMTVDPCNLQLLYQGRAPNSGGDYD
S. thermoviolaceus stxIV            (301)  GKANSGATWTDDISHGELIRTTADQTMTVDPCNLQLLYQGRDPGSGGTYD
                 Abf2               (260)  GKANSGATWTNDISHGDLIRSNPDQTMTIDPCNLQFLYQGRATNSGGDYG
            Consensus               (301)  GKANSGATWTNDISHGDLIRST DQTMTVDPCNLQLLYQGRAPNSGGDYD
                                      351          363
      C.carbonum ARF1               (313)  RLPYRPGLLT---
S. thermoviolaceus stxIV            (351)  LLPYRPGLLTLQR
                 Abf2               (310)  LLPYRPGLLTLQR
            Consensus               (351)  LLPYRPGLLTLQR
```

Figure 10: axe2 cDNA (SEQ ID NO:14)

```
ATGCGCGCCC TCTCACTCTC CCTCCCCCTC TCCCTCTCGC TGCTCGCCGC      50
CAGCTCAACA GCGGCAACGA CATGCGCAAA GGGCCTCTAC ATGGTCGTTG     100
CCCGCGGCAG CGAGGAGCCC GCCGGCACGG GCGTGACGGG CAACCTCACG     150
AGCCAAATCG CCGCAAAGGT GCCCGGCAGC GAGGTCGTGG CGGTGGACTA     200
CCCGGCCAGC TTTGACGACT ACGAGGATTC CGAGGGCGAC GGCGTCAAGG     250
CGATGCGGCA GCTGCTCAAC AGCTACGCCG AGGCCTGTCC GGGAAACAAG     300
ATTGCGGTGC TGGGATACTC TCAGGGCGCC CAAGTCGCAA CAGACACCAT     350
CTGCGGCGGT GCCGGCGATC CGTTTACCAG CGACAAGGGC ATGTCTGACG     400
ATGTCATGGA CGACGTCGTT GCCGTGGCCA TTTTCGGAGA CCCAACCCAT     450
GTCGCCAACA TGACGTACGA CCGAGGCACC AGCATTCACA ACGGGCTCTT     500
CAACCGGAGC TCGTCCAGCA TCGAGGTCTG CAAGTCGTAC GCCAGCCGCA     550
TCGTCTCGTA CTGCGACACG GGCGACATCT ACTGCGACGC CGGCAGCAAC     600
TCGACCGTTC ACCACATGTA CATCCAGCGC TACGGCGACG AAATCGTCGA     650
CTTTGTCGTC AGCCAGTTTG AGAAGAGCAC CAGCTCGGGA TCGGGGTCGG     700
GTACTAATGC CACCACGACC ACGGCTCCGG CTCCCACCGT GTCTCCTACC     750
ACCACCAGCG GTGGCAACAG CACAGTGCCT ACGCGAACCG GTGGCCCGAC     800
GACGAGTTCG ACGCAAGGAT CGGGTGCGAG TGCTTTGACG AGCAGTTTGA     850
TGCTGGGAGG TCTTTTGACG GTTTTGACGG CGGTGTCTCA GATGCTGTGA     900
```

Figure 11A: AXE2 amino acid sequence  (SEQ ID NO:15)

```
1    MRALSLSLPL SLSLLAASST AATTCAKGLY MVVARGSEEP AGTGVTGNLT  50
51   SQIAAKVPGS EVVAVDYPAS FDDYEDSEGD GVKAMRQLLN SYAEACPGNK  100
101  IAVLGYSQGA QVATDTICGG AGDPFTSDKG MSDDVMDDVV AVAIFGDPTH  150
151  VANMTYDRGT SIHNGLFNRS SSSIEVCKSY ASRIVSYCDT GDIYCDAGSN  200
201  STVHHMYIQR YGDEIVDFVV SQFEKSTSSG SGSGTNATTT TAPAPTVSPT  250
251  TTSGGNSTVP TRTGGPTTSS TQGSGASALT SSLMLGGLLT VLTAVSQML   299
```

Figure 11B: AXE2 signal sequence   (SEQ ID NO:16)
```
1    MRALSLSLPL SLSLLAASST A                                21
```

Figure 11C: AXE2 mature protein sequence   (SEQ ID NO:17)

```
1    ATTCAKGLYM VVARGSEEPA GTGVTGNLTS QIAAKVPGSE VVAVDYPASF  50
51   DDYEDSEGDG VKAMRQLLNS YAEACPGNKI AVLGYSQGAQ VATDTICGGA  100
101  GDPFTSDKGM SDDVMDDVVA VAIFGDPTHV ANMTYDRGTS IHNGLFNRSS  150
151  SSIEVCKSYA SRIVSYCDTG DIYCDAGSNS TVHHMYIQRY GDEIVDFVVS  200
201  QFEKSTSSGS GSGTNATTTT APAPTVSPTT TSGGNSTVPT RTGGPTTSST  250
251  QGSGASALTS SLMLGGLLTV LTAVSQML                         278
```

Figure 12: axe2 alignment

CE5 family member
Axe2 is a member of the carbohydrate esterase family 5 (CE5). It is predicted to have N-terminal signal sequence of 21 amino acids.
It has a putative GPI-anchor attachment site at amino acid number 274, corresponding to the serine residue at position 291 in the alignment (Udenfriend, S. and K. Kodukula. 1995. Prediction of ω site in nascent precursor of glycophosphatidylinositol protein. Methods in Enzymology. 250:57-82).

```
                                                                            50
T. reesei axe1 (SEQ ID NO:24)  (1) MPSVKETLTLLLSQAFLATGSPVDGETVVKRQCPAIHVFGARETTVSQGY
          axe2 (SEQ ID NO:15)  (1) --MRALSLSLPLSLSLLAASS-----TAATTCAKGLYMVVARGSEEPAGT
     Consensus (SEQ ID NO:25)  (1)    SLSL LS A LA  S      T          AIHM  AR S     C
                                    51                                                  100
T. reesei axe1                (51) GSSATVVNLVIQAHPGTTSEAIVYPACGGQASCGGISYANSVVNGTNAAA
          axe2                (44) GVTGNLTSQIAAKVPGSEVVAVDYPAS-------FDDYEDSEGDGVKAMR
     Consensus                (51)  G SA L   I     PGS   AI YPA           Y S   C   A
                                   101                                                  150
T. reesei axe1               (101) AAINNFHNSCPDTQLVLVGYSQGAQIFDNALCGGGDPGEGITNTAVPLTA
          axe2                (87) QLLNSYAEACPGNKIAVLGYSQGAQVATDTICGGAG---DPFTSDKGMSD
     Consensus               (101)    IN F  ACP    I LLGYSQGAQI     ICCGA        S  LS
                                   151                                                  200
T. reesei axe1               (151) GAVSAVKAAIFMGDPRNIHGLPYNVGTCTTQGFDARPAG---FVCPSASK
          axe2               (134) DVMDDVVAVAIFGDPTHVANMTYDRGTSIHNGLFNRSSSSIEVCKSYASR
     Consensus               (151)   M  V A  IF GDP   I  L Y  GT  NG  R A           ASK
                                   201                                                  250
T. reesei axe1               (198) IKSYCDAADPYCCTGNDPNVHQGYGQEYGQQALAFINSQLSSGGSQPPGG
          axe2               (184) IVSYCDTGDIYCDAGSNSTVHHMYIQRYGDEIVDFVVSQFEKSTSSGSGS
     Consensus               (201) I SYCD AD YC G   VH  Y Q YG   L FI SQ       S      G
                                   251                                                  300
T. reesei axe1               (248) --------GPTSTSRPTSTRTGSSPGPTQTHWGQCG---GQGWTGPTQCE
          axe2               (234) GTNATTTTAPAPTVSPTTTSGGNSTVPTRTGGPTTSSTQGSGASALTSSL
     Consensus               (251)         AP T  PTST   GS   PT T       G G SA T
                                   301          316
T. reesei axe1               (287) SGTTCQVISQWYSQCL
          axe2               (284) MLGGLLTVLTAVSQML
     Consensus               (301)         T   SQ L
```

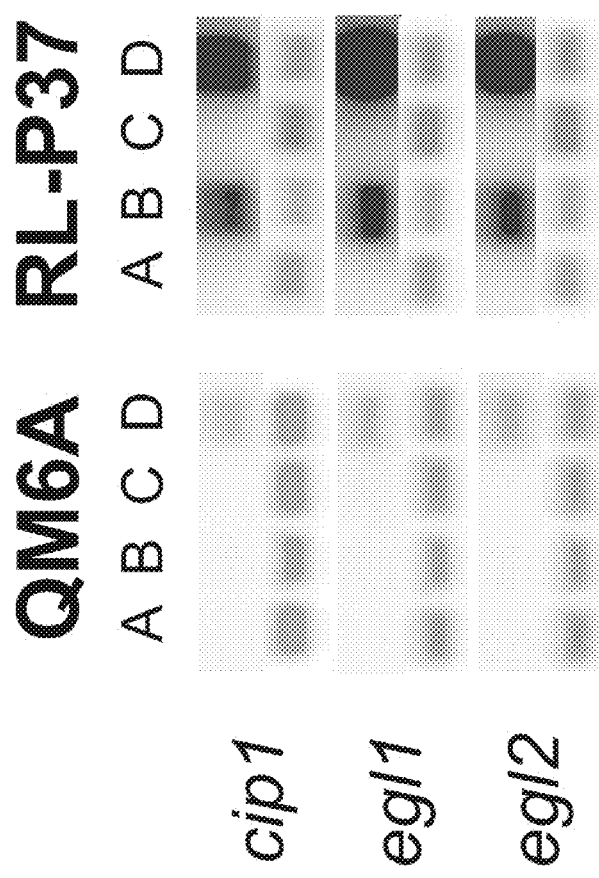

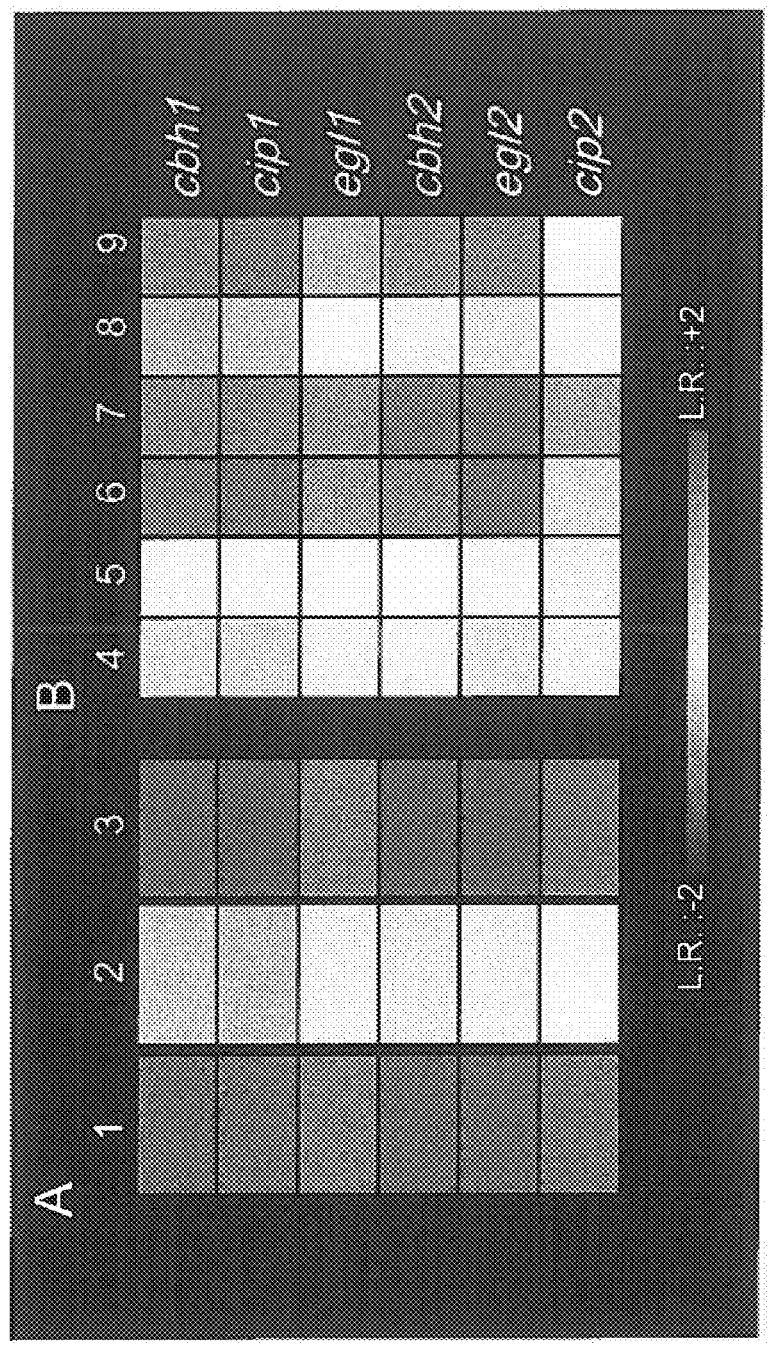
Figure 14: Microarray Analysis

Figure 16: Alignment of Cip1 with the putative secreted hydrolase Streptomyces coelicolor A3 (accession number CAA18323).

```
                                                      1                                                    50
                       cip1 (SEQ ID NO:3)     (1)  --------------------------------------------------
Streptomyces coelicolor A3 (SEQ ID NO:26)     (1)  MRTRVLRLLRRPWTAAVAAVALVVSVLVAMPASGAAAAACRVDYCVDAWA
                  Consensus (SEQ ID NO:27)    (1)
                                                      51                                                   100
                       cip1                   (1)  --------------------------------------------------
Streptomyces coelicolor A3                   (51)  GGYLARVRITNLGPAVSDWRLTWTYTGDQQVTSAWNATVTQTGASVVAVD
                  Consensus                  (51)
                                                      101                                                  150
                       cip1                   (1)  --------------------------------------------------
Streptomyces coelicolor A3                  (101)  AGWNGAVSTGGTARFGLQGTWRSADPAPDPALNGTSCGDGGTPTATPTT
                  Consensus                 (101)
                                                      151                                                  200
                       cip1                   (1)  -----------MVRRTALLALGALSTLSMAQISDDFESGWDQTKWPISAP
Streptomyces coelicolor A3                  (151)  SPTAPPTTPPTTPPPTTPPPAAECGDAVTCSGFEDQAGPRPSGDWRFTAP
                  Consensus                 (151)             T    A    T    DD          W   SAP
                                                      201                                                  250
                       cip1                  (40)  DCNQGGTVSLDTTVAHSGSNSMKVVGGPNGYCGHIFFGTTQVPTGD---V
Streptomyces coelicolor A3                  (201)  DCQGTGTAAVDSAVSHAGGRSLRVDG-RAGYCNHAFVAHTADLSSVGPVM
                  Consensus                 (201)  DCN  GT  ALDS VAHAG  SLKV G   GYC H FA T    S    M
                                                      251                                                  300
                       cip1                  (87)  YVRAWIRLQTALGSNHVTFIIMPDTAQGGKHLRIGGQSQVLDYNRESDDA
Streptomyces coelicolor A3                  (250)  YVRMWVRHTTALPTSHVTFVSMPDSAQGGRALRVGGQNGALQWNRESDDA
                  Consensus                 (251)  YVR WIR   TAL S HVTFI MPDSAQGGK LRIGGQ    L WNRESDDA
                                                      301                                                  350
                       cip1                 (137)  TLPDLSPNGIASTVTLPTGAFQCFEYHLGTDGT-IETWLNGSLIPGMTVG
Streptomyces coelicolor A3                  (300)  TLPAQSPAGVALSRPLPTDGWQCLRFAIDTSAAGLDTWLGDEQVPGLHAD
                  Consensus                 (301)  TLP  SP GIA S  LPT AFQC  F  I T A  IDTWL    IPGL
                                                      351                                                  400
                       cip1                 (186)  PGVDNPNDAGWTRASYIPEITGVNFGWEAYSGDVNTVWFDDISIASTRVG
Streptomyces coelicolor A3                  (350)  GVPTQDVDQQWLTRGTAPRPTALRLGWESYATGDDTVWFDDVAVGSAPIG
                  Consensus                 (351)        N  D  W      P  TAL  GWEAYA    TVWFDDIAIAS  IG
                                                      401                                                  450
                       cip1                 (236)  CGPCSPCCPGSSTTGRSSTSCPTSTSRPSTTIPPPTSRTTTATCPTQTHY
Streptomyces coelicolor A3                  (400)  C-------------------------------------------------
                  Consensus                 (401)  C
                                                      451                                   481
                       cip1                 (286)  CQCCGIGYSGPTVCASGTTCQVLNPYYSQCL
Streptomyces coelicolor A3                  (401)  -------------------------------
                  Consensus                 (451)
```

Samples:
1) MW markers
2) transformant #1
3) transformant #2
4) transformant #3
5) transformant #4
6) transformant #5
7) transformant #6
8) transformant #7
9) transformant #8
10) transformant #9
11) transformant #10
12) transformant #11

```
SEQUENCE LISTING

<160> NUMBER OF SEQ ID NOS: 59

<210> SEQ ID NO 1
<211> LENGTH: 1221
<212> TYPE: DNA
<213> ORGANISM: Trichoderma reesei

<400> SEQUENCE: 1
gactagttca taatacagta gttgagttca tagcaacttc actctctagc tgaacaaatt      60
atctgcgcaa acatggttcg ccggactgct ctgctggccc ttggggctct ctcaacgctc     120
tctatggccc aaatctcaga cgacttcgag tcgggctggg atcagactaa atggcccatt     180
tcggcaccag actgtaacca gggcggcacc gtcagcctcg acaccacagt agcccacagc     240
ggcagcaact ccatgaaggt cgttggtggc cccaatggct actgtggaca catcttcttc     300
ggcactaccc aggtgccaac tggggatgta tatgtcagag cttggattcg gcttcagact     360
gctctcggca gcaaccacgt cacattcatc atcatgccag acaccgctca gggagggaag     420
cacctccgaa ttggtggcca aagccaagtt ctcgactaca accgcgagtc cgacgatgcc     480
```

```
actcttccgg acctgtctcc caacggcatt gcctccaccg tcactctgcc taccggcgcg    540
ttccagtgct tcgagtacca cctgggcact gacggaacca tcgagacgtg gctcaacggc    600
agcctcatcc cgggcatgac cgtgggccct ggcgtcgaca atccaaacga cgctggctgg    660
acgagggcca gctatattcc ggagatcacc ggtgtcaact ttggctggga ggcctacagc    720
ggagacgtca acaccgtctg gttcgacgac atctcgattg cgtcgacccg cgtgggatgc    780
ggccccggca gccccggcgg tcctggaagc tcgacgactg ggcgtagcag cacctcgggc    840
ccgacgagca cttcgaggcc aagcaccacc attccgccac cgacttccag gacaacgacc    900
gccacgggtc cgactcagac acactatggc cagtgcggag ggattggtta cagcgggcct    960
acggtctgcg cgagcggcac gacctgccag gtcctgaacc catactactc ccagtgctta   1020 taagggggatg agcatggagt gaagtgaagt gaagtggaga gagttgaagt ggcattgcgc   1080
tgggctgggt agataaaagt cagcagctat gaatactcta tgtgatgctc attggcgtgt   1140
acgttttaaa aaaaaaaaaa aaaaaaaaaa aaaaaaaaaa aaaaaaaaaa aaaaaaaaaa   1200
aaaaaaaaag ggggcggccg c                                            1221

<210> SEQ ID NO 2
<211> LENGTH: 951
<212> TYPE: DNA
<213> ORGANISM: Trichoderma reesei

<400> SEQUENCE: 2
atggttcgcc ggactgctct gctggccctt ggggctctct caacgctctc tatggcccaa    60
atctcagacg acttcgagtc gggctgggat cagactaaat ggcccatttc ggcaccagac   120
tgtaaccagg gcggcaccgt cagcctcgac accacagtag cccacagcgg cagcaactcc   180
atgaaggtcg ttggtggccc caatggctac tgtggacaca tcttcttcgg cactacccag   240
gtgccaactg gggatgtata tgtcagagct tggattcggc ttcagactgc tctcggcagc   300
aaccacgtca cattcatcat catgccagac accgctcagg gagggaagca cctccgaatt   360
ggtggccaaa gccaagttct cgactacaac cgcgagtccg acgatgccac tcttccggac   420
ctgtctccca acggcattgc ctccaccgtc actctgccta ccggcgcgtt ccagtgcttc   480
gagtaccacc tgggcactga cggaaccatc gagacgtggc tcaacggcag cctcatcccg   540
ggcatgaccg tgggccctgg cgtcgacaat ccaaacgacg ctggctggac gagggccagc   600
tatattccgg agatcaccgg tgtcaacttt ggctggagg cctacagcgg agacgtcaac   660
accgtctggt tcgacgacat ctcgattgcg tcgacccgcg tgggatgcgg ccccggcagc   720
cccggcggtc ctggaagctc gacgactggg cgtagcagca cctcgggccc gacgagcact   780
tcgaggccaa gcaccaccat tccgccaccg acttccagga caacgacgc cacgggtccg   840 actcagacac actatggcca gtgcggaggg attggttaca gcgggcctac ggtctgcgcg   900
agcggcacga cctgccaggt cctgaaccca tactactccc agtgcttata a            951

<210> SEQ ID NO 3
<211> LENGTH: 316
<212> TYPE: PRT
<213> ORGANISM: Trichoderma reesei

<400> SEQUENCE: 3

Met Val Arg Arg Thr Ala Leu Leu Ala Leu Gly Ala Leu Ser Thr Leu
 1               5                  10                  15

Ser Met Ala Gln Ile Ser Asp Asp Phe Glu Ser Gly Trp Asp Gln Thr
             20                  25                  30
```

```
Lys Trp Pro Ile Ser Ala Pro Asp Cys Asn Gln Gly Gly Thr Val Ser
             35                  40                  45

Leu Asp Thr Thr Val Ala His Ser Gly Ser Asn Ser Met Lys Val Val
 50                  55                  60

Gly Gly Pro Asn Gly Tyr Cys Gly His Ile Phe Phe Gly Thr Thr Gln
 65                  70                  75                  80

Val Pro Thr Gly Asp Val Tyr Val Arg Ala Trp Ile Arg Leu Gln Thr
                 85                  90                  95

Ala Leu Gly Ser Asn His Val Thr Phe Ile Ile Met Pro Asp Thr Ala
            100                 105                 110

Gln Gly Gly Lys His Leu Arg Ile Gly Gly Gln Ser Gln Val Leu Asp
            115                 120                 125

Tyr Asn Arg Glu Ser Asp Ala Thr Leu Pro Asp Leu Ser Pro Asn
130                 135                 140

Gly Ile Ala Ser Thr Val Thr Leu Pro Thr Gly Ala Phe Gln Cys Phe
145                 150                 155                 160

Glu Tyr His Leu Gly Thr Asp Gly Thr Ile Glu Thr Trp Leu Asn Gly
                165                 170                 175

Ser Leu Ile Pro Gly Met Thr Val Gly Pro Gly Val Asp Pro Asn
            180                 185                 190

Asp Ala Gly Trp Thr Arg Ala Ser Tyr Ile Pro Glu Ile Thr Gly Val
            195                 200                 205

Asn Phe Gly Trp Glu Ala Tyr Ser Gly Asp Val Asn Thr Val Trp Phe
            210                 215                 220

Asp Asp Ile Ser Ile Ala Ser Thr Arg Val Gly Cys Gly Pro Gly Ser
225                 230                 235                 240

Pro Gly Gly Pro Gly Ser Ser Thr Gly Arg Ser Ser Thr Ser Gly
                245                 250                 255

Pro Thr Ser Thr Ser Arg Pro Ser Thr Thr Ile Pro Pro Pro Thr Ser
                260                 265                 270

Arg Thr Thr Thr Ala Thr Gly Pro Thr Gln Thr His Tyr Gly Gln Cys
            275                 280                 285

Gly Gly Ile Gly Tyr Ser Gly Pro Thr Val Cys Ala Ser Gly Thr Thr
            290                 295                 300

Cys Gln Val Leu Asn Pro Tyr Tyr Ser Gln Cys Leu
305                 310                 315

<210> SEQ ID NO 4
<211> LENGTH: 19
<212> TYPE: PRT
<213> ORGANISM: Trichoderma reesei

<400> SEQUENCE: 4

Met Val Arg Arg Thr Ala Leu Leu Ala Leu Gly Ala Leu Ser Thr Leu
 1               5                  10                  15

Ser Met Ala

<210> SEQ ID NO 5
<211> LENGTH: 297
<212> TYPE: PRT
<213> ORGANISM: Trichoderma reesei

<400> SEQUENCE: 5

Gln Ile Ser Asp Asp Phe Glu Ser Gly Trp Asp Gln Thr Lys Trp Pro
 1               5                  10                  15

Ile Ser Ala Pro Asp Cys Asn Gln Gly Gly Thr Val Ser Leu Asp Thr
```

```
                20                  25                  30
Thr Val Ala His Ser Gly Ser Asn Ser Met Lys Val Val Gly Gly Pro
             35                  40                  45

Asn Gly Tyr Cys Gly His Ile Phe Phe Gly Thr Thr Gln Val Pro Thr
     50                  55                  60

Gly Asp Val Tyr Val Arg Ala Trp Ile Arg Leu Gln Thr Ala Leu Gly
 65                  70                  75                  80

Ser Asn His Val Thr Phe Ile Ile Met Pro Asp Thr Ala Gln Gly Gly
                 85                  90                  95

Lys His Leu Arg Ile Gly Gly Gln Ser Gln Val Leu Asp Tyr Asn Arg
            100                 105                 110

Glu Ser Asp Asp Ala Thr Leu Pro Asp Leu Ser Pro Asn Gly Ile Ala
        115                 120                 125

Ser Thr Val Thr Leu Pro Thr Gly Ala Phe Gln Cys Phe Glu Tyr His
    130                 135                 140

Leu Gly Thr Asp Gly Thr Ile Glu Thr Trp Leu Asn Gly Ser Leu Ile
145                 150                 155                 160

Pro Gly Met Thr Val Gly Pro Gly Val Asp Asn Pro Asn Asp Ala Gly
                165                 170                 175

Trp Thr Arg Ala Ser Tyr Ile Pro Glu Ile Thr Gly Val Asn Phe Gly
            180                 185                 190

Trp Glu Ala Tyr Ser Gly Asp Val Asn Thr Val Trp Phe Asp Asp Ile
        195                 200                 205

Ser Ile Ala Ser Thr Arg Val Gly Cys Gly Pro Gly Ser Pro Gly Gly
    210                 215                 220

Pro Gly Ser Ser Thr Gly Arg Ser Ser Thr Ser Gly Pro Thr Ser
225                 230                 235                 240

Thr Ser Arg Pro Ser Thr Ile Pro Pro Pro Thr Ser Arg Thr Thr
                245                 250                 255

Thr Ala Thr Gly Pro Thr Gln Thr His Tyr Gly Gln Cys Gly Gly Ile
            260                 265                 270

Gly Tyr Ser Gly Pro Thr Val Cys Ala Ser Gly Thr Thr Cys Gln Val
        275                 280                 285

Leu Asn Pro Tyr Tyr Ser Gln Cys Leu
    290                 295
```

<210> SEQ ID NO 6
<211> LENGTH: 1383
<212> TYPE: DNA
<213> ORGANISM: Trichoderma reesei

<400> SEQUENCE: 6

```
atggcttccc gcttctttgc tcttctcctt ttagcgatcc caatccaggc ccaatctcca      60
gtctggggac aatgtggtgg aattggttgg tctggcccaa caacttgtgt tggaggtgcg     120
acttgtgtat catataaccc ttattactcg aatgtattc ccagtacaca ggcttcatcg      180
agcatagcct ctacaacgct ggtcacatca tttacgacca ccactgctac gaggacttcg     240
gcatcaacgc ctccagcgag cagtacaggt gcaggcggcg aacatgctc agcactgccg      300 ggctccatta ccctgagatc caacgcaaag ctcaacgatc tgtttacaat gttcaatgga     360
gataaggtca ccacgaaaga caattctctg tgccgccagg cagagatgtc ggagctaata     420
caacgatatg agctcggcac cctgcccgga cgaccaagca ctctcacagc ctcattctcg     480
ggcaatacgt tgaccatcaa ttgcggagag gccgaaaagt caatttcatt cacagtcacg     540
atcacttatc catcttccgg aacagcacca tacctgcga ttatcggcta tggaggcggc      600
```

```
agtcttccag ctcccgccgg ggttgccatg atcaacttta acaatgacaa catagcagcc      660
caagttaata caggcagccg cggacagggc aagttctacg atctctacgg gagctcgcac      720
tccgcgggcg ccatgaccgc atgggcctgg ggagtaagcc gagtcattga tgctcttgag      780
cttgtaccag gcgcaagaat agacaccacc aagattggcg tgacggggtg ttcacgaaat      840
ggcaaaggcg caatggtcgc aggtgctttc gagaaacgaa tcgttctgac acttccccag      900
gagtcgggcg ccggtggctc tgcgtgctgg aggatttcag actacttaaa gtcccaagga      960
gccaatatcc agaccgcgtc tgagatcatt ggcgaagacc cctggttctc gactactttc     1020
aacagctacg tcaaccaagt gccggtgttg ccgtttgacc accattcgct tgctgccttg     1080
atagccccga gaggattatt cgtcatcgac aacaatattg actggctcgg cccacaaagc     1140
tgctttggct gtatgacagc tgctcacatg gcatggcaag ctttgggtgt ctcggaccac     1200
atgggctatt cgcagattgg agctcacgca cactgcgcgt tcccatcaaa ccagcaatcg     1260
caacttactg cctttgttca gaaattcttg ctgggccagt ccacaaatac ggcgattttc     1320
caaagcgact tttcggccaa tcaaagccaa tggatcgact ggacaacccc aacgctgagt     1380
tga                                                                  1383
```

<210> SEQ ID NO 7
<211> LENGTH: 460
<212> TYPE: PRT
<213> ORGANISM: Trichoderma reesei

<400> SEQUENCE: 7

```
Met Ala Ser Arg Phe Phe Ala Leu Leu Leu Ala Ile Pro Ile Gln
 1               5                  10                  15

Ala Gln Ser Pro Val Trp Gly Gln Cys Gly Gly Ile Gly Trp Ser Gly
             20                  25                  30

Pro Thr Thr Cys Val Gly Gly Ala Thr Cys Val Ser Tyr Asn Pro Tyr
         35                  40                  45

Tyr Ser Gln Cys Ile Pro Ser Thr Gln Ala Ser Ser Ile Ala Ser
     50                  55                  60

Thr Thr Leu Val Thr Ser Phe Thr Thr Thr Ala Thr Arg Thr Ser
 65                  70                  75                  80

Ala Ser Thr Pro Pro Ala Ser Ser Thr Gly Ala Gly Gly Ala Thr Cys
                 85                  90                  95

Ser Ala Leu Pro Gly Ser Ile Thr Leu Arg Ser Asn Ala Lys Leu Asn
            100                 105                 110

Asp Leu Phe Thr Met Phe Asn Gly Asp Lys Val Thr Thr Lys Asp Lys
        115                 120                 125

Phe Ser Cys Arg Gln Ala Glu Met Ser Glu Leu Ile Gln Arg Tyr Glu
    130                 135                 140

Leu Gly Thr Leu Pro Gly Arg Pro Ser Thr Leu Thr Ala Ser Phe Ser
145                 150                 155                 160

Gly Asn Thr Leu Thr Ile Asn Cys Gly Glu Ala Gly Lys Ser Ile Ser
                165                 170                 175

Phe Thr Val Thr Ile Thr Tyr Pro Ser Ser Gly Thr Ala Pro Tyr Pro
            180                 185                 190

Ala Ile Ile Gly Tyr Gly Gly Gly Ser Leu Pro Ala Pro Ala Gly Val
        195                 200                 205

Ala Met Ile Asn Phe Asn Asn Asp Asn Ile Ala Ala Gln Val Asn Thr
    210                 215                 220

Gly Ser Arg Gly Gln Gly Lys Phe Tyr Asp Leu Tyr Gly Ser Ser His
```

```
                225                 230                 235                 240
Ser Ala Gly Ala Met Thr Ala Trp Ala Trp Gly Val Ser Arg Val Ile
            245                 250                 255

Asp Ala Leu Glu Leu Val Pro Gly Ala Arg Ile Asp Thr Thr Lys Ile
        260                 265                 270

Gly Val Thr Gly Cys Ser Arg Asn Gly Lys Gly Ala Met Val Ala Gly
    275                 280                 285

Ala Phe Glu Lys Arg Ile Val Leu Thr Leu Pro Gln Glu Ser Gly Ala
290                 295                 300

Gly Gly Ser Ala Cys Trp Arg Ile Ser Asp Tyr Leu Lys Ser Gln Gly
305                 310                 315                 320

Ala Asn Ile Gln Thr Ala Ser Glu Ile Ile Gly Glu Asp Pro Trp Phe
                325                 330                 335

Ser Thr Thr Phe Asn Ser Tyr Val Asn Gln Val Pro Val Leu Pro Phe
            340                 345                 350

Asp His His Ser Leu Ala Ala Leu Ile Ala Pro Arg Gly Leu Phe Val
        355                 360                 365

Ile Asp Asn Asn Ile Asp Trp Leu Gly Pro Gln Ser Cys Phe Gly Cys
    370                 375                 380

Met Thr Ala Ala His Met Ala Trp Gln Ala Leu Gly Val Ser Asp His
385                 390                 395                 400

Met Gly Tyr Ser Gln Ile Gly Ala His Ala His Cys Ala Phe Pro Ser
                405                 410                 415

Asn Gln Gln Ser Gln Leu Thr Ala Phe Val Gln Lys Phe Leu Leu Gly
            420                 425                 430

Gln Ser Thr Asn Thr Ala Ile Phe Gln Ser Asp Phe Ser Ala Asn Gln
        435                 440                 445

Ser Gln Trp Ile Asp Trp Thr Thr Pro Thr Leu Ser
    450                 455                 460

<210> SEQ ID NO 8
<211> LENGTH: 17
<212> TYPE: PRT
<213> ORGANISM: Trichoderma reesei

<400> SEQUENCE: 8

Met Ala Ser Arg Phe Phe Ala Leu Leu Leu Ala Ile Pro Ile Gln
1               5                   10                  15

Ala

<210> SEQ ID NO 9
<211> LENGTH: 443
<212> TYPE: PRT
<213> ORGANISM: Trichoderma reesei

<400> SEQUENCE: 9

Gln Ser Pro Val Trp Gly Gln Cys Gly Gly Ile Gly Trp Ser Gly Pro
1               5                   10                  15

Thr Thr Cys Val Gly Gly Ala Thr Cys Val Ser Tyr Asn Pro Tyr Tyr
            20                  25                  30

Ser Gln Cys Ile Pro Ser Thr Gln Ala Ser Ser Ile Ala Ser Thr
        35                  40                  45

Thr Leu Val Thr Ser Phe Thr Thr Thr Ala Thr Arg Thr Ser Ala
    50                  55                  60

Ser Thr Pro Pro Ala Ser Ser Thr Gly Ala Gly Gly Ala Thr Cys Ser
65                  70                  75                  80
```

```
Ala Leu Pro Gly Ser Ile Thr Leu Arg Ser Asn Ala Lys Leu Asn Asp
                 85                  90                  95

Leu Phe Thr Met Phe Asn Gly Asp Lys Val Thr Lys Asp Lys Phe
            100                 105                 110

Ser Cys Arg Gln Ala Glu Met Ser Glu Leu Ile Gln Arg Tyr Glu Leu
        115                 120                 125

Gly Thr Leu Pro Gly Arg Pro Ser Thr Leu Thr Ala Ser Phe Ser Gly
        130                 135                 140

Asn Thr Leu Thr Ile Asn Cys Gly Glu Ala Gly Lys Ser Ile Ser Phe
145                 150                 155                 160

Thr Val Thr Ile Thr Tyr Pro Ser Ser Gly Thr Ala Pro Tyr Pro Ala
                165                 170                 175

Ile Ile Gly Tyr Gly Gly Gly Ser Leu Pro Ala Pro Ala Gly Val Ala
                180                 185                 190

Met Ile Asn Phe Asn Asn Asp Asn Ile Ala Ala Gln Val Asn Thr Gly
            195                 200                 205

Ser Arg Gly Gln Gly Lys Phe Tyr Asp Leu Tyr Gly Ser Ser His Ser
        210                 215                 220

Ala Gly Ala Met Thr Ala Trp Ala Trp Gly Val Ser Arg Val Ile Asp
225                 230                 235                 240

Ala Leu Glu Leu Val Pro Gly Ala Arg Ile Asp Thr Thr Lys Ile Gly
                245                 250                 255

Val Thr Gly Cys Ser Arg Asn Gly Lys Gly Ala Met Val Ala Gly Ala
            260                 265                 270

Phe Glu Lys Arg Ile Val Leu Thr Leu Pro Gln Glu Ser Gly Ala Gly
        275                 280                 285

Gly Ser Ala Cys Trp Arg Ile Ser Asp Tyr Leu Lys Ser Gln Gly Ala
290                 295                 300

Asn Ile Gln Thr Ala Ser Glu Ile Ile Gly Glu Asp Pro Trp Phe Ser
305                 310                 315                 320

Thr Thr Phe Asn Ser Tyr Val Asn Gln Val Pro Val Leu Pro Phe Asp
                325                 330                 335

His His Ser Leu Ala Ala Leu Ile Ala Pro Arg Gly Leu Phe Val Ile
            340                 345                 350

Asp Asn Asn Ile Asp Trp Leu Gly Pro Gln Ser Cys Phe Gly Cys Met
        355                 360                 365

Thr Ala Ala His Met Ala Trp Gln Ala Leu Gly Val Ser Asp His Met
370                 375                 380

Gly Tyr Ser Gln Ile Gly Ala His Ala His Cys Ala Phe Pro Ser Asn
385                 390                 395                 400

Gln Gln Ser Gln Leu Thr Ala Phe Val Gln Lys Phe Leu Leu Gly Gln
                405                 410                 415

Ser Thr Asn Thr Ala Ile Phe Gln Ser Asp Phe Ser Ala Asn Gln Ser
            420                 425                 430

Gln Trp Ile Asp Trp Thr Thr Pro Thr Leu Ser
        435                 440

<210> SEQ ID NO 10
<211> LENGTH: 966
<212> TYPE: DNA
<213> ORGANISM: Trichoderma reesei

<400> SEQUENCE: 10
atggagctta aagcactcag tgccgttgtg ctgagctttg taactcttgt cgcggcagca    60
ccggcgacct gcacgcttcc gtccacatac cgctggaatt cgaccggtgc tttagccagc   120
```

```
ccgaaatcag gctgggtctc gctgaaagac ttctcccatg tcatttataa tggccagcat    180
cttgtatggg gctcgactca tgacacagga acaatctggg gttcaatgaa ctttggtctg    240
ttcagtgact ggtccaatat ggcaacggca agccagaaca aaatgactcc cggcactgtt    300
gctcctaccg tcttctactt tgccccgaag aatatttggg tactcgccta tcaatggggc    360
ccgaccacgt tttcctacct gacgtcaagc aaccccccca gcgtcaatgg atggtcgtca    420
ccacagcctc tcttctccgg cagtatctca ggctccagcc cgctggatca gacggtcatt    480
ggcgacagca cgaacatgta tctgttcttc gcggggacg acgggaaaat ctacagggcg    540
agcatgccta tcggtaactt ccccggaagc ttcggttcga cgtcaacggt ggtcctgagc    600
gatgaaagga caatctgtt tgaggcagtt caggtctata ccgtctcagg cagaagcaa     660 tatctcatga ttgtcgaggc aataggcgca atggccggt atttccggtc cttcacagcg    720
acaaacctcg gcggcacatg gactccgcaa gccaccagcg aaagtcagcc gtttgccggt    780
aaggcaaaca gtggcgctac ctggacaaac gacatcagtc atggtgatct aattcgtagc    840
aaccctgatc agacaatgac tatcgaccct gcaatctgc agttcttgta ccaggggaga    900
gcgacaaact ctggcggcga ctacggcctc ttgccctatc gaccagggct gctaactctc    960
cagcgc                                                              966
```

<210> SEQ ID NO 11
<211> LENGTH: 322
<212> TYPE: PRT
<213> ORGANISM: Trichoderma reesei

<400> SEQUENCE: 11

```
Met Glu Leu Lys Ala Leu Ser Ala Val Val Leu Ser Phe Val Thr Leu
  1               5                  10                  15

Val Ala Ala Pro Ala Thr Cys Thr Leu Pro Ser Thr Tyr Arg Trp
             20                  25                  30

Asn Ser Thr Gly Ala Leu Ala Ser Pro Lys Ser Gly Trp Val Ser Leu
         35                  40                  45

Lys Asp Phe Ser His Val Ile Tyr Asn Gly Gln His Leu Val Trp Gly
     50                  55                  60

Ser Thr His Asp Thr Gly Thr Ile Trp Gly Ser Met Asn Phe Gly Leu
 65                  70                  75                  80

Phe Ser Asp Trp Ser Asn Met Ala Thr Ala Ser Gln Asn Lys Met Thr
                 85                  90                  95

Pro Gly Thr Val Ala Pro Thr Val Phe Tyr Phe Ala Pro Lys Asn Ile
            100                 105                 110

Trp Val Leu Ala Tyr Gln Trp Gly Pro Thr Thr Phe Ser Tyr Leu Thr
        115                 120                 125

Ser Ser Asn Pro Ser Ser Val Asn Gly Trp Ser Ser Pro Gln Pro Leu
    130                 135                 140

Phe Ser Gly Ser Ile Ser Gly Ser Ser Pro Leu Asp Gln Thr Val Ile
145                 150                 155                 160

Gly Asp Ser Thr Asn Met Tyr Leu Phe Phe Ala Gly Asp Gly Lys
                165                 170                 175

Ile Tyr Arg Ala Ser Met Pro Ile Gly Asn Phe Pro Gly Ser Phe Gly
            180                 185                 190

Ser Thr Ser Thr Val Val Leu Ser Asp Glu Arg Asn Asn Leu Phe Glu
        195                 200                 205

Ala Val Gln Val Tyr Thr Val Ser Gly Gln Lys Gln Tyr Leu Met Ile
    210                 215                 220
```

-continued

Val Glu Ala Ile Gly Ala Asn Gly Arg Tyr Phe Arg Ser Phe Thr Ala
225                 230                 235                 240

Thr Asn Leu Gly Gly Thr Trp Thr Pro Gln Ala Thr Ser Glu Ser Gln
            245                 250                 255

Pro Phe Ala Gly Lys Ala Asn Ser Gly Ala Thr Trp Thr Asn Asp Ile
        260                 265                 270

Ser His Gly Asp Leu Ile Arg Ser Asn Pro Asp Gln Thr Met Thr Ile
    275                 280                 285

Asp Pro Cys Asn Leu Gln Phe Leu Tyr Gln Gly Arg Ala Thr Asn Ser
290                 295                 300

Gly Gly Asp Tyr Gly Leu Leu Pro Tyr Arg Pro Gly Leu Leu Thr Leu
305                 310                 315                 320

Gln Arg

<210> SEQ ID NO 12
<211> LENGTH: 19
<212> TYPE: PRT
<213> ORGANISM: Trichoderma reesei

<400> SEQUENCE: 12

Met Glu Leu Lys Ala Leu Ser Ala Val Val Leu Ser Phe Val Thr Leu
1               5                   10                  15

Val Ala Ala

<210> SEQ ID NO 13
<211> LENGTH: 303
<212> TYPE: PRT
<213> ORGANISM: Trichoderma reesei

<400> SEQUENCE: 13

Ala Pro Ala Thr Cys Thr Leu Pro Ser Thr Tyr Arg Trp Asn Ser Thr
1               5                   10                  15

Gly Ala Leu Ala Ser Pro Lys Ser Gly Trp Val Ser Leu Lys Asp Phe
            20                  25                  30

Ser His Val Ile Tyr Asn Gly Gln His Leu Val Trp Gly Ser Thr His
        35                  40                  45

Asp Thr Gly Thr Ile Trp Gly Ser Met Asn Phe Gly Leu Phe Ser Asp
    50                  55                  60

Trp Ser Asn Met Ala Thr Ala Ser Gln Asn Lys Met Thr Pro Gly Thr
65                  70                  75                  80

Val Ala Pro Thr Val Phe Tyr Phe Ala Pro Lys Asn Ile Trp Val Leu
                85                  90                  95

Ala Tyr Gln Trp Gly Pro Thr Thr Phe Ser Tyr Leu Thr Ser Ser Asn
            100                 105                 110

Pro Ser Ser Val Asn Gly Trp Ser Pro Gln Pro Leu Phe Ser Gly
        115                 120                 125

Ser Ile Ser Gly Ser Ser Pro Leu Asp Gln Thr Val Ile Gly Asp Ser
    130                 135                 140

Thr Asn Met Tyr Leu Phe Phe Ala Gly Asp Asp Gly Lys Ile Tyr Arg
145                 150                 155                 160

Ala Ser Met Pro Ile Gly Asn Phe Pro Gly Ser Phe Gly Ser Thr Ser
                165                 170                 175

Thr Val Val Leu Ser Asp Glu Arg Asn Asn Leu Phe Glu Ala Val Gln
            180                 185                 190

Val Tyr Thr Val Ser Gly Gln Lys Gln Tyr Leu Met Ile Val Glu Ala
        195                 200                 205

```
Ile Gly Ala Asn Gly Arg Tyr Phe Arg Ser Phe Thr Ala Thr Asn Leu
    210                 215                 220
Gly Gly Thr Trp Thr Pro Gln Ala Thr Ser Glu Ser Gln Pro Phe Ala
225                 230                 235                 240
Gly Lys Ala Asn Ser Gly Ala Thr Trp Thr Asn Asp Ile Ser His Gly
                245                 250                 255
Asp Leu Ile Arg Ser Asn Pro Asp Gln Thr Met Thr Ile Asp Pro Cys
            260                 265                 270
Asn Leu Gln Phe Leu Tyr Gln Gly Arg Ala Thr Asn Ser Gly Gly Asp
        275                 280                 285
Tyr Gly Leu Leu Pro Tyr Arg Pro Gly Leu Leu Thr Leu Gln Arg
    290                 295                 300
```

<210> SEQ ID NO 14
<211> LENGTH: 900
<212> TYPE: DNA
<213> ORGANISM: Trichoderma reesei

<400> SEQUENCE: 14

```
atgcgcgccc tctcactctc cctccccctc tccctctcgc tgctcgccgc cagctcaaca      60
gcggcaacga catgcgcaaa gggcctctac atggtcgttg cccgcggcag cgaggagccc     120
gccggcacgg gcgtgacggg caacctcacg agccaaatcg ccgcaaaggt gcccggcagc     180
gaggtcgtgg cggtggacta cccggccagc tttgacgact acgaggattc cgagggcgac     240
ggcgtcaagg cgatgcggca gctgctcaac agctacgccg aggcctgtcc gggaaacaag     300
attgcggtgc tgggatactc tcagggcgcc caagtcgcaa cagacaccat ctgcggcggt     360
gccggcgatc cgtttaccag cgacaagggc atgtctgacg atgtcatgga cgacgtcgtt     420
gccgtggcca ttttcggaga cccaaccat gtcgccaaca tgacgtacga ccgaggcacc      480
agcattcaca acgggctctt caaccggagc tcgtccagca tcgaggtctg caagtcgtac     540
gccagccgca tcgtctcgta ctgcgacacg ggcgacatct actgcgacgc cggcagcaac     600
tcgaccgttc accacatgta catccagcgc tacggcgacg aaatcgtcga ctttgtcgtc     660
agccagtttg agaagagcac cagctcggga tcggggtcgg gtactaatgc caccacgacc     720
acggctccgg ctcccaccgt gtctcctacc accaccagcg gtggcaacag cacagtgcct     780
acgcgaaccg gtggcccgac gacgagttcg acgcaaggat cgggtgcgag tgctttgacg     840
agcagtttga tgctgggagg tcttttgacg gttttgacgg cggtgtctca gatgctgtga     900
```

<210> SEQ ID NO 15
<211> LENGTH: 299
<212> TYPE: PRT
<213> ORGANISM: Trichoderma reesei

<400> SEQUENCE: 15

```
Met Arg Ala Leu Ser Leu Ser Leu Pro Leu Ser Leu Ser Leu Leu Ala
  1               5                  10                  15
Ala Ser Ser Thr Ala Ala Thr Thr Cys Ala Lys Gly Leu Tyr Met Val
                20                  25                  30
Val Ala Arg Gly Ser Glu Glu Pro Ala Gly Thr Gly Val Thr Gly Asn
            35                  40                  45
Leu Thr Ser Gln Ile Ala Ala Lys Val Pro Gly Ser Glu Val Val Ala
        50                  55                  60
Val Asp Tyr Pro Ala Ser Phe Asp Asp Tyr Glu Asp Ser Glu Gly Asp
65                  70                  75                  80
```

-continued

```
Gly Val Lys Ala Met Arg Gln Leu Leu Asn Ser Tyr Ala Glu Ala Cys
                85                  90                  95

Pro Gly Asn Lys Ile Ala Val Leu Gly Tyr Ser Gln Gly Ala Gln Val
            100                 105                 110

Ala Thr Asp Thr Ile Cys Gly Gly Ala Gly Asp Pro Phe Thr Ser Asp
        115                 120                 125

Lys Gly Met Ser Asp Asp Val Met Asp Val Val Ala Val Ala Ile
    130                 135                 140

Phe Gly Asp Pro Thr His Val Ala Asn Met Thr Tyr Asp Arg Gly Thr
145                 150                 155                 160

Ser Ile His Asn Gly Leu Phe Asn Arg Ser Ser Ser Ile Glu Val
                165                 170                 175

Cys Lys Ser Tyr Ala Ser Arg Ile Val Ser Tyr Cys Asp Thr Gly Asp
            180                 185                 190

Ile Tyr Cys Asp Ala Gly Ser Asn Ser Thr Val His His Met Tyr Ile
        195                 200                 205

Gln Arg Tyr Gly Asp Glu Ile Val Asp Phe Val Ser Gln Phe Glu
    210                 215                 220

Lys Ser Thr Ser Ser Gly Ser Gly Ser Gly Thr Asn Ala Thr Thr Thr
225                 230                 235                 240

Thr Ala Pro Ala Pro Thr Val Ser Pro Thr Thr Thr Ser Gly Gly Asn
                245                 250                 255

Ser Thr Val Pro Thr Arg Thr Gly Gly Pro Thr Thr Ser Ser Thr Gln
            260                 265                 270

Gly Ser Gly Ala Ser Ala Leu Thr Ser Ser Leu Met Leu Gly Gly Leu
        275                 280                 285

Leu Thr Val Leu Thr Ala Val Ser Gln Met Leu
    290                 295

<210> SEQ ID NO 16
<211> LENGTH: 21
<212> TYPE: PRT
<213> ORGANISM: Trichoderma reesei

<400> SEQUENCE: 16

Met Arg Ala Leu Ser Leu Ser Leu Pro Leu Ser Leu Ser Leu Leu Ala
1               5                   10                  15

Ala Ser Ser Thr Ala
            20

<210> SEQ ID NO 17
<211> LENGTH: 278
<212> TYPE: PRT
<213> ORGANISM: Trichoderma reesei

<400> SEQUENCE: 17

Ala Thr Thr Cys Ala Lys Gly Leu Tyr Met Val Val Ala Arg Gly Ser
1               5                   10                  15

Glu Glu Pro Ala Gly Thr Gly Val Thr Gly Asn Leu Thr Ser Gln Ile
            20                  25                  30

Ala Ala Lys Val Pro Gly Ser Glu Val Val Ala Val Asp Tyr Pro Ala
        35                  40                  45

Ser Phe Asp Asp Tyr Glu Asp Ser Glu Gly Asp Gly Val Lys Ala Met
    50                  55                  60

Arg Gln Leu Leu Asn Ser Tyr Ala Glu Ala Cys Pro Gly Asn Lys Ile
65                  70                  75                  80

Ala Val Leu Gly Tyr Ser Gln Gly Ala Gln Val Ala Thr Asp Thr Ile
```

```
                85                  90                  95
Cys Gly Gly Ala Gly Asp Pro Phe Thr Ser Asp Lys Gly Met Ser Asp
            100                 105                 110

Asp Val Met Asp Val Val Ala Val Ala Ile Phe Gly Asp Pro Ser Thr
        115                 120                 125

His Val Ala Asn Met Thr Tyr Asp Arg Gly Thr Ser Ile His Asn Gly
    130                 135                 140

Leu Phe Asn Arg Ser Ser Ser Ile Glu Val Cys Lys Ser Tyr Ala
145                 150                 155                 160

Ser Arg Ile Val Ser Tyr Cys Asp Thr Gly Asp Ile Tyr Cys Asp Ala
                165                 170                 175

Gly Ser Asn Ser Thr Val His His Met Tyr Ile Gln Arg Tyr Gly Asp
            180                 185                 190

Glu Ile Val Asp Phe Val Val Ser Gln Phe Glu Lys Ser Thr Ser Ser
        195                 200                 205

Gly Ser Gly Ser Gly Thr Asn Ala Thr Thr Thr Ala Pro Ala Pro
    210                 215                 220

Thr Val Ser Pro Thr Thr Thr Ser Gly Gly Asn Ser Thr Val Pro Thr
225                 230                 235                 240

Arg Thr Gly Gly Pro Thr Thr Ser Ser Thr Gln Ser Gly Ala Ser
                245                 250                 255

Ala Leu Thr Ser Ser Leu Met Leu Gly Gly Leu Leu Thr Val Leu Thr
            260                 265                 270

Ala Val Ser Gln Met Leu
        275

<210> SEQ ID NO 18
<211> LENGTH: 768
<212> TYPE: PRT
<213> ORGANISM: Ruminococcus flavefaciens

<400> SEQUENCE: 18

Met Lys Lys His Phe Val Val Gly Glu Thr Ile Lys Arg Phe Leu Arg
1               5                   10                  15

Ile Gly Thr Ser Leu Ala Leu Ser Ile Ser Thr Leu Ser Leu Leu Pro
            20                  25                  30

Ser Ala Pro Arg Leu Ser Ser Ala Ala Gly Thr Ile Lys Ile Met Pro
        35                  40                  45

Leu Gly Asp Ser Ile Thr Tyr Gly Met Ala Asp Glu Gly Gly Tyr Arg
    50                  55                  60

Lys Tyr Leu Ser Tyr Phe Leu Gln Gln Lys Gly Tyr Thr Asn Val Asp
65                  70                  75                  80

Leu Val Gly Pro Glu Gly Lys Asp Ser Ala Ser Phe Asn Tyr Asn Gly
                85                  90                  95

Gln Ser Val Lys Tyr Asp Asp Asn His Ala Gly Tyr Ser Gly Tyr Thr
            100                 105                 110

Ile Thr Asn Leu Pro Gly Gly Trp Phe Gly Gln Leu Asn Gly Ile Leu
        115                 120                 125

Glu Thr Met Gln Gly Gly Asp Tyr Ile Lys Lys Tyr Ser Pro Asp Ile
    130                 135                 140

Ile Leu Leu Gln Ile Gly Thr Asn Asp Val Ser Asn Gly His Leu Asp
145                 150                 155                 160

Gly Ser Glu Glu Arg Leu His Lys Leu Leu Asp Tyr Leu Arg Glu Asn
                165                 170                 175

Met Pro Ser Asn Gly Lys Val Phe Leu Thr Thr Ile Pro Asp Leu Gly
```

-continued

```
                180                 185                 190
Asn Ser Gly Trp Gly Gly Asn Ser Asn Gly Asp Ile Ala Lys Tyr Asn
            195                 200                 205
Glu Leu Ile Lys Lys Val Ala Asn Asp Tyr Ser Ser Lys Asn Val Ile
            210                 215                 220
Tyr Ala Asp Ile His Ser Val Ile Asp Ala Ser Lys Asp Leu Ala Asp
225                 230                 235                 240
Gly Val His Pro Asn Ala Gly Tyr Glu Lys Met Gly Lys Tyr Trp
                245                 250                 255
Leu Glu Gln Ile Glu Gly Tyr Leu Lys Ala Ser Asp Gly Pro Gln Gln
            260                 265                 270
Thr Gln Pro Thr Gln Pro Ser Gln Gly Asp Ser Gly Pro Glu Leu Ile
            275                 280                 285
Tyr Gly Asp Leu Asp Gly Asp Lys Thr Ile Thr Ser Phe Asp Ala Val
            290                 295                 300
Ile Met Arg Lys Gly Leu Ile Asn Asp Phe Lys Asp Asn Asn Val Lys
305                 310                 315                 320
Lys Ala Ala Asp Ile Asp Gln Asn Gly Lys Ala Glu Val Ala Asp Leu
                325                 330                 335
Val Gln Leu Gln Ser Phe Ile Ile Gly Lys Ile Lys Glu Phe Thr Val
            340                 345                 350
Ala Glu Lys Thr Val Thr Glu Lys Pro Val Phe Glu Lys Ser Tyr Asn
            355                 360                 365
Phe Pro Ala Val Asn Gln Leu Lys Ser Lys Asp Ile Pro Asp Pro
370                 375                 380
Phe Ile Phe Met Asp Gly Ser Lys Val Glu Ser Thr Asp Asp Trp Trp
385                 390                 395                 400
Lys Arg Gln Ser Glu Ile Ser Cys Met Tyr Glu Tyr Met Tyr Gly
                405                 410                 415
Lys Trp Ile Asp Gly Ser Asp Asp Glu Thr Thr Tyr Ser Ile Ser Gly
            420                 425                 430
Asn Ser Met Thr Ile Asn Val Lys Arg Lys Ser Thr Gly Lys Thr Ala
            435                 440                 445
Ser Phe Lys Ala Val Ile Asn Leu Pro Lys Asn Val Arg His Glu Gly
450                 455                 460
Gly Ala Pro Val Ile Leu Gly Met His Lys Gly Ile Ser Glu Ser Thr
465                 470                 475                 480
Ala Thr Ser Asn Gly Tyr Ala Val Ile Thr Tyr Asp Ser Asp Gly Met
                485                 490                 495
Phe Ser Ala Pro Gly Thr Ala Gln Asp Asn Asn Gln His Lys Gly Ala
            500                 505                 510
Phe Tyr Asp Leu Tyr Pro Tyr Gly Arg Asn Trp Asp Glu Gln Thr Gly
            515                 520                 525
Asp Leu Met Ala Trp Ser Trp Gly Ile Ser Arg Ile Leu Asp Ala Leu
            530                 535                 540
Tyr Asn Gly Ala Ala Lys Glu Leu Asn Ile Asn Pro Asp Ser Ser Ile
545                 550                 555                 560
Val Thr Gly Val Ser Arg Tyr Gly Lys Ala Ala Ser Val Cys Gly Ala
                565                 570                 575
Phe Asp Thr Arg Ile Lys Met Cys Ala Pro Ser Cys Ser Gly Ala Gly
            580                 585                 590
Gly Leu Ala Leu Tyr Arg Tyr Ser Ser Val Gly Lys Thr Tyr Asp Phe
            595                 600                 605
```

Ser Ser Lys Gly Gly Ser Ser Ser Tyr Thr Tyr Lys Glu Asn Glu Pro
       610                 615                 620

Leu Gly Ser Leu Gln Ala Ser Gly Glu Gln Gly Trp Phe Asn Gly Arg
625                 630                 635                 640

Phe Met Glu Phe Arg Asn Ala Glu Gln Phe Pro Met Asp Gln His Met
                645                 650                 655

Leu Gly Ala Leu Cys Cys Asp Pro Asp Arg Tyr Leu Phe Ile Ile Gly
            660                 665                 670

Ser Cys Glu Ser Glu Asp Trp Val Asn Ala Pro Ser Val Trp Met Ala
                675                 680                 685

Tyr Leu Gly Met Lys His Val Trp Asp Tyr Val Gly Ile Ser Asp His
690                 695                 700

Leu Ala Ile Asn Ile His Lys Ser Gly His Ala Val Ile Ala Glu Asp
705                 710                 715                 720

Ile Glu Lys Met Val Gln Tyr Phe Asp Tyr His Val Tyr Gly Ile Gln
                725                 730                 735

Pro Lys Met Asn Leu Glu Glu Leu Gln Thr Ser Val Phe Ala Leu Pro
                740                 745                 750

Lys Asn Lys Asp Ser Phe Ala Asp Thr Phe Ala Ser Lys Trp Leu Tyr
            755                 760                 765

<210> SEQ ID NO 19
<211> LENGTH: 511
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(511)
<223> OTHER INFORMATION: Xaa = Any Amino Acid

<400> SEQUENCE: 19

Xaa Xaa Xaa Xaa Xaa Xaa Ala Xaa Leu Xaa Xaa Ala Xaa Xaa Xaa Gln
1               5                   10                  15

Xaa Xaa Xaa Pro Xaa Xaa Xaa Xaa Gly Xaa Xaa Gly Xaa Xaa Xaa Xaa
            20                  25                  30

Xaa Xaa Xaa Xaa Xaa Xaa Xaa Xaa Xaa Xaa Xaa Xaa Xaa Phe Xaa Ala
        35                  40                  45

Xaa Xaa Xaa Xaa Xaa Gly Xaa Xaa Xaa Xaa Xaa Xaa Asn Xaa Xaa
    50                  55                  60

Xaa Xaa Xaa Xaa Xaa Xaa Xaa Asn Ala Xaa Ala Xaa Ile Ala Xaa
65                  70                  75                  80

Xaa Xaa Xaa Leu Xaa Ser Phe Xaa Xaa Xaa Xaa Xaa Xaa Xaa Xaa Ser
                85                  90                  95

Xaa Ala Xaa Xaa Xaa Xaa Ser Xaa Xaa Xaa Xaa Xaa Xaa Xaa Ser Xaa
            100                 105                 110

Xaa Xaa Xaa Pro Ala Xaa Xaa Xaa Leu Lys Ser Xaa Xaa Xaa Ile Xaa
            115                 120                 125

Asp Xaa Phe Xaa Xaa Xaa Xaa Gly Xaa Lys Val Xaa Ser Xaa Asp Xaa
    130                 135                 140

Phe Xaa Xaa Arg Gln Ala Glu Ile Ser Xaa Leu Xaa Xaa Xaa Tyr Xaa
145                 150                 155                 160

Xaa Gly Xaa Xaa Xaa Xaa Xaa Xaa Xaa Xaa Xaa Xaa Thr Xaa Ser Xaa
                165                 170                 175

Ser Gly Asn Ser Leu Thr Ile Asn Xaa Xaa Xaa Xaa Xaa Xaa Gly Lys
            180                 185                 190

```
Ser Xaa Ser Phe Xaa Xaa Xaa Ile Xaa Xaa Pro Xaa Xaa Xaa Xaa
    195                 200                 205

Xaa Xaa Gly Xaa Xaa Xaa Xaa Ala Ile Xaa Xaa Xaa Xaa Xaa Xaa
    210                 215                 220

Ser Xaa Xaa Xaa Xaa Gly Xaa Ala Met Ile Xaa Phe Xaa Xaa Asp
225                 230                 235                 240

Xaa Ile Xaa Ala Xaa Xaa Xaa Thr Ala Xaa Xaa Xaa Xaa Xaa Xaa
            245                 250                 255

Gly Xaa Phe Tyr Asp Leu Tyr Xaa Xaa Xaa Xaa Xaa Xaa Xaa Xaa
            260                 265                 270

Xaa Gly Xaa Leu Xaa Ala Trp Ala Trp Gly Ile Ser Arg Ile Ile Asp
    275                 280                 285

Ala Leu Xaa Xaa Xaa Xaa Ala Xaa Xaa Ile Xaa Xaa Xaa Xaa Xaa
    290                 295                 300

Xaa Xaa Val Thr Gly Xaa Ser Arg Xaa Gly Lys Ala Ala Xaa Val Xaa
305                 310                 315                 320

Gly Ala Phe Asp Xaa Arg Ile Xaa Leu Xaa Xaa Pro Xaa Xaa Ser Gly
            325                 330                 335

Ala Gly Gly Xaa Ala Xaa Trp Arg Xaa Ser Xaa Xaa Lys Ser Xaa
            340                 345                 350

Xaa Xaa Xaa Xaa Xaa Xaa Ala Ser Xaa Xaa Xaa Xaa Xaa Xaa Xaa
            355                 360                 365

Xaa Xaa Xaa Xaa Xaa Xaa Xaa Gly Glu Xaa Xaa Trp Phe Xaa
    370                 375                 380

Xaa Xaa Phe Xaa Xaa Phe Xaa Asn Xaa Xaa Xaa Xaa Pro Xaa Asp
385                 390                 395                 400

Xaa His Xaa Leu Ala Ala Leu Xaa Xaa Xaa Xaa Xaa Phe Leu Xaa
            405                 410                 415

Xaa Xaa Xaa Xaa Xaa Xaa Xaa Asp Trp Leu Xaa Xaa Xaa Ser Xaa
            420                 425                 430

Phe Xaa Xaa Xaa Xaa Ala Xaa Xaa Xaa Xaa Trp Xaa Xaa Leu Gly Ile
            435                 440                 445

Ser Asp His Leu Ala Xaa Xaa Xaa Xaa Ala Xaa Xaa Xaa Xaa Xaa
            450                 455                 460

Xaa Xaa Xaa Xaa Xaa Xaa Xaa Xaa Xaa Xaa Xaa Xaa Xaa Xaa Phe
465                 470                 475                 480

Xaa Ile Xaa Xaa Xaa Xaa Asn Xaa Xaa Xaa Xaa Gln Ser Xaa Xaa Xaa
            485                 490                 495

Ala Xaa Xaa Xaa Asn Xaa Xaa Xaa Phe Xaa Xaa Xaa Xaa Xaa Ser
            500                 505                 510

<210> SEQ ID NO 20
<211> LENGTH: 322
<212> TYPE: PRT
<213> ORGANISM: Cochliobolus carbonum

<400> SEQUENCE: 20

Met Arg Phe Val Pro Asp Leu Ser Phe Ser Ala Ala Val Ala Leu
1               5                   10                  15

Leu Ala Ser Thr Ala Ser Ala Gln Ser Cys Lys Leu Pro Thr Ser Tyr
            20                  25                  30

Lys Trp Thr Ser Ser Gly Ala Leu Ala Gln Pro Lys Ser Gly Trp Ala
            35                  40                  45

Asn Leu Lys Asp Phe Thr Ile Ser Ser Leu Asn Gly Lys His Ile Val
50                  55                  60
```

```
Tyr Ala Thr Asp His Asp Thr Gly Ser Lys Tyr Gly Ser Met Ala Phe
 65                  70                  75                  80

Ser Pro Phe Gly Ser Phe Ser Glu Met Ala Ser Ala Ser Gln Thr Ala
                 85                  90                  95

Thr Pro Phe Thr Ala Val Ala Pro Thr Leu Phe Arg Phe Ala Pro Lys
            100                 105                 110

Asn Ile Trp Val Leu Ala Tyr Gln Trp Gly Pro Thr Thr Phe Ser Tyr
        115                 120                 125

Arg Thr Ser Ser Asp Pro Thr Asn Pro Asn Ser Trp Gly Gly Val Gln
    130                 135                 140

Thr Leu Phe Ser Gly Lys Ile Ser Gly Ser Thr Gly Ala Ile Asp
145                 150                 155                 160

Gln Thr Val Ile Gly Asp Ala Ile Asn Met Tyr Leu Phe Phe Ala Gly
                165                 170                 175

Asp Asn Gly Lys Ile Tyr Arg Ser Ser Met Pro Lys Ala Asn Phe Pro
            180                 185                 190

Gly Ser Phe Gly Thr Ala Ser Thr Val Ile Met Ser Asp Ser Thr Asn
        195                 200                 205

Asn Leu Phe Glu Ala Val Gln Val Tyr Thr Val Lys Gly Gly Gly Tyr
    210                 215                 220

Leu Met Ile Val Glu Ala Val Gly Ser Gly Arg Tyr Phe Arg Ser
225                 230                 235                 240

Phe Thr Ala Ser Ser Leu Ser Gly Ser Trp Thr Pro Asn Ala Ala Thr
                245                 250                 255

Glu Ser Asn Pro Phe Ala Gly Lys Ala Asn Ser Gly Ala Thr Trp Thr
            260                 265                 270

Asn Asp Ile Ser His Gly Asp Leu Val Lys Val Thr Asn Asp Glu Thr
        275                 280                 285

Met Thr Val Asp Pro Cys Asn Leu Gln Leu Leu Tyr Gln Gly Arg Ala
    290                 295                 300

Pro Asn Ser Gly Gly Asp Tyr Asp Arg Leu Pro Tyr Arg Pro Gly Leu
305                 310                 315                 320

Leu Thr

<210> SEQ ID NO 21
<211> LENGTH: 363
<212> TYPE: PRT
<213> ORGANISM: Streptomyces thermoviolaceus

<400> SEQUENCE: 21

Met Ser Phe His Arg Ser Leu Pro Phe Arg Pro Lys Arg Leu Phe Gly
  1               5                  10                  15

Val Leu Ala Pro Leu Leu Leu Ala Gly Val Met Ser Thr Gln Pro Ala
             20                  25                  30

Gly Ala Ala Thr Val Val Pro Ser Asp Asp Val Gln Gly Thr Gly Arg
         35                  40                  45

Gln Ser Gln Leu Thr Asp Gly Phe Gly Thr Arg Ala Ser Cys Glu Leu
     50                  55                  60

Pro Ser Thr Tyr Arg Trp Thr Ser Thr Gly Ala Leu Ala Gln Pro Arg
 65                  70                  75                  80

Ser Gly Trp Val Ser Leu Lys Asp Phe Thr Val Val Pro Tyr Asn Gly
                 85                  90                  95

Gln His Leu Val Tyr Ala Thr Thr His Asp Thr Gly Thr Arg Trp Gly
            100                 105                 110

Ser Met Asn Phe Glu Pro Phe Gly Asp Trp Ser Gln Met Ala Thr Ala
```

```
                115                 120                 125
Arg Gln Asn Ala Met Asn Ser Pro Thr Val Ala Pro Thr Leu Phe Tyr
130                 135                 140

Phe Ala Pro Lys Asp Ile Trp Val Leu Ala Tyr Gln Trp Gly Gly Ser
145                 150                 155                 160

Ala Phe Ser Tyr Arg Thr Ser His Asp Pro Thr Asp Pro Asn Gly Trp
                165                 170                 175

Ser Ser Glu Gln Val Leu Phe Ser Gly Ser Ile Ala Asp Ser Ala Thr
            180                 185                 190

Gly Pro Ile Asp Gln Thr Leu Ile Gly Asp Asp Thr His Met Tyr Leu
        195                 200                 205

Phe Phe Ala Gly Asp Asn Gly Lys Ile Tyr Arg Ala Ser Met Pro Ile
    210                 215                 220

Gly Asp Phe Pro Gly Ser Phe Gly Ser Thr Ala Thr Val Val Met Ser
225                 230                 235                 240

Asp Thr Arg Asn Asn Leu Phe Glu Ala Pro Gln Val Tyr Lys Leu Gln
                245                 250                 255

Gly Gln Asn Arg Tyr Leu Met Ile Val Glu Ala Ile Gly Ala Gln Gly
            260                 265                 270

Gln Arg Tyr Phe Arg Ser Phe Thr Ala Thr Ser Leu Asp Gly Glu Trp
        275                 280                 285

Thr Pro Gln Ala Thr Ser Glu Ser Asn Pro Phe Ala Gly Lys Ala Asn
    290                 295                 300

Ser Gly Ala Thr Trp Thr Asp Asp Ile Ser His Gly Glu Leu Ile Arg
305                 310                 315                 320

Thr Thr Ala Asp Gln Thr Met Thr Val Asp Pro Cys Asn Leu Gln Leu
                325                 330                 335

Leu Tyr Gln Gly Arg Asp Pro Gly Ser Gly Thr Tyr Asp Leu Leu
            340                 345                 350

Pro Tyr Arg Pro Gly Leu Leu Thr Leu Gln Arg
        355                 360

<210> SEQ ID NO 22
<211> LENGTH: 24
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(24)
<223> OTHER INFORMATION: Xaa = Any Amino Acid

<400> SEQUENCE: 22

Leu Xaa Phe Met Pro Xaa Lys Ala Phe Ser Ala Leu Ala Leu Ala Leu
 1               5                  10                  15

Leu Ala Xaa Val Ala Ser Ala Gln
            20

<210> SEQ ID NO 23
<211> LENGTH: 304
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(304)
<223> OTHER INFORMATION: Xaa = Any Amino Acid

<400> SEQUENCE: 23
```

```
Ala Ser Cys Xaa Leu Pro Ser Thr Tyr Arg Trp Thr Ser Gly Ala
 1               5                  10                 15

Leu Ala Gln Pro Lys Ser Gly Trp Val Ser Leu Lys Asp Phe Thr Ile
             20                  25                  30

Val Xaa Tyr Asn Gly Gln His Leu Val Tyr Ala Thr Thr His Asp Thr
         35                  40                  45

Gly Thr Lys Trp Gly Ser Met Asn Phe Xaa Pro Phe Gly Asp Trp Ser
 50                      55                  60

Asn Met Ala Thr Ala Ser Gln Asn Ala Met Xaa Xaa Xaa Thr Val Ala
65                   70                  75                  80

Pro Thr Leu Phe Tyr Phe Ala Pro Lys Asn Ile Trp Val Leu Ala Tyr
                 85                  90                  95

Gln Trp Gly Pro Thr Thr Phe Ser Tyr Arg Thr Ser Ser Asp Pro Thr
             100                 105                 110

Xaa Pro Asn Gly Trp Ser Ser Xaa Gln Xaa Leu Phe Ser Gly Ser Ile
         115                 120                 125

Ser Gly Ser Ala Thr Gly Pro Ile Asp Gln Thr Val Ile Gly Asp Ala
         130                 135                 140

Thr Asn Met Tyr Leu Phe Phe Ala Gly Asp Asn Gly Lys Ile Tyr Arg
145                 150                 155                 160

Ala Ser Met Pro Ile Gly Asn Phe Pro Gly Ser Phe Gly Ser Thr Ser
                 165                 170                 175

Thr Val Val Met Ser Asp Ser Arg Asn Asn Leu Phe Glu Ala Val Gln
             180                 185                 190

Val Tyr Thr Val Xaa Gly Gln Xaa Xaa Tyr Leu Met Ile Val Glu Ala
             195                 200                 205

Ile Gly Ala Asn Gly Xaa Arg Tyr Phe Arg Ser Phe Thr Ala Thr Ser
             210                 215                 220

Leu Xaa Gly Ser Trp Thr Pro Gln Ala Thr Ser Glu Ser Asn Pro Phe
225                 230                 235                 240

Ala Gly Lys Ala Asn Ser Gly Ala Thr Trp Thr Asn Asp Ile Ser His
             245                 250                 255

Gly Asp Leu Ile Arg Ser Thr Xaa Asp Gln Thr Met Thr Val Asp Pro
             260                 265                 270

Cys Asn Leu Gln Leu Leu Tyr Gln Gly Arg Ala Pro Asn Ser Gly Gly
             275                 280                 285

Asp Tyr Asp Leu Leu Pro Tyr Arg Pro Gly Leu Leu Thr Leu Gln Arg
             290                 295                 300

<210> SEQ ID NO 24
<211> LENGTH: 302
<212> TYPE: PRT
<213> ORGANISM: Trichoderma reesei

<400> SEQUENCE: 24

Met Pro Ser Val Lys Glu Thr Leu Thr Leu Leu Ser Gln Ala Phe
 1               5                  10                 15

Leu Ala Thr Gly Ser Pro Val Asp Gly Glu Thr Val Val Lys Arg Gln
             20                  25                  30

Cys Pro Ala Ile His Val Phe Gly Ala Arg Glu Thr Thr Val Ser Gln
         35                  40                  45

Gly Tyr Gly Ser Ser Ala Thr Val Asn Leu Val Ile Gln Ala His
 50                      55                  60

Pro Gly Thr Thr Ser Glu Ala Ile Val Tyr Pro Ala Cys Gly Gly Gln
65                   70                  75                  80
```

```
Ala Ser Cys Gly Gly Ile Ser Tyr Ala Asn Ser Val Val Asn Gly Thr
                85                  90                  95

Asn Ala Ala Ala Ala Ala Ile Asn Asn Phe His Asn Ser Cys Pro Asp
            100                 105                 110

Thr Gln Leu Val Leu Val Gly Tyr Ser Gln Gly Ala Gln Ile Phe Asp
        115                 120                 125

Asn Ala Leu Cys Gly Gly Gly Asp Pro Gly Glu Gly Ile Thr Asn Thr
    130                 135                 140

Ala Val Pro Leu Thr Ala Gly Ala Val Ser Ala Val Lys Ala Ala Ile
145                 150                 155                 160

Phe Met Gly Asp Pro Arg Asn Ile His Gly Leu Pro Tyr Asn Val Gly
                165                 170                 175

Thr Cys Thr Thr Gln Gly Phe Asp Ala Arg Pro Ala Gly Phe Val Cys
            180                 185                 190

Pro Ser Ala Ser Lys Ile Lys Ser Tyr Cys Asp Ala Ala Asp Pro Tyr
        195                 200                 205

Cys Cys Thr Gly Asn Asp Pro Asn Val His Gln Gly Tyr Gly Gln Glu
    210                 215                 220

Tyr Gly Gln Gln Ala Leu Ala Phe Ile Asn Ser Gln Leu Ser Ser Gly
225                 230                 235                 240

Gly Ser Gln Pro Pro Gly Gly Gly Pro Thr Ser Thr Ser Arg Pro Thr
                245                 250                 255

Ser Thr Arg Thr Gly Ser Ser Pro Gly Pro Thr Gln Thr His Trp Gly
            260                 265                 270

Gln Cys Gly Gly Gln Gly Trp Thr Gly Pro Thr Gln Cys Glu Ser Gly
        275                 280                 285

Thr Thr Cys Gln Val Ile Ser Gln Trp Tyr Ser Gln Cys Leu
    290                 295                 300

<210> SEQ ID NO 25
<211> LENGTH: 310
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(310)
<223> OTHER INFORMATION: Xaa = Any Amino Acid

<400> SEQUENCE: 25

Ser Leu Ser Leu Xaa Leu Ser Xaa Ala Xaa Leu Ala Xaa Xaa Ser Xaa
  1               5                  10                  15

Xaa Xaa Xaa Xaa Thr Xaa Xaa Xaa Xaa Xaa Xaa Xaa Ala Ile His Met
            20                  25                  30

Xaa Xaa Ala Arg Xaa Ser Xaa Xaa Xaa Xaa Gly Xaa Gly Xaa Ser Ala
        35                  40                  45

Xaa Leu Xaa Xaa Xaa Ile Xaa Xaa Xaa Xaa Pro Gly Ser Xaa Xaa Xaa
    50                  55                  60

Ala Ile Xaa Tyr Pro Ala Xaa Xaa Xaa Xaa Xaa Xaa Xaa Xaa Xaa Xaa
65                  70                  75                  80

Xaa Tyr Xaa Xaa Ser Xaa Xaa Xaa Gly Xaa Xaa Ala Xaa Xaa Xaa Xaa
                85                  90                  95

Ile Asn Xaa Phe Xaa Xaa Ala Cys Pro Xaa Xaa Xaa Ile Xaa Leu Leu
            100                 105                 110

Gly Tyr Ser Gln Gly Ala Gln Ile Xaa Xaa Xaa Xaa Ile Cys Gly Gly
        115                 120                 125
```

```
Ala Xaa Xaa Xaa Xaa Xaa Xaa Ser Xaa Xaa Leu Ser Xaa
    130                 135                 140

Xaa Xaa Met Xaa Xaa Val Xaa Ala Xaa Xaa Xaa Gly Asp Pro Xaa
145             150                 155                 160

Xaa Ile Xaa Xaa Leu Xaa Tyr Xaa Xaa Gly Thr Xaa Xaa Xaa Asn Gly
            165                 170                 175

Xaa Xaa Xaa Arg Xaa Ala Xaa Xaa Xaa Xaa Xaa Xaa Xaa Xaa Ala
        180                 185                 190

Ser Lys Ile Xaa Ser Tyr Cys Asp Xaa Ala Asp Xaa Tyr Cys Xaa Xaa
            195                 200                 205

Gly Xaa Xaa Xaa Xaa Val His Xaa Xaa Tyr Xaa Gln Xaa Tyr Gly Xaa
    210                 215                 220

Xaa Xaa Leu Xaa Phe Ile Xaa Ser Gln Xaa Xaa Xaa Xaa Ser Xaa
225                 230                 235                 240

Xaa Xaa Gly Xaa Xaa Xaa Xaa Xaa Xaa Xaa Ala Pro Xaa Xaa
            245                 250                 255

Thr Xaa Xaa Pro Thr Ser Thr Xaa Xaa Gly Xaa Ser Xaa Xaa Pro Thr
        260                 265                 270

Xaa Thr Xaa Xaa Xaa Xaa Xaa Xaa Xaa Gly Xaa Gly Xaa Ser
            275                 280                 285

Ala Xaa Thr Xaa Xaa Xaa Xaa Xaa Xaa Xaa Xaa Ile Xaa Xaa
    290                 295                 300

Xaa Xaa Ser Gln Xaa Leu
305             310

<210> SEQ ID NO 26
<211> LENGTH: 400
<212> TYPE: PRT
<213> ORGANISM: Streptomyces coelicor

<400> SEQUENCE: 26

Met Arg Thr Arg Val Leu Arg Leu Leu Arg Pro Trp Thr Ala Ala
 1               5                  10                  15

Val Ala Ala Val Ala Leu Val Val Ser Val Leu Val Ala Met Pro Ala
            20                  25                  30

Ser Gly Ala Ala Ala Ala Cys Arg Val Asp Tyr Gly Val Asp Ala
        35                  40                  45

Trp Ala Gly Gly Tyr Thr Ala Arg Val Arg Ile Thr Asn Leu Gly Pro
50                  55                  60

Ala Val Ser Asp Trp Arg Leu Thr Trp Thr Tyr Thr Gly Asp Gln Gln
65                  70                  75                  80

Val Thr Ser Ala Trp Asn Ala Thr Val Thr Gln Thr Gly Ala Ser Val
                85                  90                  95

Val Ala Val Asp Ala Gly Trp Asn Gly Ala Val Ser Thr Gly Gly Thr
            100                 105                 110

Ala Glu Phe Gly Leu Gln Gly Thr Trp Arg Ser Ala Asp Pro Ala Pro
        115                 120                 125

Asp Asp Phe Ala Leu Asn Gly Thr Ser Cys Gly Asp Gly Gly Thr Pro
    130                 135                 140

Thr Ala Thr Pro Thr Thr Ser Pro Thr Ala Pro Pro Thr Thr Pro Pro
145                 150                 155                 160

Thr Thr Pro Pro Pro Thr Thr Pro Pro Ala Ala Glu Cys Gly Asp
                165                 170                 175

Ala Val Ile Cys Ser Gly Phe Glu Asp Gln Ala Gly Pro Glu Pro Ser
            180                 185                 190
```

```
Gly Asp Trp Arg Phe Thr Ala Pro Asp Cys Gln Gly Thr Gly Thr Ala
            195                 200                 205

Ala Val Asp Ser Ala Val Ser His Ala Gly Gly Arg Ser Leu Arg Val
    210                 215                 220

Asp Gly Arg Ala Gly Tyr Cys Asn His Ala Phe Val Ala His Thr Ala
225                 230                 235                 240

Asp Leu Ser Ser Val Gly Pro Val Met Tyr Val Arg Met Trp Val Arg
            245                 250                 255

His Thr Thr Ala Leu Pro Thr Ser His Val Thr Phe Val Ser Met Pro
            260                 265                 270

Asp Ser Ala Gln Gly Gly Arg Ala Leu Arg Val Gly Gln Asn Gly
            275                 280                 285

Ala Leu Gln Trp Asn Arg Glu Ser Asp Ala Thr Leu Pro Ala Gln
            290                 295                 300

Ser Pro Ala Gly Val Ala Leu Ser Arg Pro Leu Pro Thr Asp Gly Trp
305                 310                 315                 320

Gln Cys Leu Arg Phe Ala Ile Asp Thr Ser Ala Ala Gly Leu Asp Thr
                325                 330                 335

Trp Leu Gly Asp Glu Gln Val Pro Gly Leu His Ala Asp Gly Val Pro
            340                 345                 350

Thr Gln Asp Val Asp Gln Trp Leu Thr Arg Gly Thr Ala Pro Arg
            355                 360                 365

Pro Thr Ala Leu Arg Leu Gly Trp Glu Ser Tyr Ala Thr Gly Asp Asp
370                 375                 380

Thr Val Trp Phe Asp Asp Val Ala Val Gly Ser Ala Pro Ile Gly Cys
385                 390                 395                 400

<210> SEQ ID NO 27
<211> LENGTH: 236
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(236)
<223> OTHER INFORMATION: Xaa = Any Amino Acid

<400> SEQUENCE: 27

Thr Xaa Xaa Xaa Xaa Ala Xaa Xaa Xaa Xaa Xaa Xaa Ile Xaa Xaa
1               5                   10                  15

Xaa Xaa Asp Asp Xaa Xaa Xaa Xaa Xaa Xaa Xaa Xaa Trp Xaa Xaa
            20                  25                  30

Ser Ala Pro Asp Cys Asn Xaa Xaa Gly Thr Xaa Ala Leu Asp Ser Xaa
            35                  40                  45

Val Ala His Ala Gly Xaa Xaa Ser Leu Lys Val Xaa Gly Xaa Xaa Xaa
    50                  55                  60

Gly Tyr Cys Xaa His Xaa Phe Xaa Ala Xaa Thr Xaa Xaa Xaa Ser Xaa
65                  70                  75                  80

Xaa Xaa Xaa Xaa Met Tyr Val Arg Xaa Trp Ile Arg Xaa Xaa Thr Ala
                85                  90                  95

Leu Xaa Ser Xaa His Val Thr Phe Ile Xaa Met Pro Asp Ser Ala Gln
            100                 105                 110

Gly Gly Lys Xaa Leu Arg Ile Gly Gly Gln Xaa Xaa Xaa Leu Xaa Trp
            115                 120                 125

Asn Arg Glu Ser Asp Asp Ala Thr Leu Pro Xaa Xaa Ser Pro Xaa Gly
            130                 135                 140
```

-continued

```
Ile Ala Xaa Ser Xaa Xaa Leu Pro Thr Xaa Ala Phe Gln Cys Xaa Xaa
145                 150                 155                 160

Phe Xaa Ile Xaa Thr Xaa Ala Xaa Xaa Ile Asp Thr Trp Leu Xaa Xaa
                165                 170                 175

Xaa Xaa Ile Pro Gly Leu Xaa Xaa Xaa Xaa Xaa Xaa Asn Xaa Xaa
            180                 185                 190

Asp Xaa Xaa Trp Xaa Xaa Xaa Xaa Xaa Pro Xaa Xaa Thr Ala Leu
        195                 200                 205

Xaa Xaa Gly Trp Glu Ala Tyr Ala Xaa Xaa Xaa Xaa Thr Val Trp Phe
    210                 215                 220

Asp Asp Ile Ala Ile Ala Ser Xaa Xaa Ile Gly Cys
225                 230                 235

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
gacaatccaa acgacgct                                                  18

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
caatcgagat gtcgtcgaac                                                20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ctcctccaca cccggtgccg                                                20

<210> SEQ ID NO 31
<211> LENGTH: 17
<212> TYPE: DNA
<213> ORGANISM: Artificial Sequence
<220> FEATURE:
<223> OTHER INFORMATION: primer

<400> SEQUENCE: 31
tgctgccaat gggtccg                                                   17

<210> SEQ ID NO 32
<211> LENGTH: 17
<212> TYPE: DNA
<213> ORGANISM: Artificial Sequence
<220> FEATURE:
<223> OTHER INFORMATION: primer

<400> SEQUENCE: 32
acgtattcag gcaaccc                                                   17
```

```
<210> SEQ ID NO 33
<211> LENGTH: 17
<212> TYPE: DNA
<213> ORGANISM: Artificial Sequence
<220> FEATURE:
<223> OTHER INFORMATION: primer

<400> SEQUENCE: 33
gcagtggcca tggctcc                                                    17

<210> SEQ ID NO 34
<211> LENGTH: 17
<212> TYPE: DNA
<213> ORGANISM: Artificial Sequence
<220> FEATURE:
<223> OTHER INFORMATION: primer

<400> SEQUENCE: 34
ccagtacatg aactggc                                                    17

<210> SEQ ID NO 35
<211> LENGTH: 17
<212> TYPE: DNA
<213> ORGANISM: Artificial Sequence
<220> FEATURE:
<223> OTHER INFORMATION: primer

<400> SEQUENCE: 35
agacccaatg tctcccc                                                    17

<210> SEQ ID NO 36
<211> LENGTH: 17
<212> TYPE: DNA
<213> ORGANISM: Artificial Sequence
<220> FEATURE:
<223> OTHER INFORMATION: primer

<400> SEQUENCE: 36
cgaattgtgc tcctggc                                                    17

<210> SEQ ID NO 37
<211> LENGTH: 17
<212> TYPE: DNA
<213> ORGANISM: Artificial Sequence
<220> FEATURE:
<223> OTHER INFORMATION: primer

<400> SEQUENCE: 37
gtggttggac cggatgg                                                    17

<210> SEQ ID NO 38
<211> LENGTH: 17
<212> TYPE: DNA
<213> ORGANISM: Artificial Sequence
<220> FEATURE:
<223> OTHER INFORMATION: primer

<400> SEQUENCE: 38
cctaccgtgg tatcagg                                                    17

<210> SEQ ID NO 39
<211> LENGTH: 17
<212> TYPE: DNA
<213> ORGANISM: Artificial Sequence
<220> FEATURE:
<223> OTHER INFORMATION: primer

<400> SEQUENCE: 39
```

```
tggttctgct ggtcggg                                              17

<210> SEQ ID NO 40
<211> LENGTH: 17
<212> TYPE: DNA
<213> ORGANISM: Artificial Sequence
<220> FEATURE:
<223> OTHER INFORMATION: primer

<400> SEQUENCE: 40
catttcgaca tcatggc                                              17

<210> SEQ ID NO 41
<211> LENGTH: 17
<212> TYPE: DNA
<213> ORGANISM: Artificial Sequence
<220> FEATURE:
<223> OTHER INFORMATION: primer

<400> SEQUENCE: 41
ctgtcccacg cagaggc                                              17

<210> SEQ ID NO 42
<211> LENGTH: 17
<212> TYPE: DNA
<213> ORGANISM: Artificial Sequence
<220> FEATURE:
<223> OTHER INFORMATION: primer

<400> SEQUENCE: 42
ccggctggct tcgtctg                                              17

<210> SEQ ID NO 43
<211> LENGTH: 17
<212> TYPE: DNA
<213> ORGANISM: Artificial Sequence
<220> FEATURE:
<223> OTHER INFORMATION: primer

<400> SEQUENCE: 43
tggccgtaac cttggtg                                              17

<210> SEQ ID NO 44
<211> LENGTH: 17
<212> TYPE: DNA
<213> ORGANISM: Artificial Sequence
<220> FEATURE:
<223> OTHER INFORMATION: primer

<400> SEQUENCE: 44
cctctctcac gactcgc                                              17

<210> SEQ ID NO 45
<211> LENGTH: 17
<212> TYPE: DNA
<213> ORGANISM: Artificial Sequence
<220> FEATURE:
<223> OTHER INFORMATION: primer

<400> SEQUENCE: 45
gttcgatgag ttgtacc                                              17

<210> SEQ ID NO 46
<211> LENGTH: 21
<212> TYPE: DNA
<213> ORGANISM: Artificial Sequence
```

```
<220> FEATURE:
<223> OTHER INFORMATION: primer

<400> SEQUENCE: 46
cccccaaacg gaacaacttc c                                              21

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
ctgtatctgt ggttgtgtag g                                              21

<210> SEQ ID NO 48
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(14)
<223> OTHER INFORMATION: n = A,T,C or G

<400> SEQUENCE: 48
ggncartgyg gngg                                                      14

<210> SEQ ID NO 49
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(14)
<223> OTHER INFORMATION: n = A,T,C or G

<400> SEQUENCE: 49
adrcaytgng arta                                                      14

<210> SEQ ID NO 50
<211> LENGTH: 14
<212> TYPE: DNA
<213> ORGANISM: Artificial Sequence
<220> FEATURE:
<223> OTHER INFORMATION: primer

<400> SEQUENCE: 50
adrcaytgrc trta                                                      14

<210> SEQ ID NO 51
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(14)
<223> OTHER INFORMATION: n = A,T,C or G

<400> SEQUENCE: 51
adrcaytgng crta                                                      14
```

```
<210> SEQ ID NO 52
<211> LENGTH: 25
<212> TYPE: DNA
<213> ORGANISM: Artificial Sequence
<220> FEATURE:
<223> OTHER INFORMATION: primer

<400> SEQUENCE: 52
caccatggtt cgccggactg ctctg                                          25

<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53
ttataagcac tgggagtagt atgg                                           24

<210> SEQ ID NO 54
<211> LENGTH: 23
<212> TYPE: DNA
<213> ORGANISM: Artificial Sequence
<220> FEATURE:
<223> OTHER INFORMATION: primer

<400> SEQUENCE: 54
caccatggct tcccgcttct ttg                                            23

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
tcaactcagc gttggggttg                                                20

<210> SEQ ID NO 56
<211> LENGTH: 54
<212> TYPE: DNA
<213> ORGANISM: Artificial Sequence
<220> FEATURE:
<223> OTHER INFORMATION: primer

<400> SEQUENCE: 56
ggggacaagt ttgtacaaaa aagcaggcta tggagcttaa agcactcagt gccg           54

<210> SEQ ID NO 57
<211> LENGTH: 51
<212> TYPE: DNA
<213> ORGANISM: Artificial Sequence
<220> FEATURE:
<223> OTHER INFORMATION: primer

<400> SEQUENCE: 57
ggggaccact ttgtacaaga aagctgggtt cagcgctgga gagttagcag c              51

<210> SEQ ID NO 58
<211> LENGTH: 50
<212> TYPE: DNA
<213> ORGANISM: Artificial Sequence
<220> FEATURE:
<223> OTHER INFORMATION: primer

<400> SEQUENCE: 58
```

-continued

```
gggacaagt ttgtacaaaa aagcaggcta tgcgcgccct ctcactctcc            50
```

<210> SEQ ID NO 59
<211> LENGTH: 51
<212> TYPE: DNA
<213> ORGANISM: Artificial Sequence
<220> FEATURE:
<223> OTHER INFORMATION: primer

<400> SEQUENCE: 59

```
ggggaccact ttgtacaaga aagctgggtt cacagcatct gagacaccgc c         51
```

TRICHODERMA GENES

CROSS-REFERENCE TO RELATED APPLICATIONS

The present application is a divisional of U.S. patent application Ser. No. 12/683,108, filed Jan. 6, 2010, now U.S. Pat. No. 7,923,235, which is a divisional of U.S. patent application Ser. No. 10/555,358, filed May 28, 2004, now U.S. Pat. No. 7,666,648, which is a national stage application of International Application No. PCT/US04/16881, filed May 28, 2004, which claims the benefit of U.S. Provisional Application No. 60/474,411, filed May 29, 2003, and U.S. Provisional Application No. 60/475,826, filed Jun. 3, 2003, which are herein incorporated by reference.

STATEMENT AS TO RIGHTS TO INVENTIONS MADE UNDER FEDERALLY SPONSORED RESEARCH AND DEVELOPMENT

Portions of this work were funded by Subcontract No. ZCO-0-30017-01 with the National Renewable Energy Laboratory under Prime Contract No. DE-AC36-99GO10337 with the U.S. Department of Energy. Accordingly, the United States Government may have certain rights in this invention.

SEQUENCE LISTING

The sequence listing submitted via EFS, in compliance with 37 C.F.R. §1.52(e), is incorporated herein by reference. The sequence listing text file submitted via EFS contains the file "804US_D2_SeqListing.txt" created on Aug. 8, 2011, which is 63,811 bytes in size.

FIELD OF THE INVENTION

Disclosed herein are four genes—two genes encoding proteins comprising a cellulose binding domain, one arabinofuranosidase and one acetylxylan esterase. Also disclosed herein are the deduced proteins, and compositions containing the novel proteins. These compositions are especially useful in the textile, detergent, biomass conversion, feed and food applications, and pulp and paper industries. The genes were isolated from a filamentous fungus, *Trichoderma reesei* (also called *Hypocrea jecorina* interchangeably herein).

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., J. Biol. Chem., 10.1074/M003624200, Apr. 13, 2001). As the limits of non-renewable resources approach, the potential of cellulose to become a major renewable energy resource is enormous (Krishna et al., Bioresource Tech. 77:193-196, 2001). The effective utilization of cellulose through biological processes is one approach to overcoming the shortage of foods, feeds, and fuels (Ohmiya et al., Biotechnol. Gen. Engineer. Rev. 14:365-414, 1997).

Cellulose is a linear polysaccharide of glucose residues connected by β-1,4 linkages. In nature, cellulose is usually associated with lignin together with hemicelluloses such as xylans and glucomannans. The practical use of cellulases has been hampered by the nature of the known cellulases, which are often mixtures of cellulases having a variety of activities and substrate specificities. For that reason, it is desirable to identify cellulases having only the desired activities or proteins that may facilitate cellulase action.

Hemicellulose is one of any of several heteropolymers (matrix polysaccharides) present in almost all cell walls along with cellulose. Their molecular weights are usually lower than that of cellulose and they have a weak undifferentiated structure compared to crystalline cellulose. But the chains form a 'ground'—they bind with pectin to cellulose to form a network of cross-linked fibers. Thus, it would be beneficial to enhance hemicellulose degradation.

O-Glycosyl hydrolases (EC 3.2.1.-) are a widespread group of enzymes that hydrolyse the glycosidic bond between two or more carbohydrates, or between a carbohydrate and a non-carbohydrate moiety. A classification system for glycosyl hydrolases, based on sequence similarity, has led to the definition of up to 60 different families [HENRISSAT, B. AND BAIROCH, A. New families in the classification of glycosyl hydrolases based on amino acid sequence similarities. BIOCHEM. J. 293 781-788 (1993); HENRISSAT, B. A classification of glycosyl hydrolases based on amino acid sequence similarities. BIOCHEM. J. 280 309-316 (1991); DAVIES, G. AND HENRISSAT, B. Structures and mechanisms of glycosyl hydrolases. STRUCTURE 3 853-859 (1995); and HENRISSAT, B. AND BAIROCH, A. Updating the sequence-based classification of glycosyl hydrolases. BIOCHEM. J. 316 695-696 (1996)]. Acetyl xylan esterases (EC 3.1.1.72) are a group of enzymes that remove acetyl side groups from xylan. A classification system for carbohydrate esterases, based on sequence similarity, has led to the definition of 13 families, seven of which contain acetyl xylan esterases (COUTINHO, P. M. AND HENRISSAT, B., 1999 Carbohydrate-active enzymes server at URL: <http://afmb.cnrs-mrs.fr/CAZY/index.htmb).

In order to be efficient, the digestion of cellulose requires several types of enzymes acting cooperatively. At least three categories of enzymes are necessary to convert cellulose into glucose: endo (1,4)-beta-D-glucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose.

It is an object of the present invention to provide improved proteins having cellulose- or hemicellulose-degrading activity and polynucleotides encoding the proteins. It is an object of the present invention to provide improved proteins having cellulose- or hemicellulose-binding activity and polynucleotides encoding the proteins. The improved proteins may improve the degradation of cell wall material, e.g., cellulose and/or hemicellulose. The proteins may also improve the stability or activity of other enzymes involved in the degradation of plant cell wall material, e.g., biomass.

SUMMARY OF THE INVENTION

Provided herein are a novel genes, herein called cip1, cip2, axe2 and abf2. Also provided herein are the gene products encoded by the novel genes. At least two of the genes are co-expressed with genes in the cellulase family.

In a first aspect the present invention relates to a polynucleotide having a nucleotide sequence which encodes for the polypeptide of the invention.

In one embodiment the invention includes an isolated polynucleotide having a sequence which encodes CIP1, a sequence complementary to the cip1 gene coding sequence, and/or a composition comprising the polynucleotide. The polynucleotide may be mRNA, DNA, cDNA, genomic DNA, or an antisense analog thereof.

In another embodiment, a cip1 polynucleotide may comprise an isolated nucleic acid molecule which hybridizes to the complement of the nucleic acid presented as SEQ ID NO:1 under moderate to high stringency conditions, where the nucleic acid molecule encodes a CIP1 polypeptide that exhibits cellulose binding activity.

In another embodiment, the polynucleotide has at least 80%, 85%, 90%, 95%, 98% or more sequence identity to the sequence presented as SEQ ID NO:1 and encodes a CIP1 protein. In a specific embodiment, the polynucleotide comprises a sequence substantially identical to SEQ ID NO:1. The invention also contemplates fragments of the polynucleotide, preferably at least about 15-30 nucleotides in length.

In a second aspect, CIP1 polypeptides or proteins comprise a sequence having at least 80%, 85%, 90%, 95%, 98% or more sequence identity to the sequence presented as SEQ ID NO:3 or SEQ ID NO:5.

In one embodiment, the invention includes (i) fragments of CIP1, preferably at least about 20-100 amino acids in length, more preferably about 100-200 amino acids in length, and (ii) a composition comprising CIP1. In various embodiments, the fragment corresponds to the N-terminal domain of CIP1 or the C-terminal domain of CIP1.

It is an object of the invention to provide enzyme preparations that contain one or more cellulases and CIP1.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

The invention further provides recombinant expression vectors containing a nucleic acid sequence encoding CIP1 or a fragment or splice variant thereof, operably linked to regulatory elements effective for expression of the protein in a selected host. In a related aspect, the invention includes a host cell containing the vector.

In a fifth aspect the present invention relates to a recombinant host cell comprising the nucleic acid construct of the invention.

The invention further includes a method for producing CIP1 by recombinant techniques, by culturing recombinant prokaryotic or eukaryotic host cells comprising nucleic acid sequence encoding CIP1 under conditions effective to promote expression of the protein, and subsequent recovery of the protein from the host cell or the cell culture medium.

In a sixth aspect the present invention relates to a method for producing a polypeptide of the invention, the method comprising: (a) cultivating a microorganism capable of producing the polypeptide; and (b) recovering the polypeptide.

In a seventh aspect the invention provides for an enzymatic composition useful in the conversion of cellulose to ethanol. In a preferred embodiment the enzymatic composition comprises CIP1. The composition may further comprise additional cellulase or hemicellulase enzymes such as endoglucanases and/or cellbiohydrolases and/or xylanases and the like. The composition may be enriched in CIP1.

Further provided herein are analytical methods for detecting cip1 nucleic acids and CIP1 proteins also form part of the invention.

CIP2

In a first aspect the present invention relates to a polynucleotide having a nucleotide sequence which encodes for the polypeptide of the invention.

In one embodiment the invention includes an isolated polynucleotide having a sequence which encodes CIP2 (SEQ ID NO:7 or SEQ ID NO:9), a sequence complementary to the cip2 gene coding sequence (SEQ ID NO:6), and/or a composition comprising the polynucleotide. The polynucleotide may be mRNA, DNA, cDNA, genomic DNA, or an antisense analog thereof.

In another embodiment, a cip2 polynucleotide may comprise an isolated nucleic acid molecule which hybridizes to the complement of the nucleic acid presented as SEQ ID NO:6 under moderate to high stringency conditions, where the nucleic acid molecule encodes a CIP2 polypeptide that exhibits cellulose binding activity.

In another embodiment, the polynucleotide has at least 80%, 85%, 90%, 95%, 98% or more sequence identity to the sequence presented as SEQ ID NO:6 and encodes a CIP2 protein (SEQ ID NO:7) or portion thereof. In a specific embodiment, the polynucleotide comprises a sequence substantially identical to SEQ ID NO:6. The invention also contemplates fragments of the polynucleotide, preferably at least about 15-30 nucleotides in length.

In a second aspect, CIP2 polypeptides or proteins comprise a sequence having at least 80%, 85%, 90%, 95%, 98% or more sequence identity to the sequence presented as SEQ ID NO:7 or SEQ ID NO:9.

In one embodiment, the invention includes (i) fragments of CIP2, preferably at least about 20-100 amino acids in length, more preferably about 100-200 amino acids in length, and (ii) a composition comprising CIP2. In various embodiments, the fragment corresponds to the N-terminal domain of CIP2 or the C-terminal domain of CIP2.

It is an object of the invention to provide enzyme preparations that contain one or more cellulases and CIP2.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

The invention further provides recombinant expression vectors containing a nucleic acid sequence encoding CIP2 or a fragment or splice variant thereof, operably linked to regulatory elements effective for expression of the protein in a selected host. In a related aspect, the invention includes a host cell containing the vector.

In a fifth aspect the present invention relates to a recombinant host cell comprising the nucleic acid construct of the invention.

The invention further includes a method for producing CIP2 by recombinant techniques, by culturing recombinant prokaryotic or eukaryotic host cells comprising nucleic acid sequence encoding CIP2 under conditions effective to promote expression of the protein, and subsequent recovery of the protein from the host cell or the cell culture medium.

In a sixth aspect the present invention relates to a method for producing a polypeptide of the invention, the method comprising: (a) cultivating a microorganism capable of producing the polypeptide; and (b) recovering the polypeptide.

In a seventh aspect the invention provides for an enzymatic composition useful in the conversion of cellulose to ethanol. In a preferred embodiment the enzymatic composition comprises CIP2. The composition may further comprise additional cellulase or hemicellulase enzymes such as endoglucanases and/or cellbiohydrolases and/or xylanases and the like. The composition may be enriched in CIP2.

Further provided herein are analytical methods for detecting cip2 nucleic acids and CIP2 proteins also form part of the invention.

AXE2

In a first aspect the present invention relates to a polynucleotide having a nucleotide sequence which encodes for the polypeptide of the invention.

In one embodiment the invention includes an isolated polynucleotide having a sequence which encodes AXE2, a sequence complementary to the axe2 gene coding sequence, and/or a composition comprising the polynucleotide. The polynucleotide may be mRNA, DNA, cDNA, genomic DNA, or an antisense analog thereof.

In another embodiment, a axe2 polynucleotide may comprise an isolated nucleic acid molecule which hybridizes to the complement of the nucleic acid presented as SEQ ID NO:14 under moderate to high stringency conditions, where the nucleic acid molecule encodes a AXE2 polypeptide, wherein the nucleic acid molecule encodes a AXE2 polypeptide that exhibits acetylxylan esterase activity.

In another embodiment, the polynucleotide has at least 80%, 85%, 90%, 95%, 98% or more sequence identity to the sequence presented as SEQ ID NO:14 and encodes a AXE2 protein (SEQ ID NO:17 or SEQ ID NO:15). In a specific embodiment, the polynucleotide comprises a sequence substantially identical to SEQ ID NO:14. The invention also contemplates fragments of the polynucleotide, preferably at least about 15-30 nucleotides in length.

In a second aspect, AXE2 polypeptides or proteins comprise a sequence having at least 80%, 85%, 90%, 95%, 98% or more sequence identity to the sequence presented as SEQ ID NO:17 or SEQ ID NO:15.

In one embodiment, the invention includes (i) fragments of AXE2, preferably at least about 20-100 amino acids in length, more preferably about 100-200 amino acids in length, and (ii) a composition comprising AXE2. In various embodiments, the fragment corresponds to the N-terminal domain of AXE2 or the C-terminal domain of AXE2.

It is an object of the invention to provide enzyme preparations that contain one or more hemicellulases and AXE2.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

The invention further provides recombinant expression vectors containing a nucleic acid sequence encoding AXE2 or a fragment or splice variant thereof, operably linked to regulatory elements effective for expression of the protein in a selected host. In a related aspect, the invention includes a host cell containing the vector.

In a fifth aspect the present invention relates to a recombinant host cell comprising the nucleic acid construct of the invention.

The invention further includes a method for producing AXE2 by recombinant techniques, by culturing recombinant prokaryotic or eukaryotic host cells comprising nucleic acid sequence encoding AXE2 under conditions effective to promote expression of the protein, and subsequent recovery of the protein from the host cell or the cell culture medium.

In a sixth aspect the present invention relates to a method for producing a polypeptide of the invention, the method comprising: (a) cultivating a microorganism capable of producing the polypeptide; and (b) recovering the polypeptide.

In a seventh aspect the invention provides for an enzymatic composition useful in the conversion of cellulose to ethanol. In a preferred embodiment the enzymatic composition comprises AXE2. The composition may further comprise additional cellulase or hemicellulase enzymes such as endoglucanases and/or cellbiohydrolases and/or xylanases and the like. The composition may be enriched in AXE2.

Further provided herein are analytical methods for detecting axe2 nucleic acids and AXE2 proteins also form part of the invention.

ABF2

In a first aspect the present invention relates to a polynucleotide having a nucleotide sequence which encodes for the polypeptide of the invention.

In one embodiment the invention includes an isolated polynucleotide having a sequence which encodes ABF2, a sequence complementary to the abf2 gene coding sequence, and/or a composition comprising the polynucleotide. The polynucleotide may be mRNA, DNA, cDNA, genomic DNA, or an antisense analog thereof.

In another embodiment, an abf2 polynucleotide may comprise an isolated nucleic acid molecule which hybridizes to the complement of the nucleic acid presented as SEQ ID NO:10 under moderate to high stringency conditions, where the nucleic acid molecule encodes a ABF2 polypeptide, wherein the nucleic acid molecule encodes a ABF2 polypeptide that exhibits arabinofuranosidase activity.

In another embodiment, the polynucleotide has at least 80%, 85%, 90%, 95%, 98% or more sequence identity to the sequence presented as SEQ ID NO:10 and encodes a ABF2 protein. In a specific embodiment, the polynucleotide comprises a sequence substantially identical to SEQ ID NO:10. The invention also contemplates fragments of the polynucleotide, preferably at least about 15-30 nucleotides in length.

In a second aspect, ABF2 polypeptides or proteins comprise a sequence having at least 80%, 85%, 90%, 95%, 98% or more sequence identity to the sequence presented as SEQ ID NO:11 or SEQ ID NO:13.

In one embodiment, the invention includes (i) fragments of ABF2, preferably at least about 20-100 amino acids in length, more preferably about 100-200 amino acids in length, and (ii) a composition comprising ABF2. In various embodiments, the fragment corresponds to the N-terminal domain of ABF2 or the C-terminal domain of ABF2.

It is an object of the invention to provide enzyme preparations that contain one or more hemicellulases and ABF2.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

The invention further provides recombinant expression vectors containing a nucleic acid sequence encoding ABF2 or a fragment or splice variant thereof, operably linked to regulatory elements effective for expression of the protein in a selected host. In a related aspect, the invention includes a host cell containing the vector.

In a fifth aspect the present invention relates to a recombinant host cell comprising the nucleic acid construct of the invention.

The invention further includes a method for producing ABF2 by recombinant techniques, by culturing recombinant prokaryotic or eukaryotic host cells comprising nucleic acid sequence encoding ABF2 under conditions effective to promote expression of the protein, and subsequent recovery of the protein from the host cell or the cell culture medium.

In a sixth aspect the present invention relates to a method for producing a polypeptide of the invention, the method comprising: (a) cultivating a microorganism capable of producing the polypeptide; and (b) recovering the polypeptide.

In a seventh aspect the invention provides for an enzymatic composition useful in the conversion of cellulose to ethanol. In a preferred embodiment the enzymatic composition comprises ABF2. The composition may further comprise additional cellulase or hemicellulase enzymes such as endoglucanases and/or cellbiohydrolases and/or xylanases and the like. The composition may be enriched in ABF2.

Further provided herein are analytical methods for detecting abf2 nucleic acids and ABF2 proteins also form part of the invention.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE FIGURES

FIG. 1 is a single stranded depiction of the nucleic acid sequence (SEQ ID NO:1), of the *T. reesei* cip1 cDNA, wherein the non-coding sequence is underlined.

FIG. 2 is the coding sequence for *T. reesei* cip1 (SEQ ID NO:2) wherein the encoded signal sequence is indicated as bold nucleotides.

FIG. 3 shows the predicted amino acid sequence of CIP1 (SEQ ID NO:3), signal sequence (SEQ ID NO:4) and the mature protein sequence (SEQ ID NO:5) based on the nucleotide sequence provided in FIG. 1.

FIG. 4 is the coding sequence for *T. reesei* cip2 (SEQ ID NO:6).

FIG. 5 shows the predicted amino acid sequence of CIP2 (SEQ ID NO:7), signal sequence (SEQ ID NO:8) and mature protein sequence (SEQ ID NO:9) based on the nucleotide sequence provided in FIG. 4.

FIG. 6 is an alignment of CIP2 (SEQ ID NO:7) with *R. flavefaciens* cesA CAB55348 (SEQ ID NO:18). CIP2 has a predicted N-terminal signal sequence of 17 amino acids followed by 36 amino acids comprising a carbohydrate binding module of family CBM1 and a linker region which ends at approximately amino acid 95.

FIG. 7 is a single stranded depiction of the nucleic acid sequence (SEQ ID NO:10), of the *T. reesei* abf2 gene encoding an arabinofuranosidase.

FIG. 8 shows the predicted amino acid sequence of ABF2 (SEQ ID NO:11), signal sequence (SEQ ID NO:12) and mature protein sequence (SEQ ID NO:13) based on the nucleotide sequence provided in FIG. 7.

FIG. 9 is an alignment of ABF2 (SEQ ID NO:20) with *C. carbonum* ARF1 (SEQ ID NO:20) and *S. thermoviolaceus* stxIV (SEQ ID NO:21).

FIG. 10 is the cDNA sequence for the axe2 gene (SEQ ID NO:14) encoding an acetylxylan esterase.

FIG. 11 shows the predicted amino acid sequence of AXE2 (SEQ ID NO:15), signal sequence (SEQ ID NO:16) and mature protein sequence (SEQ ID NO:17) based on the nucleotide sequence provided in FIG. 9.

FIG. 12 is a sequence alignment of AXE2 (SEQ ID NO:15) with the *T. reesei* AXE1 (SEQ ID NO:24).

FIG. 13 shows a Northern blot for two fungal strains under varying conditions. Cultures of QM6a and RLP-37 were grown in glucose (lanes A), cellulose (lanes B), glycerol (lanes C) or glycerol supplemented with sophorose (lanes D). mRNA from each of the cultures was analyzed by Northern blot. The top set of bands for each gene was probed with labeled cDNAs as indicated. The lower set of bands for each gene was probed with an actin probe to correct for loading differences and differences in exposure times required to visualize the bands.

FIG. 14 is a representation of the results from microarray analysis performed to assess expression levels for each of the genes indicated. A) Shake flask analysis of induction by sophorose in two different strains. mRNA from cultures of QM6a and RL-P37 grown in glycerol or glycerol supplemented with 1 mM sophorose were individually labeled with Cy5 and with Cy3 fluorescent dyes. Labeled mRNA from sophorose-grown cultures was combined with reciprocally labeled mRNA from glycerol-grown cultures and hybridized to microarrays. The log ratio of the two different labeled mRNA species that bound to probes for each of the genes is indicated according to the color bar below. L.R.: log ratio. Color reflects the magnitude of sophorose-meditated induction of each of the genes indicated. Column 1: sophorose induction in RL-P37 cultures. Column 2: sophorose induction in QM6a cultures. Column 3: Fluorescently labeled mRNA from sophorose-induced RL-P37 cultures was co hybridized with reciprocally labeled mRNA from sophorose-induced QM6a cultures grown under like conditions. Color reflects the abundance of mRNA corresponding to each of the genes in RL-P37 relative to QM6a. B) Analysis of expression levels during culture on different carbon sources in fermenters. RLP-37 and QM6a mycelia were grown initially in glucose-containing medium. One hour after the glucose had been completely utilized; cultures were fed lactose at a rate that prevented accumulation in the medium. Samples were obtained during the glucose feed during carbon deprivation and 24 and 48 hours after commencement of the lactose feeding. Microarrays were used to determine the expression levels at each of the times relative to expression at carbon deprivation. Column 4: RL-P37 glucose feed, column 5: QM6a glucose feed, column 6: RL-P37 lactose feed 24 hours, column 7: RL-P37 lactose feed 48 hours, column 8: QM6a lactose feed 24 hours, column 9 QM6a lactose feed 48 hours.

FIG. 16 is a sequence alignment of CIP1 with the putative secreted hydrolase *Streptomyces coelicolor* A3 (accession number CAA18323, SEQ ID NO:26).

DETAILED DESCRIPTION OF THE INVENTION

Figure 15:
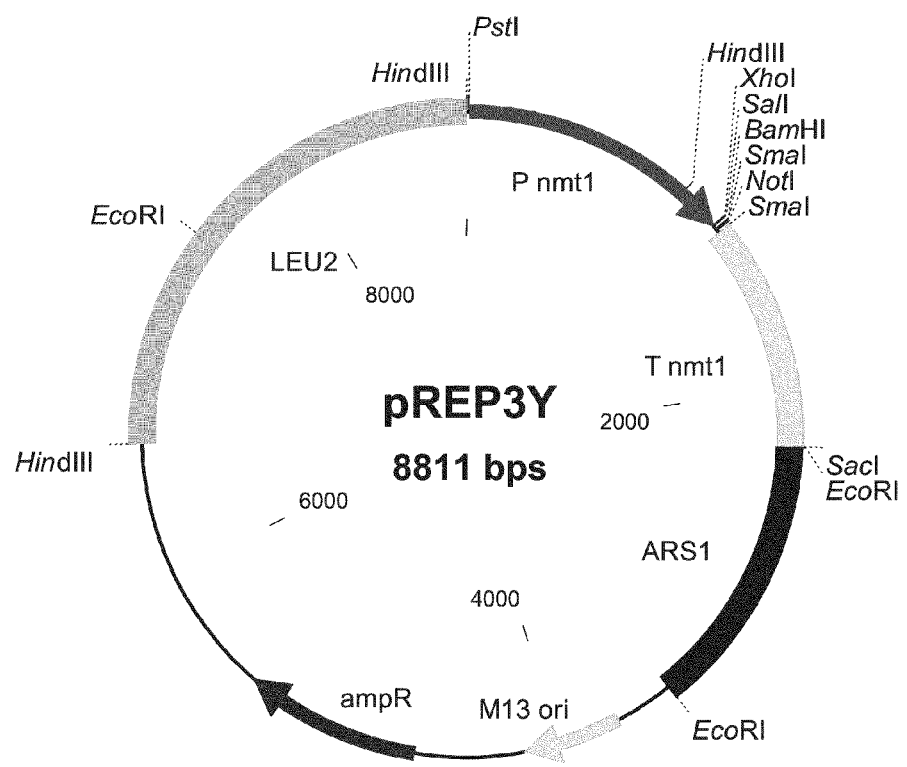
FIG. 15 is a schematic map of the pREP3Y vector.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., MOLECULAR CLONING: A LABORATORY MANUAL (Second Edition), Cold Spring Harbor Press, Plainview, N.Y., 1989, and Ausubel F M et al., CURRENT PROTOCOLS IN MOLECULAR BIOLOGY, John Wiley & Sons, New York, N.Y., 1993, for definitions and terms of the art. It is to be understood that this invention is not limited to the particular methodology, protocols, and reagents described, as these may vary.

The present invention provides the nucleotide sequences of *Trichoderma reesei* genes involved in cellulose and biomass degradation. The genes encode proteins with an enzyme activity that is either in use in an industry or of interest to an industry. The genomic sequences of the invention that encode the enzymes are identified primarily by comparison of nucleotide sequences of *T. reesei* genomic DNA and the nucleotide sequences of known enzyme genes of other microorganisms. Prior to this invention, the nucleotide sequences of these *T. reesei* genes, the reading frames, the positions of exons and introns, the structure of the enzymes, and their potential usefulness in various industries, such as those involved in the making of food and feed, beverages, textiles and detergents, were not known. Without limitation, the polynucleotides of the enzyme genes can be used to express recombinant enzymes for characterization, modifications or industrial uses; to compare with the nucleic acid sequence of *Trichoderma reesei* to identify duplicated genes or paralogs having the same or similar biochemical activity and/or function; to compare with nucleic acid sequences of other related or distant fungal organisms to identify potential orthologous enzyme genes; for selecting and making oligomers for attachment to a nucleic acid array for examination of expression patterns; and to raise anti-protein antibodies using nucleic acid immunization techniques. The sequence information provided herein can also form a basis for the design and testing of genetically modified enzymes which possess desirable chemical and physical characteristics.

All publications cited herein are expressly incorporated herein by reference for the purpose of describing and disclosing compositions and methodologies that might be used in connection with the invention.

The term "polypeptide" as used herein refers to a compound made up of a single chain of amino acid residues linked by peptide bonds. The term "protein" as used herein is used interchangeably with the term "polypeptide".

The term "nucleic acid molecule" includes RNA, DNA and cDNA molecules. It will be understood that, as a result of the degeneracy of the genetic code, a multitude of nucleotide sequences encoding a given protein such as, for example, CIP1 (or any other protein) may be produced. The present invention contemplates every possible variant nucleotide sequence, encoding CIP1, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode a novel protein as described herein or an analog or homologue thereof will hybridize, under moderate to high stringency conditions to the protein's corresponding nucleic acid sequence provided herein. However, in some cases a novel protein-encoding nucleotide sequence is employed that possesses a substantially different codon usage, while the protein encoded by the novel protein-encoding nucleotide sequence has the same or substantially the same amino acid sequence as the native protein. For example, the coding sequence may be modified to facilitate faster expression of the novel protein in a particular prokaryotic or eukaryotic expression system, in accordance with the frequency with which a particular codon is utilized by the host. Te'o, et al. FEMS Microbiology Letters 190:13-19, (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the phrase "novel protein" refers to at least one of the four novel proteins described herein, ABF2, AXE2, CIP1 and/or CIP2.

It follows that the term "novel protein expression" refers to transcription and translation of the novel protein-encoding gene, the products of which include precursor RNA, mRNA, polypeptide, post-translationally processed polypeptides, and derivatives thereof, including corresponding novel proteins from related species such as *Trichoderma longibrachia-*

*tum (reesei), Trichoderma viride, Trichoderma koningii, Hypocrea jecorina* and *Hypocrea schweinitzii*. By way of example, assays for the expression of novel proteins include Western blot for the novel protein, Northern blot analysis and reverse transcriptase polymerase chain reaction (RT-PCR) assays for the novel protein mRNA.

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*.

The term "cellooligosaccharide" refers to oligosaccharide groups containing from 2-8 glucose units and having β-1,4 linkages, e.g., cellobiose.

The term "cellulase" refers to a category of enzymes capable of hydrolyzing cellulose polymers to shorter cellooligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria.

The terms "cellulose binding domain" or "CBD" or "cellulose binding module" or "CBM" as used herein refer to a portion of the amino acid sequence of a protein or a region of the enzyme that is involved in the cellulose binding activity of a cellulolytic enzyme or derivative thereof. A domain is a stable part of a protein with different protein domains carrying out different functions. Thus, a catalytic core domain (or simply the core) contains the active site and carries out the enzymatic reaction. Similarly, cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulolytic enzyme protein tertiary structure that is distinct from the structural element which possesses catalytic activity. If a protein has more than one domain the domains are usually connected by a linker.

As used herein, the term "decrease or elimination in expression of the gene encoding a novel protein" means that either that the gene encoding the novel protein has been deleted from the genome and therefore cannot be expressed by the recombinant host microorganism; or that the gene encoding the novel protein has been modified such that a functional novel protein is not produced by the recombinant host microorganism, or the use of RNAi to specifically target a novel gene's product, resulting in null or hypomorphic phenotypes.

The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The term "altered gene" or "altered gene encoding the novel protein" means that the nucleic acid sequence of the gene has been altered by removing, adding, and/or manipulating the coding sequence or the amino acid sequence of the expressed protein has been modified.

As used herein, the term "purifying" generally refers to subjecting nucleic acid or protein containing cells to biochemical purification and/or column chromatography.

The terms "isolated" or "purified" as used herein refer to a nucleic acid or protein that is removed from at least one component with which it is naturally associated.

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

As used herein, the terms "active" and "biologically active" refer to a biological activity associated with a particular protein, such as the enzymatic activity associated with a protease. It follows that the biological activity of a given protein refers to any biological activity typically attributed to that protein by those of skill in the art.

As used herein, the term "enriched" means that the novel protein is found in a concentration that is greater relative to the novel protein concentration found in a wild-type, or naturally occurring, fungal cellulase composition.

When employed in enzymatic solutions, the novel protein component is generally added in an amount sufficient to: for the CIP proteins, enhance the action of the CBH and endoglucanase components found in the cellulase composition; for the arabinofuranosidase and acetylxylanesterase, enhance the action of a xylanase. The amount of novel protein component added depends upon the level of enhanced action desired provided by the novel protein, which can be readily determined by the skilled artisan. However, when employed, the weight percent of the novel protein component is preferably from about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

SCOPE OF INVENTION

*Trichoderma reesei* strains used in this study were obtained from the American Type Culture collection. However, it is to be understood that other microbial sources may be utilized to identify corresponding polypeptide homologs. It should be noted that the name *Hypocrea jecorina* may be used interchangeably herein with *Trichoderma reesei*.

The headings provided herein are not limitations of the various aspects or embodiments of the invention which can be had by reference to the specification as a whole. Accordingly, the terms defined immediately below are more fully defined by reference to the specification as a whole.

I. Host Organisms

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum, Trichoderma viride, Trichoderma koningii, Trichoderma harzianum; Penicillium* sp.; *Humicola* sp., including *Humicola insolens* and *Humicola grisea; Chrysosporium* sp., including *C. lucknowense; Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus tubingensis, Aspergillus foetidus, Aspergillus oryzae, Aspergillus sojae, Aspergillus aculeatus*, or *Aspergillus nidulans* cell.

In another preferred embodiment, the filamentous fungal parent cell is a *Trichoderma reesei* cell.

II. Molecular Biology

In one embodiment this invention provides for the expression of the novel genes described herein under the control of a promoter functional in a filamentous fungus. Therefore, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994)).

A. Methods of Identifying Novel Sequences

Techniques that can be used to isolate the novel protein-encoding DNA sequences are well known in the art and include, but are not limited to, cDNA and/or genomic library screening with a homologous DNA probes and expression screening with activity assays or antibodies against the novel proteins. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

Over 5000 cDNAs from *T. reesei* were partially or fully sequenced. Four cDNAs encoding new enzymes with putative roles in biomass degradation were discovered.

Open reading frames (ORFs) are analyzed following full or partial sequencing of clones of cDNA libraries derived from *T. reesei* mRNA and are further analyzed using sequence analysis software, and by determining homology to known sequences in databases (public/private).

The nucleotide sequences were initially annotated by software programs, such as Genescan and Glimmer M (The Institute of Genome Research, Rockville, N. Mex.), which can identify putative coding regions, introns, and splice junctions. Further automated and manual curation of the nucleotide sequences were performed to refine and establish precise characterization of the coding regions and other gene features.

B. Nucleic Acid Constructs/Expression Vectors.

Natural or synthetic polynucleotide fragments encoding a novel protein may be incorporated into heterologous nucleic acid constructs or vectors, capable of introduction into, and replication in, a filamentous fungal or yeast cell. The vectors and methods disclosed herein are suitable for use in host cells for the expression of a novel protein. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., The Molecular Biology of the Yeast *Saccharomyces* 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for a novel protein may be produced by introducing a heterologous nucleic acid construct comprising the novel protein coding sequence into the cells of a selected strain of the filamentous fungi.

Once the desired form of a novel protein nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected novel protein coding sequence may be inserted into a suitable vector according to well-known recombinant techniques and used to transform filamentous fungi capable of heterologous protein expression. Due to the inherent degeneracy of the genetic code, other nucleic acid sequences which encode substantially the same or a functionally equivalent amino acid sequence may be used to clone and express a novel protein. Therefore it is appreciated that such substitutions in the coding region fall within the sequence variants covered by the present invention.

The present invention also includes recombinant nucleic acid constructs comprising one or more of the novel protein-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a novel protein: (i) in isolation; (ii) in combination with additional coding sequences; such as fusion protein or signal peptide coding sequences, where the novel protein coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the novel protein coding sequence is a heterologous gene.

In one aspect of the present invention, a heterologous nucleic acid construct is employed to transfer a novel protein-encoding nucleic acid sequence into a cell in vitro, with established filamentous fungal and yeast lines preferred. For long-term, production of a novel protein, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a novel protein. Such linkage comprises positioning of the promoter with respect to the initiation codon of the DNA sequence encoding the novel protein in the disclosed expression vectors. The promoter sequence contains transcription and translation control sequence which mediate the expression of the novel protein. Examples include the promoters from the *Aspergillus niger, A awamori* or *A. oryzae* glucoamylase, alpha-amylase, or alpha-glucosidase encoding genes; the *A. nidulans* gpdA, oliC or trpC Genes; the *Neurospora crassa* cbh1 or trp1 genes; the *A. niger* or *Rhizomucor miehei* aspartic proteinase encoding genes; the *T. reesei* (*Hypocrea jecorina*) cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei* (*H. jecorina*), amdS from *A. nidulans*, pyr4 from *Neurospora crassa* or *H. jecorina*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMA1 sequences from *A. nidulans*, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, ANIMAL CELL CULTURE, 1987; Ausubel, et al., CURRENT PROTOCOLS IN MOLECULAR BIOLOGY, John Wiley & Sons, New York, N.Y., 1993; and Coligan et al., CURRENT PROTOCOLS IN IMMUNOLOGY 1991. All patents, patent applications, articles and publications mentioned herein, are hereby expressly incorporated herein by reference.

C. Methods for Transforming a Host Cell

In the present invention, the filamentous fungal parent cell may be a cell of a species of, but not limited to, *Trichoderma*, e.g., *Trichoderma longibrachiatum* (reesei), *Trichoderma viride*, *Trichoderma koningii*, *Trichoderma harzianum*; *Penicillium* sp.; *Humicola* sp., including *Humicola insolens*; *Chrysosporium* sp., including *C. lucknowense*; *Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

Examples of parental cell lines which may be treated and/or modified for novel protein expression include, but are not limited to, filamentous fungal cells. Examples of appropriate primary cell types for use in practicing the invention include, but are not limited to, *Aspergillus* and *Trichoderma*.

In one embodiment, the filamentous fungal parent cell is an *Aspergillus niger*, *Aspergillus awamori*, *Aspergillus tubingensis*, *Aspergillus foetidus*, *Aspergillus oryzae*, *Aspergillus sojae*, *Aspergillus aculeatus*, or *Aspergillus nidulans* cell.

In a second embodiment, the filamentous fungal parent cell is a *Hypocrea jecorina* cell. This cell was previously referred to as *T. reesei*.

After DNA sequences that encode the novel protein have been cloned into DNA constructs, the DNA is used to transform microorganisms. The microorganism to be transformed for the purpose of expressing a novel protein according to the present invention may advantageously comprise a strain derived from *Trichoderma* sp. Thus, a preferred mode for preparing novel protein according to the present invention comprises transforming a *Trichoderma* sp. host cell with a DNA construct comprising at least a fragment of DNA encoding a portion or all of the novel protein. The DNA construct will generally be functionally attached, i.e., operably linked, to a promoter. The transformed host cell is then grown under conditions so as to express the novel protein. Subsequently, the novel protein may be isolated. It may be desirable to have the novel protein in a substantially pure form. Similarly, it may be desirable to have the novel protein in an essentially pure form.

However, it may in fact be that the best expression vehicle for a given DNA encoding a novel protein may differ from *H. jecorina* (i.e., *T. reesei*). Thus, it may be that it will be most advantageous to express a protein in a transformation host that bears phylogenetic similarity to the source organism for the novel protein. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of a *Trichoderma* spp. expression system is provided for illustrative purposes only and as one option for expressing the novel protein of the invention. One of skill in the art, however, may be inclined to express the DNA encoding novel protein in a different host cell if appropriate and it should be understood that the source of the novel protein should be considered in determining the optimal expression host. Additionally, the skilled worker in the field will be capable of selecting the best expression system for a particular gene through routine techniques utilizing the tools available in the art.

D. Methods for Expressing a Novel Protein

The methods of the invention rely on the use of cells to express a novel protein, with no particular method of expression required.

The invention provides host cells that have been transduced, transformed or transfected with an expression vector comprising a novel protein-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding a novel protein, such that the novel protein is expressed in the cell line.

Thus, the present invention provides filamentous fungi comprising cells which have been modified, selected and cultured in a manner effective to result in novel protein production or expression relative to the corresponding non-transformed parental fungi.

Examples of species of parental filamentous fungi that may be treated and/or modified for novel protein expression include, but are not limited to *Trichoderma*, *Penicillium* sp., *Humicola* sp., including *Humicola insolens*; *Aspergillus* sp., including *Aspergillus niger*, *Chrysosporium* sp., *Fusarium* sp., *Hypocrea* sp., and *Emericella* sp.

Cells expressing a novel protein are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28° C. in shaker cultures or fermenters until desired levels of novel protein expression are achieved.

Preferred culture conditions for a given filamentous fungus may be found in the scientific literature and/or from the source of the fungi such as the American Type Culture Collection (ATCC). After fungal growth has been established, the cells are exposed to conditions effective to cause or permit the expression of a novel protein.

In cases where a novel protein-coding sequence is under the control of an inducible promoter, the inducing agent, e.g., a sugar, metal salt or antibiotics, is added to the medium at a concentration effective to induce novel protein expression.

In one embodiment, the strain comprises *Aspergillus niger*, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAPS-4 are known (Ward, M, Wilson, L. J. and Kodama, K. H., 1993, Appl. Microbiol. Biotechnol. 39:738-743).

In another embodiment, the strain comprises *Trichoderma reesei*, which is a useful strain for obtaining overexpressed protein. For example, RL-P37, described by Sheir-Neiss, et al., *Appl. Microbiol. Biotechnol.* 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing a novel protein.

Where it is desired to obtain the desired novel protein in the absence of potentially detrimental native cellulolytic activity, it is useful to obtain a host cell strain which has had one or more cellulase genes deleted prior to introduction of a DNA construct or plasmid containing the DNA fragment encoding the novel protein. Such strains may be prepared by the method disclosed in U.S. Pat. No. 5,246,853 and WO 92/06209, which disclosures are hereby incorporated by reference. By expressing a novel protein in a host microorganism that is missing one or more cellulase genes, the identification and subsequent purification procedures are simplified. Any gene from *Trichoderma* sp. which has been cloned can be deleted, for example, the cbh1, cbh2, egl1, and egl2 genes as well as those encoding EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of a *Aspergillus* sp. gene may be used which if lacking in the host strain results in the host strain displaying an auxotrophic phenotype.

In one embodiment, a pyrG$^-$ derivative strain of *Aspergillus* sp. is transformed with a functional pyrG gene, which thus provides a selectable marker for transformation. A pyrG$^-$ derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG$^-$ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, *Curr. Genet.* 19:359-365 (1991), and van Hartingsveldte et al., (1986) Development of a homologous transformation system for *Aspergillus niger* based on the pyrG gene. Mol. Gen. Genet. 206:71-75). Selection of derivative strains is easily performed using the FOA resistance technique referred to above, and thus, the pyrG gene is preferably employed as a selectable marker. In another embodiment, a pyr4$^-$ derivative strain of *Trichoderma* sp. is transformed with a functional pyr4 gene, which thus provides a selectable marker for transformation. Although the following discusses the *Aspergillus* system, similar procedures for *Trichoderma* and other fungal systems may be used as will be appreciated by one skilled in the art.

To transform pyrG$^-$ *Aspergillus* sp. so as to be lacking in the ability to express one or more cellulase genes, a single DNA fragment comprising a disrupted or deleted cellulase gene is then isolated from the deletion plasmid and used to transform an appropriate pyr$^-$ *Aspergillus* host. Transformants are then identified and selected based on their ability to express the pyrG gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the pyr4 selectable markers.

Although the specific plasmid vectors described above relate to preparation of pyr$^-$ transformants, the present invention is not limited to these vectors. Various genes can be deleted and replaced in the *Aspergillus* sp. strain using the above techniques. In addition, any available selectable markers can be used, as discussed above. In fact, any *Aspergillus* sp. gene that has been cloned, and thus identified, can be deleted from the genome using the above-described strategy.

As stated above, the host strains used are derivatives of *Aspergillus* sp. that lack or have a nonfunctional gene or genes corresponding to the selectable marker chosen. For example, if the selectable marker of pyrG is chosen, then a specific pyrG$^-$ derivative strain is used as a recipient in the transformation procedure. Similarly, selectable markers comprising *Aspergillus* sp. genes equivalent to the *Aspergillus nidulans* genes amdS, argB, trpC, niaD may be used. The corresponding recipient strain must therefore be a derivative strain such as argB$^-$, trpC$^-$, niaD$^-$, respectively.

DNA encoding the novel protein is then prepared for insertion into an appropriate microorganism. According to the present invention, DNA encoding a novel protein comprises the DNA necessary to encode for a protein that has functional activity, e.g., enzymatic activity and/or substrate binding. The DNA fragment encoding the novel protein may be functionally attached to a fungal promoter sequence, for example, the promoter of the glaA gene.

It is also contemplated that more than one copy of DNA encoding a novel protein may be recombined into the strain to facilitate overexpression. The DNA encoding the novel protein may be prepared by the construction of an expression vector carrying the DNA encoding the novel protein. The expression vector carrying the inserted DNA fragment encoding the novel protein may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pRAX is such a general-purpose expression vector. Genes or part thereof can be inserted downstream of the strong glaA promoter. An example of an integrative expression vector is the pTrex vector. Genes or part thereof can be inserted downstream of the strong cbh1 promoter.

In the vector, the DNA sequence encoding the novel protein of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the novel protein. The DNA encoding the signal sequence is preferably that which is naturally associated with the gene to be expressed, however the signal sequence from any suitable source is contemplated in the present invention.

The procedures used to fuse the DNA sequences coding for the novel protein of the present invention with the promoter into suitable vectors are well known in the art.

Various methods may be employed for delivering an expression vector, DNA vector or construct described above into cells in vitro. Methods of introducing nucleic acids into cells for expression of heterologous nucleic acid sequences are also known to the ordinarily skilled artisan, including, but not limited to electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; *Agrobacterium*-mediated transfer of DNA; and the like. In addition, heterologous nucleic acid constructs comprising a novel protein-encoding nucleic acid sequence can be transcribed in vitro, and the resulting RNA introduced into the host cell by well-known methods, e.g., by injection.

The preferred method in the present invention to prepare *Aspergillus* sp. for transformation involves the preparation of protoplasts from fungal mycelium. See Campbell et al. Improved transformation efficiency of *A. niger* using homologous niaD gene for nitrate reductase. Curr. Genet. 16:53-56; 1989. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host *Aspergillus* sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropane-sulfonic acid) and polyethylene glycol (PEG). It is believed that the polyethylene glycol acts to fuse the cell membranes thus permitting the contents of the medium to be delivered into the cytoplasm of the *Aspergillus* sp. strain and the plasmid DNA is transferred to the nucleus. This fusion frequently leaves multiple copies of the plasmid DNA tenderly integrated into the host chromosome.

Usually a suspension containing the *Aspergillus* sp. protoplasts or cells that have been subjected to a permeability treatment at a density of $10^5$ to $10^6$/mL, preferably $2 \times 10^5$/mL are used in transformation. A volume of 100 μL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. See, for example, U.S. Pat. No. 6,268,328, the contents of which are hereby incorporated by reference.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine. Alternatively, other methods known in the art may be used to select transformants.

In a particular embodiment of the above method, the novel protein are recovered in active form from the host cell after growth in liquid media either as a result of the appropriate post translational processing of the novel protein.

E. Methods of Analysis for Novel Protein Nucleic Acid Coding Sequences and/or Protein Expression.

In order to evaluate the expression of a novel protein by a cell line that has been transformed with a novel protein-encoding nucleic acid construct, assays can be carried out at the protein level, the RNA level or by use of functional bioassays particular to the novel protein's activity and/or production.

In one exemplary application of the novel protein nucleic acid and protein sequences described herein, a genetically modified strain of filamentous fungi, e.g., *Trichoderma reesei*, is engineered to produce an increased amount of a novel protein. Such genetically modified filamentous fungi would be useful to produce a cellulase or hemicellulase product with greater increased cellulolytic or hemicellulolytic capacity. In one approach, this is accomplished by introducing the coding sequence for a novel protein into a suitable host, e.g., a filamentous fungi such as *Aspergillus niger*.

Accordingly, the invention includes methods for expressing a novel protein in a filamentous fungus or other suitable host by introducing an expression vector containing the DNA sequence encoding a novel protein into cells of the filamentous fungus or other suitable host.

In another aspect, the invention includes methods for modifying the expression of a novel protein in a filamentous fungus or other suitable host. Such modification includes a decrease or elimination in expression of the endogenous novel protein.

In general, assays employed to analyze the expression of a novel protein include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

The production and/or expression of a novel protein may be measured in a sample of cell lysate or culture supernatant directly by sodium dodecyl sulphate-polyacrylamide gel electrophoresis (SDS-PAGE) using methods known in the art. After separation of proteins in the sample by electrophoresis and staining with a suitable dye (e.g., Coomassie Brilliant Blue) production of a novel protein would be demonstrated by appearance of a novel protein band. In addition, the production and/or expression of a novel protein may be measured in a sample directly, for example, by assays for enzymatic activity, expression and/or production.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a novel protein. The details of such methods are known to those of skill in the art and many reagents for practicing such methods are commercially available.

A purified form of a novel protein may be used to produce either monoclonal or polyclonal antibodies specific to the expressed protein for use in various immunoassays. (See, e.g., Hu et al., Mol Cell Biol. 11:5792-9, 1991). Exemplary assays include ELISA, competitive immunoassays, radioimmunoassays, Western blot, indirect immunofluorescent assays and the like.

F. Methods for Purifying a Novel Protein

In general, a novel protein produced in cell culture is secreted into the medium and may be purified or isolated, e.g., by removing unwanted components from the cell culture medium. However, in some cases, a novel protein may be produced in a cellular form necessitating recovery from a cell lysate. In such cases the novel protein is purified from the cells in which it was produced using techniques routinely employed by those of skill in the art. Examples include, but are not limited to, affinity chromatography (Tilbeurgh et al., FEBS Lett. 16:215, 1984), ion-exchange chromatography methods (Goyal et al., Bioresource Technol. 36:37, 1991; Fliess et al., Eur. J. Appl. Microbiol. Biotechnol. 17:314, 1983; Bhikhabhai et al., J. Appl. Biochem. 6:336, 1984; Ellouz et al., J. Chromatography 396:307, 1987), including ion-exchange using materials with high resolution power (Medve et al., J. Chromatography A 808:153, 1998), hydrophobic interaction chromatography (Tomaz and Queiroz, J. Chromatography A 865:123-128, 1999), and two-phase partitioning (Brumbauer, et al., Bioseparation 7:287-295, 1999).

Typically, the novel protein is fractionated to segregate proteins having selected properties, such as binding affinity to particular binding agents, e.g., antibodies or receptors; or which have a selected molecular weight range, or range of isoelectric points.

Once expression of a given novel protein is achieved, the novel protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, Methods Enzymol. 182:779-80, 1990; Scopes, Methods Enzymol. 90 Pt E:479-90, 1982. The purification step(s) selected will depend, e.g., on the nature of the production process used and the particular protein produced.

III. Biochemical Characteristics of the Novel Protein

A. Acetyl Xylan Esterases (axe2)

The AXE2 protein is predicted to have 299 amino acids and a molecular weight of about 30 kDaltons. The predicted protein is composed of 15 strongly basic(+) amino acids (K,R), 28 strongly acidic(−) amino acids (D,E), 91 hydrophobic amino acids (A,I,L,F,W,V), and 108 polar amino acids (N,C, Q,S,T,Y). AXE2 is predicted to have an isoelectric point of 4.5 and a—12.9 charge at pH 7.0.

Axe2 is a member of the carbohydrate esterase family 5 (CE5). It is predicted to have N-terminal signal sequence of 21 amino acids. See FIG. 11.

It has a putative GPI-anchor attachment site at amino acid number 274, corresponding to the serine residue at position 291 in the alignment (Udenfriend, S, and K. Kodukula. 1995. Prediction of ω site in nascent precursor of glycophosphatidylinositol protein. Methods in Enzymology. 250:57-82). See FIG. 12. A form of this protein that can be secreted to the culture medium of a host organism may be generated by construction of an expression vector for a version of the axe2 gene that lacks the putative GPI-anchor attachment site and associated carboxyl terminal hydrophobic domain.

B. Arabinofuranosidase (abf2)

The ABF2 protein is predicted to have 322 amino acids and a molecular weight of about 35 kDaltons. The predicted protein is composed of 17 strongly basic(+) amino acids (K,R), 18 strongly acidic(−) amino acids (D,E), 107 hydrophobic amino acids (A,I,L,F,W,V), and 118 polar amino acids (N,C, Q,S,T,Y). ABF2 is predicted to have an isoelectric point of 6.4 and a −0.9 charge at pH 7.0.

Abf2 is a member of the glycosyl hydrolase family 62. It is predicted to have an N-terminal signal sequence of 19 amino acids. See FIGS. 8 and 9.

C. CIP1

The CIP1 protein is predicted to have 316 amino acids and a molecular weight of about 33 kDaltons. The predicted protein is composed of 14 strongly basic(+) amino acids (K,R), 23 strongly acidic(−) amino acids (D,E), 86 hydrophobic amino acids (A,I,L,F,W,V), and 116 polar amino acids (N,C, Q,S,T,Y). CIP1 is predicted to have an isoelectric point of 4.8 and a −8.3 charge at pH 7.0.

The protein sequence predicted from the DNA sequence has a predicted signal sequence for secretion, a C-terminal cellulose binding domain. The amino acid sequence has been compared and appeared to have regions homologous to:

core: 42% identical to a putative secreted hydrolase gene from *Streptomyces coelicolor*
linker: 48% identical to *T. reesei* EG4
CBD: 100% identical to the CBD of *T. reesei* CBH1

The sequence of CIP1 predicts that it contains a carbohydrate (cellulose) binding module and a secretion signal. CIP1 does not fit into any of the currently defined classes of glycosyl hydrolases, but is very similar to the unassigned putative secreted hydrolase from *Streptomyces coelicolor* (TrEMBL accession number 069962). The regulation of cip1 among strains with varying cellulase-producing capabilities and across a variety of conditions is indistinguishable from the endoglucanases and particularly the cellobiohydrolase cbh1. Its pronounced coregulation with this canonically-regulated cellulase component furthers the notion that cip1 encodes a previously unrecognized activity with a potential role in biomass degradation. See FIG. 3.

D. CIP2

The CIP2 protein is predicted to have 460 amino acids and a molecular weight of about 48 kDaltons. The predicted protein is composed of 24 strongly basic(+) amino acids (K,R), 24 strongly acidic(−) amino acids (D,E), 160 hydrophobic amino acids (A,I,L,F,W,V), and 165 polar amino acids (N,C,Q,S,T,Y). CIP2 is predicted to have an isoelectric point of 7.1 and a 0.27 charge at pH 7.0.

CIP2 has a predicted N-terminal signal sequence of 17 amino acids followed by 36 amino acids comprising a carbohydrate binding module of family CBM1 and a linker region which ends at approximately amino acid 95. See FIGS. 5 and 6.

IV. Utility of Identified Genes of Interest

The inventive genes can be used in a variety of different applications.

A. Acetyl Xylan Esterases (AXE2)

It is anticipated that acetyl xylan esterase functionality encoded by SEQ ID NO:14 (see FIG. 10) will provide a synergistic effect when used, in combination with xylanase, in applications where it is desirable to hydrolyze xylan based substrates to xylose. The primary xylan hydrolysis would be enhanced by the ability of acetyl xylan esterase to remove acetyl side groups, thereby rendering the xylan chains present in various substrates more accessible to xylanase activity.

The above acetyl xylan esterase functionality would be of potential benefit in a number of agricultural and industrial applications:

in vivo modification of xylan containing animal feeds to improve digestability.
general applications resulting from biomass degradation to fermentable sugars.
processing aids used in pulp and paper de-lignification.
component of enzymatic scouring systems for textiles.
food applications—specifically baking—in combination with other enzymatic functionalities to improve the physical properties of baked goods.
laundry detergent applications—removal of grass stains— in combination with other enzyme functionalities.

B. CIP1 and CIP 2 (Cellulose Induced Protein 1 and 2)

The CBD containing CIP1 encoded by SEQ ID NOS:1 and/or 2 (see FIGS. 1 and 2) and CIP2 encoded by SEQ ID NO:6 (see FIG. 4) may have (synergistic) uses in biomass conversion or in other applications for which CBD containing genes are appropriate. Thus, the gene product may find uses in applications such as detergents, textiles, biomass conversion, feed and food applications, and pulp and paper industries.

C. Arabinofuranosidase (ABF2)

It is anticipated that alpha arabinofuranosidase functionality encoded by SEQ ID NO:10 (see FIG. 7) will provide a synergistic effect when used, in combination with xylanase, in applications where it is desirable to hydrolyze xylan based substrates to xylose. The primary xylan hydrolysis would be enhanced by the ability of alpha arabinofuranosidase to remove arabinose side groups, thereby rendering the xylan chains present in various substrates more accessible to xylanase activity.

The above arabinofuranosidase functionality would be of potential benefit in a number of agricultural and industrial applications:

in vivo modification of xylan containing animal feeds to improve digestability.
general applications resulting from biomass degradation to fermentable sugars.
component of enzymatic scouring systems for textiles.
food applications—specifically baking—in combination with other enzymatic functionalities to improve the physical properties of baked goods.

The following preparations and examples are given to enable those skilled in the art to more clearly understand and practice the present invention. They should not be considered as limiting the scope and/or spirit of the invention, but merely as being illustrative and representative thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer achromatography); Ts (tosyl); Bn (benzyl); Ph (phenyl); Ms (mesyl); Et (ethyl), Me (methyl).

EXAMPLES

The following examples are offered to illustrate, but not to limit the claimed invention.

Example 1

Construction of *T. reesei* cDNA Libraries

*T. reesei* (ATCC 13631) was grown under different conditions to generate mycelium expressing growth condition-specific mRNA profiles. The RNA was then isolated, pooled and cDNA libraries were generated.

1A. Growth of *T. Reesei* Mycelia

All cultures were grown in yeast extract/glucose (YEG) liquid medium overnight at 28° C. They were then transferred to the following conditions and cultured for the time stated at 28° C., unless otherwise indicated:

Experiment 1:

A. Vogel's+2% avicel, 3 days and 6 days
B. Vogel's+2% solkafloc, 3 days and 6 days
C. Vogel's+2% wheat bran, 6 days
D. Vogel's+2% beet pulp, 6 days
E. Solid state culture on wheat bran (15 g wheat bran, 1 g Proflo, 1 g solkafloc, 30 ml water), 7 days
F. Solid state culture on beet pulp (15 g beet pulp, 1 g Proflo, 1 g solkafloc, 30 ml water), 9 days Experiment 2:
  A. Vogel's+2% glucose, 24 h
  B. Vogel's+2% lactose, 24 h
  C. Vogel's+2% xylose, 24 h
  D. Vogel's+2% fructose, 24 h
  E. Vogel's+2% maltose, 24 h
  F. Vogel's w/o any carbon added, 24 h
  G. Vogel's w/o any nitrogen added, 24 h
  H. Vogel's+2% wheat bran, 3 days
  I. Vogel's+2% wheat bran, 6 days
  J. Vogel's+2% solkafloc, 3 days
  K. Vogel's+2% solkafloc, 6 days
  L. Vogel's+2% avicel, 3 days
  M. Vogel's+2% avicel, 6 days
  N. Vogels+2% phosphoric swollen cellulose, 3 days
  O, Solid state (15 g wheat bran, 1 g Proflo, 1 g solkafloc, 30 mL water), 6 days
  P. YEG, 42° C. for 1.5 h (heat shock)
  Q. YEG, 20 mM DTT for 1.5 h (redox stress)
  R. YEG, unagitated in closed container for 1.5 h at RT (anoxia)

Media Preparations

| Yeast Extract/Glucose medium - 1 liter | |
| --- | --- |
| 1. $dH_2O$ | 1000 ml |
| 2. Yeast extract | 5 g |
| 3. Glucose | 20 g |

| Vogel's Solution - 1 liter | |
| --- | --- |
| 1. 50X Vogels Stock Solution | 25 ml |
| 2. $dH_2O$ | 975 ml |
| 3. Autoclave | |

| 50X Vogel's Stock Solution - 1 liter | |
| --- | --- |
| 1. $Na_3$ citrate | 150 g |
| 2. $KH_2PO_4$ | 250 g |
| 3. $NH_4NO_3$ | 100 g |
| 4. $MgSO_4 \cdot 7H_2O$ | 10 g |
| 5. $CaCl_2 \cdot 2H_2O$ | 5 g |
| 6. Trace Element Solution | 5 ml |
| 7. Biotin Solution | 2.5 ml |
| 8. in $dH_2O$, bring to a final volume of 1 liter | |

| Trace Element Solution - 1 liter | |
| --- | --- |
| 1. Citric Acid | 50 g |
| 2. $ZnSO_4 \cdot 7H_2O$ | 50 g |
| 3. $Fe(NH_4)_2SO_4 \cdot 6H_2O$ | 10 g |
| 4. $CuSO_4 \cdot 5H_2O$ | 2.5 g |
| 5. $MnSO_4 \cdot 4H_2O$ | 0.5 g |
| 6. $H_3BO_3$ | 0.5 g |
| 7. $NaMoO_4 \cdot 2H_2O$ | 0.5 g |
| 8. in $dH_2O$, bring to a final volume of 1 liter | |

| Biotin Solution - 1 liter | |
| --- | --- |
| 1. d-Biotin | 0.1 g |
| 2. in $dH_2O$, bring to a final volume of 1 liter | |

1B. Isolation of RNA

Total RNA was isolated using Life Technologies™ TRIZOL® Reagent (Catalog No. 15596-026) and a slight modification of its accompanying RNA isolation protocol (incorporated herein in its entirety). Unless otherwise stated, the procedure was carried out at 15 to 30° C.

*T. reesei* mycelium from the different cultures described in 1A was filtered to remove excess liquid and frozen in liquid nitrogen. The frozen mycelium was ground in a mortar and pestle and added to TRIZOL Reagent (approximately 9 ml per 1 ml of ground mycelium). The homogenate was then centrifuged at 12,000×g for 10 minutes at 2 to 8° C. The cleared homogenate solution (supernatant) was transferred to a fresh tube.

The homogenized samples were incubated for 5 minutes at 15 to 30° C. to permit the complete dissociation of nucleoprotein complexes. Then, 0.2 mL of chloroform per 1 mL of TRIZOL Reagent was added and the sample tubes were capped securely. The tubes were shaken vigorously by hand for 15 seconds, then incubated at 15 to 30° C. for 2 to 3 minutes. The samples were then centrifuged at no more than 12,000×g for 15 minutes at 2 to 8° C. Following centrifugation, the mixture separates into a lower red, phenol-chloroform phase, an interphase, and a colorless upper aqueous phase. The aqueous phase (about 60% of the volume of reagent) was then transferred to a fresh tube.

The RNA from the aqueous phase was precipitated by adding 0.25 mL of isopropanol followed by 0.25 mL of a high salt precipitation solution (0.8 M sodium citrate and 1.2 M NaCl) per 1 mL of TRIZOL Reagent used for the homogenization. The resulting solution was mixed and the samples were incubated at 15 to 30° C. for 10 minutes, then centrifuged at no more than 12,000×g for 10 minutes at 2 to 8° C.

The supernatant was removed and the gel-like RNA pellet was washed once with 75% ethanol (made with RNase-free water), using at least 1 mL of 75% ethanol per 1 mL of TRIZOL Reagent used for the initial homogenization. The sample was then mixed by vortexing and centrifuged at no more than 7,500×g for 5 minutes at 2 to 8° C.

The supernatant was again removed and the RNA pellet was briefly dried (air-dry or vacuum-dry for 5-10 minutes). The RNA was dissolved in RNase-free water by passing the solution a few times through a pipette tip and then incubating for 10 minutes at 55 to 60° C.

Purity of the isolated RNA was checked by gel electrophoresis.

1C. Construction of cDNA Library

Equal volumes of RNA obtained from each of the growth conditions described for Experiment 1 in 1A was pooled and a total of 2 mg was forwarded to Life Technologies (Rockville, Md.; now Invitrogen) for construction of a cDNA library. Similarly, RNA from Experiment 2 in 1A was pooled and forwarded to Life Technologies for cDNA construction. The cDNA libraries were produced using standard procedures in the art. The following is a summary of the steps taken.

Poly-A RNA was isolated from the total RNA by chromatography. The total RNA was run on an oligo(dT) cellulose column, and the poly-A RNA (mRNA) was subsequently eluted.

From the mRNA, cDNA were generated by Life Technologies (Rockville, Md.) using the Life Technologies™ cDNA Synthesis System (the Instruction Manual for which is hereby incorporated in its entirety). The following outlines procedures to be used.

First Strand Synthesis

Reaction components for production of a first strand of cDNA from the isolated *T. reesei* mRNA are combined in a 1.5 ml microcentrifuge tube on ice. The reaction mixture, in a volume of 50 µl, contains the following components:
  50 mM Tris-HCl (pH 8.3)
  75 mM KCl
  3 mM $MgCl_2$
  10 mM DTT
  500 µM each dATP, dCTP, dGTP and dTTP
  50 µg/ml oligo(dT)$_{12-18}$
  100 µg/ml poly (A) RNA (from *T. reesei*)
  10,000 units/ml Moloney Murine Leukemia Virus (M-MLV) reverse transcriptase The reverse transcriptase is added last, with mixing, to initiate the reaction. Optionally, a 10 µl aliquot is immediately removed and transferred to a separate tube containing 1 µCi [∝-$^{32}$P]dCTP tracer. Both tubes are then incubated at 37° C. for 1 hour. The tubes are placed back on ice after incubation and the reaction is terminated by adding 1 µl of 0.25 M Na$_2$EDTA (pH 7.5). The 40 µl reaction mixture is used for second strand cDNA synthesis.

If made, the tracer mixture is diluted with 89 µl water and duplicate 5 µl aliquots are spotted onto filters (e.g., glass fiber filters). The second filter is washed three times (sequentially), 5 minutes each, with about 50 ml per wash of ice-cold TCA. The second filter is then washed with 50 ml of 95% ethanol for about 5 minutes at room temperature, then dried. The two filters are counted in standard scintillant to determine the amount of $^{32}$P in the mixture (from the first filter) and the amount of $^{32}$P incorporated in the first strand cDNA (from the second filter) to determine the yield of first strand cDNA.

The remainder of the tracer mixture is extracted with phenol and ethanol precipitated. The pellet is isolated and gel electrophoresis using alkaline agarose gel is performed to determine the size of the single strand products.

Second Strand Synthesis

Double stranded cDNA may be produced using a procedure tailored for the production of cDNA to which linkers will be added.

In a 1.5 ml microcentrifuge tube on ice, components are added to 40 µl of the first strand reaction product to produce 300 µl of a second strand reaction mixture. The components are added in the following order: DEPC-treated water, dNTP mixture, concentrated buffer/salt solution, *E. coli* DNA polymerase I, *E. coli* RNase H and *E. coli* DNA ligase. The final reaction mixture has the following composition, in addition to the original components in the first strand reaction product:

25 mM Tris-HCl (pH 8.3)
100 mM KCl
10 mM (NH$_4$)$_2$SO$_4$
5 mM MgCl$_2$
250 µM ea. dATP, dCTP (including 10 µCi of [∝-$^{32}$P] dCTP), dGTP, dTTP
0.15 mM NAD
5 mM DTT
250 U/ml DNA polymerase I
8.5 U/ml RNase H
30 U/ml DNA ligase The tube is vortexed gently to mix and incubated at 16° C. for 2 hours. The tube is then placed on ice and 25 µl of Na$_2$EDTA (pH 7.5) is added.

A 10 µl amount of the mixture is added to 90 µl water. A 5 µl aliquot of this is spotted onto a first glass fiber filter and dried. Another 10 µl amount of the undiluted mixture is spotted onto a second glass fiber filter, which is washed three times, 5 minutes each, with 50 ml ice-cold TCA each wash. The second filter is then washed once at room temperature with 95% ethanol for 5 minutes. The filters are counted in standard scintillant, the first to be used to determine the amount of $^{32}$P in the mixture (specific activity) and the second to be used to determine the amount of $^{32}$P incorporated into the cDNA.

The remainder of the reaction mixture is extracted in phenol and precipitated with ethanol. The pellet is then dissolved in 200 µl of sterile TE buffer (10 mM Tris-HCl (pH 7.5), 1 mM Na$_2$EDTA), to which 100 µl of 7.5 M ammonium acetate, followed by 500 µl of ethanol are then added to precipitate. The pellet is dried, then dissolved in 20 µl of sterile TE buffer. 2 µl are removed and analyzed by alkaline agarose gel electrophoresis. Linkers or adapters are added to the remainder for incorporation into a vector.

For linker addition, the cDNA is first methylated with a methylase specific for the linker to be used to protect internal restriction sites. The termini of the cDNA are repaired with T4 DNA polymerase, and linkers are then added by blunt end ligation. Linkers should be provided at a high concentration for efficient addition. The cDNA is digested with the selected restriction endonuclease(s), then purified from the small digestion products (e.g., by column chromatography). The vector is digested with the same restriction endonuclease(s) and combined with the cDNA, which are then ligated into the vector as an insert.

The linkers or adapters added to the cDNA contained restriction endonuclease sites such that a SalI site is found 5' to the cDNA sequence corresponding to the original mRNA and a NotI site 3' to the cDNA sequence corresponding to the original mRNA. The cDNA were then inserted into a pREP3Y shuttle vector. The pREP3Y vector is a modified pREP3X vector (ATCC number 87603), wherein the vector was digested with BamHI endonuclease, and a synthetic oligonucleotide inserted to add restriction sites. The resulting vector has the following restriction sites in the polylinker region: Xho1, SalI, XbaI, BamHI, SmaI, NotI and SmaI. The vector and cDNA were digested with SalI/NotI and the cDNA inserted into the vector. See FIG. 15.

cDNA libraries were constructed by Invitrogen Life Technologies in the vector pREP3Y. *E. coli* strain DH12S was transformed with the vector to create the cDNA library. An unamplified library was returned to the inventors. Individual clones were then plated and grown on LA plus 50 mg/ml carbenicillin (Bacto tryptone, 20 g/l; Bacto yeast extract, 10 g/l; NaCl, 1 g/l; Bacto agar, 17.5 g/l; 1 ml/l of 50 mg/ml carbenicillin added after sterilization by autoclave and cooling but prior to solidification).

Example 2

Identification of LT1-24 and the cip1 Gene

The following rationale was used to find the cip1 gene: 1) Grow the library on Hybond+ membranes from Amersham; 2) Lyse the cells and fixate the library DNA on the membrane; 3) Hybridize the blot with the gene specific probes; 4) Hybridize the blot a second time, but now with a mixed CBM probe; 5) Subtract the gene specific from the CBM spots; and Select and analyze the new spots.

Colony Isolation

The cellulose induced cDNA library from *T. reesei* was used for these hybridization experiments. The *E. coli* cDNA library was plated out on agar plates (20×20 cm) to obtain a sufficient amount of clones.

cDNA libraries were plated on 200 ml 2×TY (Bacto-Trypton 16 g/l, Yeast Extract 10 g/l, NaCl 5 g/l) solidified with 1.5% agar in the presence of 100 µg/ml ampicillin (AMP). Efficient picking can be obtained when 1500 cfu are plated on 20×20 cm agar plates (Genetix, Q-Tray). 1 ml of the appropriate dilution was plated using glass beads. Plates were grown overnight at 37° C.

Colonies were picked and transferred to microtiter plates using a Q-Pix (Genetix Ltd.).

This resulted in the growth and storage of 45312 clones. The microtiter plates can be stored at −80 C with 10% glycerol until ready for use. From these *T. reesei* cDNA containing clones 34500 clones were arrayed on nylon membranes and used for hybridization experiments.

The Q-Pix (Genetix Ltd.) is used for picking of the clones into 384-well MTPs. After growth, the Q-Pix is used for the gridding of the 384-well MTPs on membrane filters. These membrane filters were used for hybridization experiments with CBM containing probes to search for novel CBM containing cellulases.

Probe Preparation

Probes were generated using primers as specified in Table 1. The CBM probes were designed using known sequences of Trichoderma reesei carbohydrate binding modules. See Paul Birch, Curr. Genet (1998) 33; 70-76. Briefly, for CBM probes total T. reesei QM6A genomic DNA (100 ng/50 µl) was mixed with 10 µM 1 µl/50 µl volume FRG164 and 100 µM 1 µl/50 µl volume FRG165, FRG166 or FRG167. FRG166 resulted in no amplification (Ser codon was AGY) while FRG167 resulted in amplification (Ser codon was TCN). Thus, the FRG167 primer was used in the amplification. This fragment was mixed with the fragment produced with FRG165 as primer. The two separate fragments were mixed and contained a mix of CBM sequences present in T. reesei and used as the CBM probe. In summary: the CBM probe has been prepared by mixing the fragments obtained by PCR using the combinations: FRG164+FRG165 and FRG164+FRG167, 2.5 units platinum TAQ polymerase, 5 µl 10×TAQ buffer, 1.5 µl MgCl2 and 1 µl 10 mM dNTP's. The PCR was performed as follows:

1 cycle:
 1 minute at 98° C.
10 cycles:
 1 minute at 94° C.
 1.5 minutes at 65-50° C.
 1 minute at 72° C.
25 cycles:
 1 minute at 94° C.
 1.5 minutes at 50° C.
 1 minute at 72° C.
 stop the reaction and store at 15° C.

For catalytic core (i.e., gene specific) probes, total T. reesei QM6A genomic DNA (100 ng/50 µl) was mixed with 1 µl of 10 mM primer concentration in a total volume of 50 µl, 2.5 units platinum TAQ polymerase, 5 µl 10×TAQ buffer, 1.50 MgCl2 and 1 µl 10 mM dNTP's using the above protocol, but instead of 50° C., 55° C. has been used.

The probes were purified using standard methods. In this series of experiments, the probes were purified by gel purification using Qiagen gel purification KIT.

Detection

Colony samples picked from the microtiter plates were spotted on 20×20 cm nylon membrane filters (Hybond+ (RPN.82B), Amersham) and grown overnight at 37° C. after placing the filters on large agar 2×TY (100 µg/ml ampicillin). Each 20×20 cm membrane contained 4600 clones in duplicate. Plates were then processed by ECL according to manufacturer's instructions for the presence of either the gene specific or CBM sequences.

Prehybridization was performed in ECL buffer provided with the ECL Direct kit for 20 minutes during which time the probe was labeled (exactly according to the protocol). Probe was added directly to the prehybridization solution to a concentration of 10 ng/ml and hybridized for about 60 minutes at 42° C. The filters were then washed twice in primary buffer (6M urea, 0.5×SSC, 0.4% SDS) at 42° C. for 20 minutes/wash and twice in secondary buffer (2×SSC) at room temperature for 5 minutes/wash. After draining excess wash buffer, detection was carried out by adding an equal volume mixture of ECL detection reagents directly to the filters to 0.125 ml/cm2. After one minute, excess reagent was drained, the membranes wrapped in SaranWrap™ and exposed to Hyperfilm™ ECL (RPN.2 103) for less than two hours, typically for 10 minutes. Colonies showing positive signal were then selected for further analysis by other methods such as sub-cloning, DNA sequencing, restriction mapping and PCR.

Because the ECL system utilizes an enzyme label, and this becomes inactivated following the chemiluminescent reaction, it is not necessary to strip the blot of old probe before starting second and subsequent hybridization. The blot should be kept in detection reagent over night before reprobing the blot according to the described protocol.

All 9 gene specific probes, i.e., probes for the catalytic modules, were mixed and used as a "mega"-probe. After this hybridization the same blots were re-used and hybridized with the CBM probe. By subtracting the spots of the "mega"-probe from the CBM's, the unknowns were detected. Total of 34500 clones have been screened; 264 clones have been cherry picked and probed with specific catalytic probes; 20 clones hybridized with a gene specific probe from LT1-24. The primers used were as follows: Forward primer: P002248: GAC AAT CCA AAC GAC GCT (SEQ ID NO:28); and Reverse primer: PVS173: CAA TCG AGA TGT CGT CGA AC (SEQ ID NO:29).

One clone, LT1-24, comprising cip1, was identified that gave a signal when probed with a mixed pool of CBM probes but failed to generate a signal when probed with the pooled catalytic domain probes. Thus, subtraction hybridization resulted in the identification of a novel CBM containing T. reesei gene, cip1. The complete sequence of the cDNA of this gene was determined using techniques well known in the art. It has a predicted secretion signal, a "catalytic" region of unknown function, a linker region and a C-terminal cellulose binding module (CBM).

TABLE 1

Gene-specific (catalytic domain) and degenerate (CBM) primers of the known CBM containing genes in T. reesei (Chromosomal DNA: QM6A).

gene (catalytic domain) specific primers

| Gene | orientation | Primer sequence |
|---|---|---|
| cbh1 | forward | FRG168 CTC CTC CAC ACC CGG TGC CG (SEQ ID NO: 30) |
|  | reverse | FRG169 TGC TGC CAA TGG GTC CG (SEQ ID NO: 31) |
| cbh2 | forward | FRG170 ACG TAT TCA GGC AAC CC (SEQ ID NO: 32) |
|  | reverse | FRG171 GCA GTG GCC ATG GCT CC (SEQ ID NO: 33) |
| egl1 | forward | FRG172 CCA GTA CAT GAA CTG GC (SEQ ID NO: 34) |
|  | reverse | FRG173 AGA CCC AAT GTC TCC CC (SEQ ID NO: 35) |
| egl2 | forward | FRG184 CGA ATT GTG CTC CTG GC (SEQ ID NO: 36) |
|  | reverse | FRG185 GTG GTT GGA CCG GAT GG (SEQ ID NO: 37) |

TABLE 1-continued

Gene-specific (catalytic domain) and degenerate (CBM) primers of the known CBM containing genes in T. reesei (Chromosomal DNA: QM6A).

```
egl4    forward   FRG176 CCT ACC GTG GTA TCA GG  (SEQ ID NO: 38)
        reverse   FRG177 TGG TTC TGC TGG TCG GG  (SEQ ID NO: 39)

egl5    forward   FRG178 CAT TTC GAC ATC ATG GC  (SEQ ID NO: 40)
        reverse   FRG179 CTG TCC CAC GCA GAG GC  (SEQ ID NO: 41)

axe1    forward   FRG180 CCG GCT GGC TTC GTC TG  (SEQ ID NO: 42)
        reverse   FRG181 TGG CCG TAA CCT TGG TG  (SEQ ID NO: 43)

man1    forward   FRG182 CCT CTC TCA CGA CTC GC  (SEQ ID NO: 44)
        reverse   FRG183 GTT CGA TGA GTT GTA CC  (SEQ ID NO: 45)

swo1    forward   PVS159 CCC CCA AAC GGA ACA ACT TCC  (SEQ ID NO: 46)
        reverse   PVS160 CTG TAT CTG TGG TTG TGT AGG  (SEQ ID NO: 47)
```

CBM degenerate primers

| Box | orientation | Primer sequence | deg. |
|---|---|---|---|
| GQCGG | Forward | FRG164 GGN CAR TGY GGN GG (SEQ ID NO: 48) | 64X |
| YSQC(L/I) | Reverse | FRG165 AD RCA YTG NGA RTA (SEQ ID NO: 49) | 96X |
| YSQC(L/I) | Reverse | FRG166 AD RCA YTG RCT RTA (SEQ ID NO: 50) | 32X |
| YAQC(L/I) | Reverse | FRG167 AD RCA YTG NGC RTA (SEQ ID NO: 51) | 96X |

N (= A or C or G or T),
R (= A or G)
Y (= C or T),
D (= G or A or T)

Example 3

Identification and Sequence Analysis of *T. reesei* Genes of Interest

Partial sequencing of anonymous cDNA clones is a widely used technique for gene identification. These partial cDNA sequences, or Expressed Sequence Tags (ESTs) have potential application for the identification of important genes involved in cellulose degradation.

The plasmid containing a cDNA insert was isolated from clones of the libraries described in Example 1 and a single pass 5' sequence of the cDNA insert was obtained from approximately 18,000 clones at North Carolina State University (Fungal Genomics Laboratory, College of Agriculture and Life Sciences, Raleigh, N.C.). Sequences of the cDNA were obtained using a primer corresponding to the vector sequence adjacent to the 5' end of the cDNA insert. The sequences of individual sequence reads were compared and overlapping segments were assembled to form 2101 contigs consisting of two or more reads. 3030 individual reads did not have significant sequence overlap with any other reads in the data set. The predicted coding regions of the EST set were compared by BLAST (See Altschul et al. 1990. Basic local alignment search tool. J. Mol. Biol. 215:403-410) to all publicly available sequence databases.

Clones containing cDNA sequences similar to known glycosyl hydrolases, carbohydratre esterases or carbohydrate binding modules were identified for further investigation using the BLAST program (BLASTX and BLASTN) using default parameters. See Altschul et al., 1990. Basic local alignment search tool. J. Mol. Biol. 215:403-410. Full-length cDNAs corresponding to these gene products were sequenced in their entirety using techniques well known in the art.

Sequences were analyzed using the DNAstar or Vector NTI software package using default parameters.

Genes of interest identified by this method are shown in Table 2.

TABLE 2

Biomass degrading activities and their genes in *Trichoderma reesei*

| Gene | Family[a] | Function[b] | Features[c] | Accession # |
|---|---|---|---|---|
| axe2 | CE5 | Acetyl xylan esterase | SS, GPI | AY281376 |
| cip2 | Unassigned | Unknown | SS, CBM | AY281368 |
| abf2 | GH62 | Arabinofuranosidase | SS | AY281369 |
| cip1 | Unassigned | Unknown | SS, CBM | AY281370 |

[a]GH, glycosyl hydrolase family; CE, carbohydrate esterase family.
[b]Function of proteins identified in this study is predicted from encoded amino acid sequence.
[c]SS, N-terminal signal sequence; CBM, carbohydrate binding module; GPI, glycosyl phosphatidyloinositol anchor. Features of proteins identified in this study are predicted from encoded amino acid sequence.

Example 4

Co-Regulation of the cip1 and cip2 Genes with Other Cellulase Genes

Previously identified endoglucanases are induced during growth on media containing cellulose, sophorose or lactose. To determine whether the newly discovered polypeptides, CIP1 and CIP2, with putative roles in biomass degradation are similarly regulated, we examined mRNA levels for each of these gene products by Northern blot. Two different strains were used: QM6a, a wild type isolate of *T. reesei* and RL-P37, a strain that has been selected for improved production of cellulolytic enzymes. Mycelia from each of these strains were grown in flasks in minimal media containing glucose, crystalline cellulose (avicel), or glycerol as the sole carbon source, or glycerol supplemented with 1 mM sophorose.

Microarrays were used to examine the regulation of the cip1 and cip2 genes.

Generation of mRNA

*Trichoderma reesei* strains used were obtained from the American Type Culture collection.

For Northern blot analysis, ~1×10$^7$ spores were inoculated into 50 ml minimal medium supplemented with 5% glucose and grown for 24 hours. Mycelia were collected by centrifugation, washed in carbon-free medium and resuspended to an optical density of ~0.3 in 50 ml minimal medium supplemented with 5% glucose, 2% avicel, 2% glycerol or 2% glycerol containing 1 mM sophorose (Sigma). Cultures were grown at 30° C. in flasks with vigorous aeration for 20 hours.

Mycelia were harvested by filtration through miracloth and were quick frozen in liquid nitrogen. RNA was prepared from the mycelia by grinding under liquid nitrogen with a mortar and pestle and extracting using Trizol reagent (Invitrogen Life Technologies) according to manufacturers instructions. Polyadenylated RNA was selected 2 times using Oligotex (Qiagen). Blotting was performed using a NorthernMax-Gly Kit (Ambion). $^{32}$P-labelled probes were generated using aDECAprime Kit (Ambion). Hybridization was performed using ULTRAhyb Ultrasensitive Hybridization Buffer (Ambion).

The known *T. reesei* endoglucanases are induced during growth on media containing cellulose, sophorose or lactose. To determine whether cip1 is similarly regulated, we examined mRNA levels for the endoglucanases egll, eglll and cip1 by Northern blotting. Two different strains were used: QM6a, a wild type isolate of *T. reesei* and RL-P37, a strain that has been selected for improved production of cellulolytic enzymes. Mycelia from each of these strains were grown in flasks in minimal media containing glucose, crystalline cellulose (avicel), or glycerol as the sole carbon source, or glycerol supplemented with 1 mM sophorose. As shown in FIG. 13, the endoglucanases were regulated very similarly to one another and to cip1. Induction by sophorose resulted in much higher levels of expression than did growth on cellulose over the time period examined. In addition, expression of these genes was substantially higher in the strain RL-P37 than it was in QM6a.

Microarrays

To measure the expression levels of cip1 and cip2 microarrays were constructed. Sixty by oligonucleotide probes containing unique sequences from within each of the ESTs were designed to query the abundance of their corresponding mRNAs. The oligonucleotide probes were synthesized and arrayed as described in Hughes et al. (2001) Nature Biotechnol 19:342-347 by Agilent Technologies, Palo Alto, Calif. In all of the experiments performed the microarrays were used to determine the relative expression levels between two different samples.

mRNAs comprising the samples of interest were labeled with Cy5 and Cy3 fluorescent dyes Perkin Elmer/NEN. Reciprocally labeled pairs of samples were combined and co-hybridized to the arrays. The log of the ratio (log ratio) of the two fluorescent species bound to each of the probes reflects the relative expression levels of the cognate genes in the two samples. See Hughes et al. (2001), supra, and DeRisi et al. (1996) Nat Genet. 14:457-460.

Although the two putative glycolytic enzymes, cip1 and cip2, do not fit into any currently defined class of GHs their regulation parallels known GHs. The regulation of cip1 among strains with varying cellulase-producing capabilities and across a variety of conditions is indistinguishable from the endoglucanases and particularly the cellobiohydrolase cbh1/cel7a (FIGS. 13 and 14). Similarly, cip2 has a pattern of expression in common with these genes, particularly in RL-P37. The coregulation of these genes with canonically-regulated cellulase components and the fact that they contain distinct cellulose-binding modules furthers the notion that cip1 and cip2 encode previously unrecognized activities with potential roles in biomass degradation.

The hemicellulase-encoding genes axe2 and abf2 appear to be differentially induced by lactose and by sophorose in either QM6a or in RL-P37 or both. Most notably, abf2, was substantially more induced in RL-P37 during growth on lactose than in sophorose. (Data not shown.)

This shows that the novel genes, cip1 and cip2, are regulated in a coordinate fashion with other cellulose degrading enzymes.

Example 5

Construction of a Strain of *Trichoderma reesei* Deleted for Four Cellulase Genes (Quad Delete)

This example describes the construction of a suitable expression host. More specifically, described in this example is the construction of a *Trichoderma* expression host that has had the major cellulase genes deleted. The methods used herein have been described previously in, for example, U.S. Pat. Nos. 5,650,322, 5,874,276 and 6,286,196.

We have constructed a strain of *T. reesei* in which the genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated by deletion or disruption using molecular genetic techniques. This strain (a quad delete strain) is useful as a host for overexpression of genes encoding other *T. reesei* secreted proteins.

The *T. reesei* host strain used was strain RL-P37 which has previously been used to manufacture commercial cellulase preparations by Genencor International, Inc. The derivation and characterisation of this strain has been published previously (Sheir-Neiss, G. and Montenecourt, B. S. (1984) Appl. Microbiol. Biotechnol. 20:46-53; U.S. Pat. No. 4,797,361). It is a cellulase over-producing mutant strain which has been obtained as a result of several mutagenesis steps from the wild-type strain (QM6a).

1) Isolation of a pyr4 Mutant Strain.

In order to prepare strain RL-P37 for transformation with plasmid DNA it was necessary to isolate a derivative having a null mutation in the pyr4 gene.

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 mutant strains using FOA. In practice, spores of *T. reesei* strain RL-P37 were spread on the surface of a solidified medium containing 2 mg/ml uridine and 1.2 mg/ml FOA. Spontaneous FOA-resistant colonies appeared within three to four days. We subsequently identified those FOA-resistant mutants which required uridine for growth. In order to identify those mutants which specifically had a defective pyr4 gene protoplasts were generated and transformed with a plasmid containing a wild-type pyr4 gene (Smith, J. L., Bayliss, F. T. and Ward, M. (1991) Curr. Genet. 19:27-33). Following transformation protoplasts were plated on medium lacking uridine. Subsequent growth of transformed colonies demonstrated complementation of a defective pyr4 gene by the plasmid-borne pyr4 gene. In this way strain GC69 was identified as a pyr4 mutant of strain RL-P37.

2) Construction of a Plasmid Designed to Delete the CBHI Encoding Gene.

The cbh1 gene, encoding the CBHI protein, was cloned from the genomic DNA of strain RL-P37 by hybridization with an oligonucleotide probe designed on the basis of the published sequence for this gene (Shoemaker, S., Schweickart, V., Ladner, M., Gelfand, D., Kwok, S., Myambo, K. and Innis, M. (1983) Biotechnology 1:691-696). The cbh1 gene resides on a 6.5 kb PstI fragment and was inserted into the PstI site of pUC4K (Pharmacia Inc., Piscataway, N.J., USA) replacing the kanamycin-resistance gene of this vector. The resulting plasmid, pUC4K::cbh1, was then cut with HindIII and the larger fragment was isolated and religated to give pUC4K::cbh1ΔH/H. This procedure removed the entire cbh1 coding sequence and approximately 1.2 kb of 5' and 1.5 kb of 3' flanking sequences. Approximately 1 kb of flanking DNA remained from either end of the original PstI fragment.

The T. reesei pyr4 gene was cloned as a 6.5 kb HindIII fragment of genomic DNA in pUC18 to form pTpyr2 (Smith, J. L., Bayliss, F. T. and Ward, M. (1991) Curr. Genet. 19:27-33). The plasmid pUC4K::cbh1ΔH/H was cut with HindIII and the ends were dephosphorylated with calf intestinal alkaline phosphatase. This DNA was ligated with the 6.5 kb HindIII fragment containing the pyr4 gene to give pΔCBHIpyr4.

Digestion of pΔCBHIpyr4 with EcoRI liberated a larger fragment which consisted of flanking regions of the cbh1 locus at either end with the pyr4 gene replacing the cbh1 coding sequence in the center. The only DNA on this fragment which was not derived from T. reesei was a 21 by fragment derived from the multiple cloning site of pUC4K.

3) Deletion of the cbh1 Gene of T. reesei.

Protoplasts isolated from mycelium of strain GC69 were transformed with EcoRI digested plasmid pΔCBHIpyr4 using methods outlined by Smith et al., 1991. Stable transformants were obtained and those from which the cbh1 gene had been deleted were identified as described below.

Total DNA was isolated from the transformants, digested with PstI, subjected to agarose gel electrophoresis and blotted to a membrane filter. The filter was then hybridised with $^{32}$P labelled pΔCBHIpyr4 and the pattern of hybridisation observed by autoradiography. This probe hybridised with the native cbh1 and pyr4 genes in an untransformed strain. In one transformant (strain P37PΔCBHI) a pattern of hybridisation was observed which would be predicted if a double cross-over integration event had occurred. That is, the cbh1 gene had been deleted by integration of a single copy of the larger EcoRI fragment obtained from pΔCBHIpyr4 at the cbh1 locus of strain RL-P37.

Southern analysis was also performed as above except that the probe used was radiolabelled pIntCBHI. This plasmid consists of a pUC vector containing a 2 kb BglII fragment from the cbh1 locus within the region that was deleted in pUC4K::cbh1ΔH/H. This plasmid hybridised to the cbh1 locus of strain GC69 but did not hybridise to DNA from strain P37PΔCBHI. This confirms that the cbh1 gene had been deleted and that the pUC DNA fragment from pΔCBHIpyr4 had not been incorporated by the deleted strain.

Analysis of secreted proteins by separation on isoelectric focusing gels showed that the CBHI protein was not produced by strain P37PΔCBHI.

4) Generation of a pyr4 Null Mutant of P37PΔCBHI.

Spores of the transformant (P37PΔCBHI) which was deleted for the cbh1 gene were spread onto medium containing FOA. A pyr4 deficient derivative of this transformant was subsequently obtained using the methods described in section 1 above. This pyr4 deficient strain was designated P37PΔCBHIPyr⁻26. Southern analysis has shown that a spontaneous deletion had occurred when strain P37PΔCBHIPyr⁻26 was selected. This deletion completely removed the pyr4 gene which had integrated at the cbh1 locus in strain P37PΔCBHI, as well as flanking DNA from the cbh1 locus beyond the extent of the 6.5 kb PstI fragment of genomic DNA which was originally cloned.

5) Construction of a Vector Designed to Delete the cbh2 Gene.

The cbh2 gene of T. reesei, encoding the CBHII protein, has been cloned as a 4.1 kb EcoRI fragment of genomic DNA (Chen et al., 1987, Biotechnology 5:274-278). This 4.1 kb fragment was inserted between the EcoRI sites of pUC4XL. The latter plasmid is a pUC derivative (constructed by R. M. Berka, Genencor International Inc.) which contains a multiple cloning site with a symmetrical pattern of restriction endonuclease sites arranged in the order shown here. EcoRI, BamHI, SacI, SmaI, HindIII, XhoI, BglII, ClaI, BglII, XhoI, HindIII, SmaI, SacI, BamHI, EcoRI. The plasmid, pPΔCBHII was constructed in which a 1.7 kb central region of this cbh2 clone, between a HindIII site (at 74 by 3' of the CBHII translation initiation site) and a ClaI site (at 265 by 3' of the last codon of CBHII), has been removed and replaced by a 1.6 kb HindIII-ClaI DNA fragment containing the T. reesei pyr4 gene obtained as follows. The T. reesei pyr4 gene was excised from pTpyr2 on a 1.6 kb NheI-SphI fragment and inserted between the SphI and XbaI sites of pUC219 (derived from pUC119 by expanding the multiple cloning site to include restriction sites for BglII, ClaI and XhoI; Wilson et al., 1989, Gene 77:69-78) to create p219M (Smith et al., 1991, Curr. Genet. 19:27-33). The pyr4 gene could then be removed as a HindIII-ClaI fragment having seven by of DNA at one end and six by of DNA at the other end derived from the pUC219 multiple cloning site and inserted into the HindIII and ClaI sites of the cbh2 gene to form the plasmid pPΔCBHII.

Digestion of this plasmid with EcoRI liberated a fragment having 0.7 kb of flanking DNA from the cbh2 locus at one end, 1.7 kb of flanking DNA from the cbh2 locus at the other end and the T. reesei pyr4 gene in the middle. The only DNA in this fragment which was not derived from T. reesei was the 6 by and 7 by fragments of the pUC219 multiple cloning site at either end of the pyr4 gene.

6) Deletion of cbh2 gene from strain P37PΔCBHIPyr⁻26.

Protoplasts of strain P37PΔCBHIPyr⁻26 were generated and transformed with EcoRI digested pPΔCBHII according to the methods outlined in 3 above. Stable transformants were cultured in shake flasks and the protein in the culture supernatants was examined by isoelectric focussing. One transformant (designated P37PΔΔCBH67) was identified which did not produce any CBHII (nor CBHI) protein.

DNA was extracted from strain P37PΔΔCBH67, digested with EcoRI and Asp718, and subjected to agarose gel electrophoresis. The DNA from this gel was blotted to a membrane filter and hybridized with $^{32}$P labelled pPΔCBHII. The 4.1 kb EcoRI fragment containing the wild-type cbh2 gene was observed in the DNA from an untransformed control strain. In contrast, in strain P37PΔΔCBH67 the single 4.1 kb band was eliminated and replaced by two bands of approximately 0.9 and 3.1 kb. This is the expected pattern if a single copy of the larger EcoRI fragment from pPΔCBHII had integrated precisely at the cbh2 locus and deleted the cbh2 gene.

The same DNA samples were also digested with EcoRI and Southern analysis was performed as above. In this example the probe was $^{32}$P labelled pIntCBHII. This plasmid contains a portion of the cbh2 gene coding sequence from within that segment of cbh2 DNA which was deleted in plasmid pPΔCBHII. No hybridization was seen with DNA from strain P37PΔCBH67 confirming that the cbh2 gene was deleted and that the pUC plasmid fragment of pPΔCBHII had not been incorporated by this strain.

7) Selection of a pyr4 Null Mutant of Strain P37PΔΔCBH67.

Spores of the transformant (P37PΔΔCBH67) which was deleted for both the cbh1 and cbh2 genes were spread onto medium containing FOA. A pyr4 deficient derivative of this transformant was subsequently obtained using the methods described in section 1 above. This pyr4 deficient strain was designated P37PΔΔCBH67Pyr⁻1. Southern analysis has shown that a spontaneous deletion had occurred when strain P37PΔΔCBH67Pyr⁻1 was selected. This deletion completely removed the pyr4 gene which had integrated at the cbh2 locus in strain P37PΔΔCBH67, as well as flanking DNA from the cbh2 locus beyond the extent of the 4.1 kb EcoRI fragment of genomic DNA which was originally cloned. The short (6 by and 7 bp) fragments of DNA derived from the pUC219 multiple cloning site which were present at either end of the pyr4 gene would also have been removed from the genome by this deletion.

8) Construction of a Plasmid Designed to Disrupt the egl2 Gene.

The egl2 gene, encoding EGII (previously referred to as EGIII by some), has been cloned from *T. reesei* and the DNA sequence published (Saloheimo et al., 1988, Gene 63:11-21). We have obtained the gene from strain RL-P37 as an approximately 4 kb PstI-XhoI fragment of genomic DNA inserted between the PstI and XhoI sites of pUC219. The *T. reesei* pyr4 gene, present on a 2.7 kb SalI fragment of genomic DNA obtained from pTpyr2, was inserted into a SalI site within the EGII coding sequence to create plasmid pEGII::P-1. This resulted in disruption of the EGII coding sequence but without deletion of any sequences. The plasmid, pEGII::P-1, can be digested with HindIII and BamHI to yield a linear fragment of DNA derived exclusively from *T. reesei* except for 5 by on one end and 16 by on the other end both of which are derived from the multiple cloning site of pUC219.

9) Disruption of the egl2 Gene of Strain P37PΔCBH67Pyr⁻1.

Strain P37PΔΔCBH67Pyr⁻1 was transformed with pEGII::P-1 which had been previously digested with HindIII and BamHI and stable transformants were selected. Total DNA was isolated from transformants and Southern analysis used to identify strains in which the fragment of plasmid DNA containing the pyr4 and egl2 genes had integrated at the egl2 locus and consequently disrupted the EGII coding sequence. Southern analysis was performed using as a probe an approximately 4 kb PstI fragment of *T. reesei* DNA containing the egl2 gene. When DNA isolated from strain P37PΔΔ67P⁻1 was digested with PstI for Southern analysis the egl2 locus was subsequently visualised as a single 4 kb band on the autoradiograph. However, for a transformant disrupted for the egl2 gene this band was lost and was replaced by two new bands as expected. When the DNA was digested with BglII or EcoRV the size of the band corresponding to the egl2 gene increased in size by approximately 2.7 kb (the size of the inserted pyr4 fragment) between the untransformed P37PΔΔ67P⁻1 strain and the transformant disrupted for egl2. This latter transformant, now deleted for the cbh1, cbh2, and egl2 genes, was designated as strain B31. Further Southern analysis confirmed that the pUC DNA fragment of pEGII::P-1 was not incorporated in this strain.

10) Selection of a pyr4 Null Mutant of Strain B31.

Spores of the transformant (B31) which was deleted for the cbh1, cbh2 and egl2 genes were spread onto medium containing FOA. A pyr4 deficient derivative of this transformant was subsequently obtained using the methods described in section 1 above. This pyr4 deficient strain was designated B31P6. Southern analysis has shown that a spontaneous deletion had occurred when strain B31P6 was selected. This deletion removed the majority of the pyr4 gene which had integrated at the egl2 locus in strain B31, but did not extend into the flanking DNA of the egl2 locus.

11) Construction of a Plasmid Designed to Delete the egl1 Gene.

The egl1 gene of *T. reesei* has been cloned and the DNA sequence of the gene has been published (Penttila et al., 1986, Gene 45:253-263; van Arsdell et al., 1987, Bio/technology 5:60-64). We have obtained this gene from *T. reesei* strain RL-P37 as a 4.2 kb HindIII fragment of genomic DNA inserted at the HindIII site of pUC100 (a derivative of pUC18 with an oligonucleotide inserted into the multiple cloning site adding restriction sites for BglII, ClaI and XhoI) to give pUCEGI. An approximately 1 kb EcoRV fragment extending from a position close to the middle of the EGI coding sequence to a position beyond the 3' end of the coding sequence was removed and replaced by a 3.5 kb ScaI fragment of *T. reesei* DNA containing the pyr4 gene obtained from pTpyr2. The resulting plasmid was called pPΔEGI.

The plasmid, pPΔEGI could be digested with HindIII to release a DNA fragment comprising only *T. reesei* genomic DNA having a segment of the egl1 gene at either end and the pyr4 gene, replacing part of the EGI coding sequence, in the center.

12) Deletion of the egl1 Gene in Strain B31P6.

Two forms of pPΔEG1 were constructed which differed only in the orientation of the pyr4 gene with respect to the egl1 flanking regions. Strain B31P6 was transformed with a mixture of both forms of the plasmid after they had been digested with HindIII. Total DNA was extracted from stable transformants, digested with HindIII and subjected to Southern analysis. The probe used was radio-labelled pUCEGI. Hybridisation was observed to a 4.2 kb fragment of DNA from strain B31P6 representing the undeleted egl1 gene. A transformant (strain 1A52) was identified in which this 4.2 kb was no longer present but had been replaced by a fragment of approximately 6.8 kb. This is the pattern expected if the larger HindIII fragment from pPΔEGI had integrated precisely as predicted at the egl1 locus leading to deletion of part of the EGI coding sequence and insertion of pyr4 at this position. Using a pUC plasmid as a probe for Southern analysis it was confirmed that the pUC DNA fragment of pPΔEGI had not been incorporated in strain 1A52.

Example 6

Construction of the pTrex3g Expression Vector

This example describes the construction of the basic vector used to express the genes of interest.

This vector is based on the *E. coli* vector pSL1180 (Pharmacia Inc., Piscataway, N.J., USA) which is a pUC118 phagemid based vector (Brosius, J. (1989) DNA 8:759) with an extended multiple cloning site containing 64 hexamer restriction enzyme recognition sequences. It was designed as a Gateway destination vector (Hartley, J. L., Temple, G. F. and Brasch, M. A. (2000) Genome Research 10:1788-1795) to allow insertion using Gateway technology (Invitrogen) of any desired open reading frame between the promoter and terminator regions of the *T. reesei* cbh1 gene. It also contains the *Aspergillus nidulans* amdS gene for use as a selectable marker in transformation of *T. reesei*.

Figure 17:
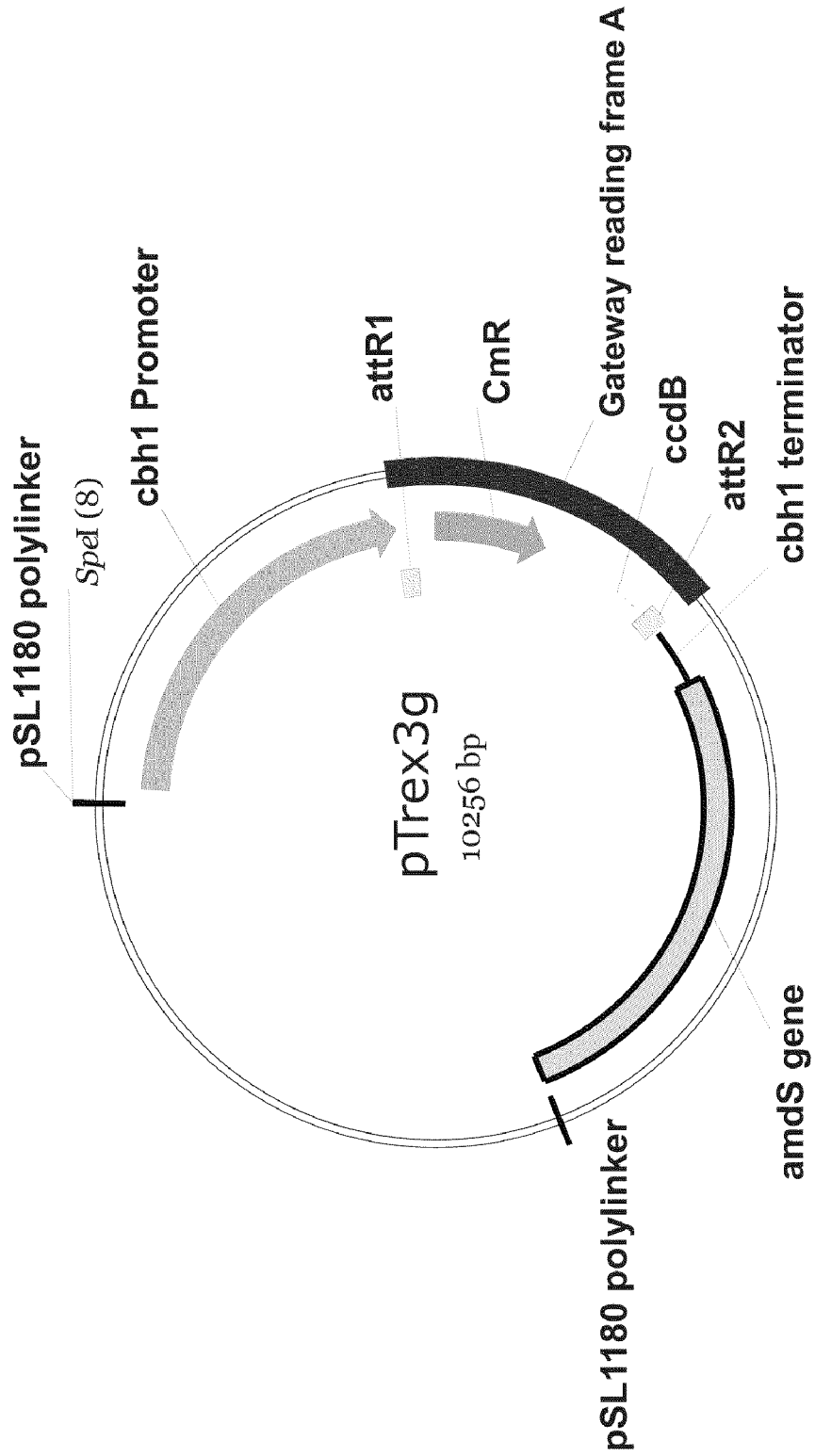
FIG. 17 is schematic of the vector pTrex3g.

The details of pTrex3g are as follows (see FIG. 17). The vector is 10.3 kb in size. Inserted into the polylinker region of pSL1180 are the following segments of DNA:
1. A 2.2 by segment of DNA from the promoter region of the *T. reesei* cbh1 gene
2. The 1.7 kb Gateway reading frame A cassette acquired from Invitrogen that includes the attR1 and attR2 recombination sites at either end flanking the chloramphenicol resistance gene (CmR) and the ccdB gene
3. A 336 by segment of DNA from the terminator region of the *T. reesei* cbh1 gene
4. A 2.7 kb fragment of DNA containing the *Aspergillus nidulans* amdS gene with its native promoter and terminator regions Example 7

Insertion of the cip1 Coding Region into pTrex3g

This example describes the construction of the expression vector for cip1.

The open reading frame of cip1 was amplified by polymerase chain reaction (PCR) using purified genomic DNA from *Trichoderma reesei* strain QM6A (ATCC 13631) as the template. The PCR machine used was a Peltier Thermal Cycler PTC-200 (MJ Research). The DNA polymerase used in PCR was Herculase (Stratagene). The primers used to amplify the cip1 gene were primer 170 (forward) 5'-CACCATGGTTCGCCGGACTGCTCTG-3' (SEQ ID NO:52), and primer 171 (reverse) 5'-TTATAAGCACTGGGAGTAGTATGG-3' (SEQ ID NO:53). The forward primer contained an additional four nucleotides (sequence-CACC) at the 5' end that did not correspond to the cip1 gene but was required for cloning into the pENTR/D-TOPO vector. The PCR conditions for amplifying the cip1 open reading frame were as follows: Step 1: 94 C for 2 min. Step 2: 94 C for 30 sec. Step 3: 58 C for 30 sec. Step 4: 72 C for 35 sec. Steps 2, 3 and 4 were repeated for an additional 21 cycles. Step 5: 72 C for 5 min.

Figure 18:
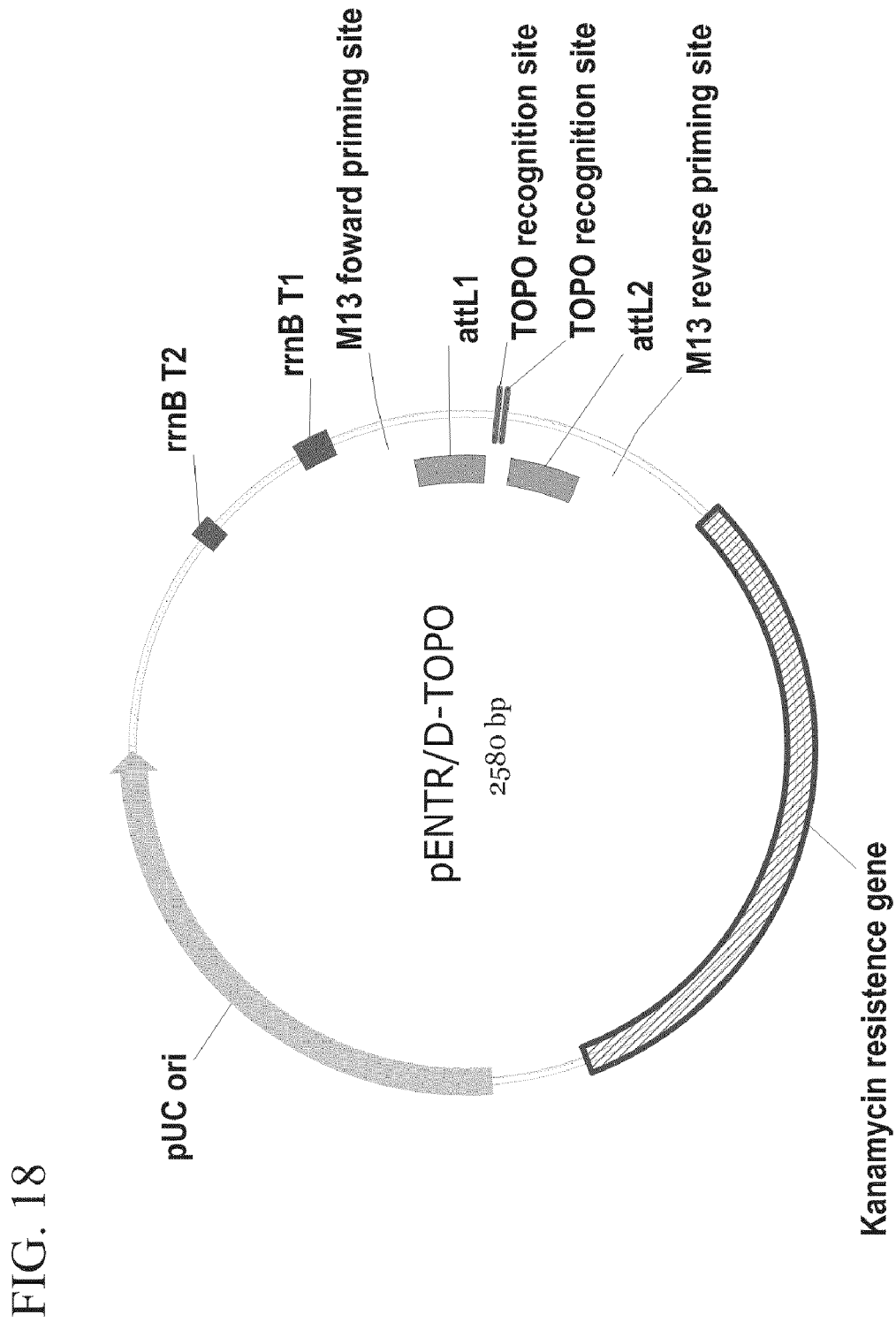
FIG. 18 is schematic of the vector pENTR/D-TOPO (Invitrogen).
Figure 19:
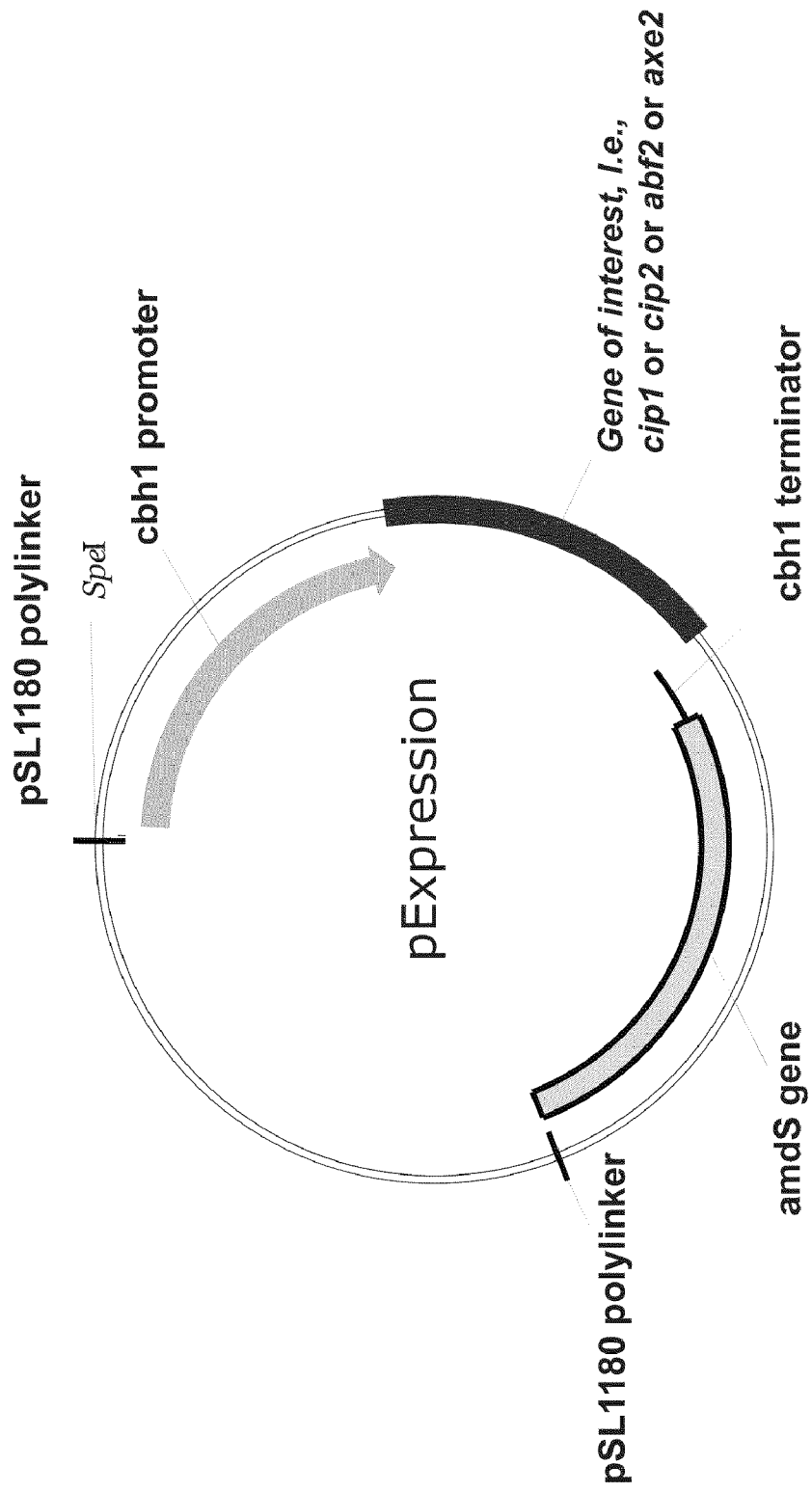
FIG. 19 is schematic of the pExpression construct which will comprise a gene of interest. The gene of interest is selected from cip1 or cip2 or axe2 or abf2.

The PCR product was purified using a Qiaquick PCR Purification Kit (Qiagen). The purified PCR product was initially cloned into the pENTR/D-TOPO vector (Invitrogen, FIG. 18), transformed into TOP10 chemically competent *E. coli* cells (Invitrogen) and plated on LA plates with 50 ppm kanamyacin. Plasmid DNA was obtained from the *E. coli* transformants using a QIAspin plasmid preparation kit (Qiagen). Sequence data was obtained for the inserted DNA in the pENTR/D-TOPO vector using M13 forward and reverse primers. A pENTR/D-TOPO vector with the correct DNA sequence inserted was recombined with the pTrex3g vector using LR clonase (Invitrogen) according to the manufacturers instructions. The product of LR clonase reaction was subsequently transformed into TOP 10 chemically competent *E. coli* cells which were then plated on LA containing 50 ppm carbenicillin. The resulting pExpression construct (FIG. 19) was pTrex3g containing the cip1 gene that resulted from the recombination event between the attR1 and attR2 sites of pTrex3g and the attL1 and attL2 sites of pENTR/D-TOPO. DNA of the pExpression construct containing the cip1 open reading frame was isolated using a Qiagen miniprep kit for biolistic transformation of *Trichoderma reesei* spores.

Example 8

Insertion of the cip2 Coding Region into pTrex3g

This example describes the construction of the expression vector for cip2.

The open reading frame of cip2 was amplified by PCR using purified genomic DNA from *Trichoderma reesei* strain QM6A as the template. The PCR machine used was a Peltier Thermal Cycler PTC-200 (MJ Research). The DNA polymerase used was Herculase (Stratagene). The primers used to amplify cip2 were primer 230 (forward) 5'-CACCATGGCTTCCCGCTTCTTTG-3' (SEQ ID NO:54), and primer 231 (reverse) 5'-TCAACTCAGCGTTGGGGTTG-3' (SEQ ID NO:55). The forward primer contained an additional four nucleotides (sequence-CACC) at the 5' end that did not correspond to the cip2 gene, but was required for cloning into the pENTR/D-TOPO vector. The PCR conditions for amplifying the cip2 open reading frame were as follows: Step 1: 94 C for 2 min. Step 2: 94 C for 30 sec. Step 3: 56 C for 30 sec. Step 4: 72 C for 1 min. 15 sec. Steps 2, 3 and 4 were repeated for an additional 21 cycles. Step 5: 72 C for 5 min.

The PCR product was purified using a Qiaquick PCR Purification Kit (Qiagen). The purified PCR product was initially cloned into the pENTR/D-TOPO vector (Invitrogen, FIG. 18), transformed into TOP10 chemically competent *E. coli* cells (Invitrogen) and plated on LA plates with 50 ppm kanamyacin. Plasmid DNA was obtained from the *E. coli* transformants using a QIAspin plasmid preparation kit (Qiagen). Sequence data was obtained for the inserted DNA in the pENTR/D-TOPO vector using M13 forward and reverse primers. A pENTR/D-TOPO vector with the correct DNA sequence inserted was recombined with the pTrex3g vector using LR clonase (Invitrogen) according to the manufacturers instructions. The product of LR clonase reaction was subsequently transformed into TOP 10 chemically competent *E. coli* cells which were then plated on LA containing 50 ppm carbenicillin. The resulting pExpression construct (FIG. 19) was pTrex3g containing the cip2 gene that resulted from the recombination event between the attR1 and attR2 sites of pTrex3g and the attL1 and attL2 sites of pENTR/D-TOPO. DNA of the pExpression construct containing the cip2 open reading frame was isolated using a Qiagen miniprep kit for biolistic transformation of *Trichoderma reesei* spores.

Example 9

Insertion of the abf2 Coding Region into pTrex3g

This example describes the construction of the expression vector for abf2.

The open reading frame of abf2 was amplified by PCR using purified genomic DNA from *Trichoderma reesei* strain QM6A as the template. The PCR machine used was a Peltier Thermal Cycler PTC-200 (MJ Research). The DNA polymerase used was Pfu Turbo cx Hotstart (Stratagene). The primers used to amplify abf2 were NSP071 (forward): 5"-GGGGACAAGTTTGTACAAAAAAGCAGGC-TATGGAGCTTAAAGCACTCAGTGCCG-3' (SEQ ID NO:56) and NSP072 (reverse): 5"-GGGGACCACTTTGTA-CAAGAAAGCTGGGTTCAGCGCTG-GAGAGTTAGCAGC-3"(SEQ ID NO:57). Both the forward and reverse primers included 29 nucleotides at the 5' end that did not correspond to the abf2 gene, but represent the attB1 site required for cloning into the pDONR201 vector (Invitrogen). The PCR conditions for amplifying the abf2 open reading frame were as follows: Step 1: 95 C for 2 min. Step 2: 95

C for 30 sec. Step 3: 68 C for 30 sec. Step 4: 72 C for 3 min. Steps 2, 3 and 4 were repeated for an additional 29 cycles. Step 5: 72 C for 1 min.

The PCR product was cloned into the pDONR201 vector via the BP clonase reaction using the PCR cloning kit with Gateway® technology (Invitrogen) according to the manufacturers instructions. Sequence data was obtained for the inserted DNA in the pDONR201 vector using M13 forward and reverse primers. A pDONR201 vector with the correct DNA sequence inserted was recombined with the pTrex3g vector using LR clonase (Invitrogen) according to the manufacturers instructions. The product of the LR clonase reaction was subsequently transformed into TOP 10 chemically competent E. coli cells which were then plated on LA containing 50 ppm carbenicillin. The resulting pExpression construct (FIG. 8) was pTrex3g containing the abf2 gene that resulted from the recombination event between the attR1 and attR2 sites of pTrex3g and the attL1 and attL2 sites of pDONR201. DNA of the pExpression construct containing the abf2 open reading frame was isolated using a Qiagen miniprep kit for biolistic transformation of Trichoderma reesei spores.

Example 10

Insertion of the axe2 Coding Region into pTrex3g

This example describes the construction of the expression vector for axe2.

The open reading frame of axe2 was amplified by PCR using purified genomic DNA from Trichoderma reesei strain QM6A as the template. The PCR machine used was a Peltier Thermal Cycler PTC-200 (MJ Research). The DNA polymerase used was Pfu Turbo cx Hotstart (Stratagene). The primers used to amplify axe2 were NSP111 (forward): 5"-GGGGACAAGTTTGTACAAAAAAGCAGGC-TATGCGCGCCCTCTCACTCTCC-3' (SEQ ID NO:58) and NSP112 (reverse): 5"-GGGGACCACTTTGTACAA-GAAAGCTGGGTTCACAGCATCTGAGACACCGCC-3' (SEQ ID NO:59). Both the forward and reverse primers included 29 nucleotides at the 5' end that did not correspond to the axe2 gene, but represent the attB1 site required for cloning into the pDONR201 vector (Invitrogen). The PCR conditions for amplifying the abf2 open reading frame were as follows: Step 1: 95 C for 2 min. Step 2: 95 C for 30 sec. Step 3: 68 C for 30 sec. Step 4: 72 C for 3 min. Steps 2, 3 and 4 were repeated for an additional 29 cycles. Step 5: 72 C for 1 min.

The PCR product was cloned into the pDONR201 vector via the BP clonase reaction using the PCR cloning kit with Gateway® technology (Invitrogen) according to the manufacturers instructions. Sequence data was obtained for the inserted DNA in the pDONR201 vector using M13 forward and reverse primers. A pDONR201 vector with the correct DNA sequence inserted was recombined with the pTrex3g vector using LR clonase (Invitrogen) according to the manufacturers instructions. The product of the LR clonase reaction was subsequently transformed into TOP 10 chemically competent E. coli cells which were then plated on LA containing 50 ppm carbenicillin. The resulting pExpression construct (FIG. 19) was pTrex3g containing the axe2 gene that resulted from the recombination event between the attR1 and attR2 sites of pTrex3g and the attL1 and attL2 sites of pDONR201.

Example 11

Transformation of a Quad Delete T. reesei Strain

This example describes the transformation of a Trichoderma strain with an expression construct. Biolistic transformation of T. reesei with the pTrex3g expression vectors with cip1, cip2 or abf2 open reading frames (pExpression constructs) was performed using the protocol outlined below.

A suspension of spores (approximately $5 \times 10^8$ spores/ml) from a quad deleted strain of T. reesei was prepared. 100 ul-200 ul of spore suspension was spread onto the center of plates of MM acetamide medium. MM acetamide medium had the following composition: 0.6 g/L acetamide; 1.68 g/L CsCl; 20 g/L glucose; 20 g/L $KH_2PO_4$; 0.6 g/L $CaCl_2.2H_2O$; 1 ml/L 1000× trace elements solution; 20 g/L Noble agar; pH 5.5. 1000× trace elements solution contained 5.0 g/l $FeSO_4.7H_2O$, 1.6 g/l $MnSO_4.H_2O$, 1.4 g/l $ZnSO_4.7H_2O$ and 1.0 g/l $CoCl_2.6H_2O$. The spore suspension was allowed to dry on the surface of the MM acetamide medium.

Transformation of T. reesei by the biolistic was performed using a Biolistic® PDS-1000/He Particle Delivery System from Bio-Rad (Hercules, Calif.) following the manufacturers instructions. Briefly, 60 mg of M10 tungsten particles were placed in a microcentrifuge tube. 1 mL of ethanol was added and allowed to stand for 15 minutes. The particles were centrifuged at 15,000 rpm for 15 seconds. The ethanol was removed and the particles were washed three times with sterile dH2O before 1 mL of 50% (v/v) sterile glycerol was added. 25 ul of tungsten particle suspension was placed into a microcentrifuge tube. While continuously vortexing, the following were added; 0.5-5 ul (100-200 ng/ul) of plasmid DNA, 25 ul of 2.5M $CaCl_2$ and 10 ul of 0.1M spermidine. The particles were centrifuged for 3 seconds. The supernatant was removed, the particles were washed with 200 ul of 70% (v/v) ethanol and centrifuged for 3 seconds. The supernatant was removed, the particles were washed with 200 ul of 100% ethanol and centrifuged for 3 seconds. The supernatant was removed and 24 ul 100% ethanol was added, mixed by pipetting, and the tube was placed in an ultrasonic cleaning bath for approximately 15 seconds. While the tube was in the ultrasonic bath, 8 ul aliquots of particles were removed and placed onto the center of macrocarrier disks that were held in a desicator. Once the tungsten/DNA solution had dried the microcarrrier disk was placed in the bombardment chamber along with the plate of MM acetamide with spores and the bombardment process was performed according to the manufacturers instructions. After the bombardment of the plated spores with the tungsten/DNA particles the plates were placed incubated at 28 C. Transformed colonies were picked to fresh plates of MM acetamide after 4 days.

After 5 days of growth on MM acetamide plates transformants displaying stable morphology were inoculated into 250 ml shake flasks containing 30 ml of Proflo medium. Proflo medium contains: 30 g/L α-lactose; 6.5 g/L $(NH_4)_2SO_4$; 2 g/L $KH_2PO_4$; 0.3 g/L $MgSO_4.7H_2O$; 0.2 g/L $CaCl_2$; 1 ml/L 1000× trace element salt solution; 2 ml/L 10% Tween 80; 22.5 g/L Proflo cottonseed flour (Traders Protein, Memphis, Tenn.); 0.72 g/L $CaCO_3$. After two days of growth at 28 C and 140 rpm, 10% of the Proflo culture was transferred to a 250 ml shake flask containing 30 ml of Lactose Defined Media. The composition of Lactose Defined Media was as follows: 5 g/L $(NH_4)_2SO_4$; 33 g/L PIPPS buffer; 9 g/L casamino acids; 4.5 g/L $KH_2PO_4$; 1 g/L $MgSO_4.7H_2O$; 5 ml/L Mazu DF60-P antifoam (Mazur Chemicals, Gurnee, Ill.); 1 ml/L 1000× trace elements solution; pH 5.5. 40 ml/L of 40% (w/v) lactose solution was added to the medium after sterilization. The Lactose Defined medium shake flasks were incubated at 28 C, 140 rpm for 4-5 days. Samples of culture supernatant were mixed with an appropriate volume of 2× sample loading buffer with reducing agent and subjected to sodium dodecyl sulfate-polyacrylamide gel electrophoresis (SDS-PAGE) using precast gels according to the manufacturers instructions (The NuPAGE Bis-Tris Electrophoresis System from Invitrogen Corporation, Carlsbad, Calif. Either NuPAGE 10% Bis-Tris or NuPAGE 4-12% Bis-Tris gels were used with MOPS buffer. NuPAGE LDS sample buffer and NuPAGE reducing agent were used.). The gels were stained for protein with Coomassie Brilliant Blue stain.

Figure 20:
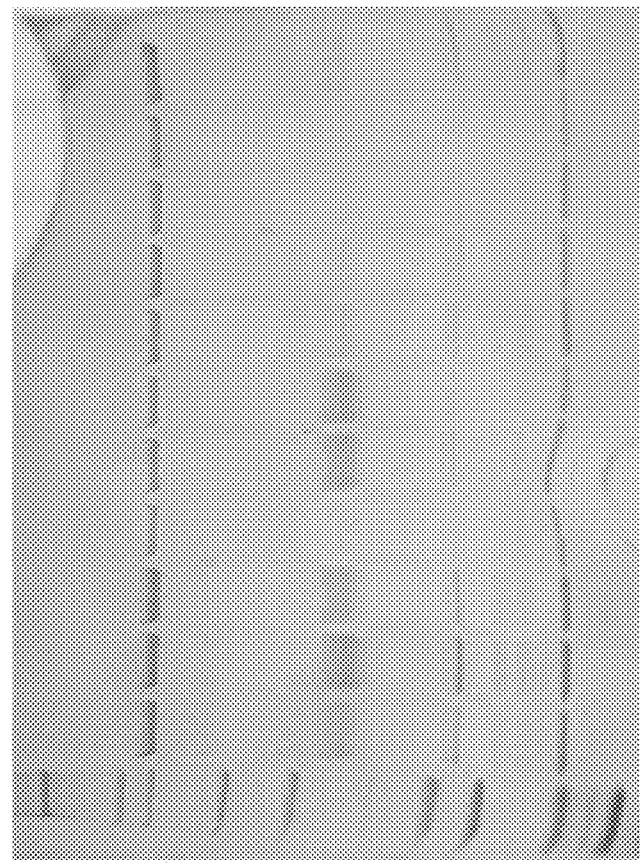
FIG. 20 is a photograph of a SDS-PAGE gel of shake flask supernatant from host cells transformed with an expression vector comprising the cip1 gene. Lane 1 contains the molecular weight markers, Mark 12, from Invitrogen. Lanes 2-12 the supernatant from individual transformant strains. The arrow on the left of the gel designates where on the gel the CIP1 protein would be located if it were expressed and secreted in detectable quantities.

On SDS-PAGE analysis a protein band that was not observed in supernatant from a quad delete strain was observed in the supernatant of some transformants with the pTrex3g vector containing the cip1 open reading frame (FIG. 20). This new protein band had an apparent molecular mass of approximately 50 kDa. This is somewhat higher than the size of 33 kDa predicted from the gene sequence. The discrepency could be accounted for by the post-translational addition of glycosylation. In addition, it is known that some proteins do not migrate according to their size on SDS-PAGE (Saloheimo et al., 1997). This result confirms that Cip1 is a secreted protein.

Figure 21:
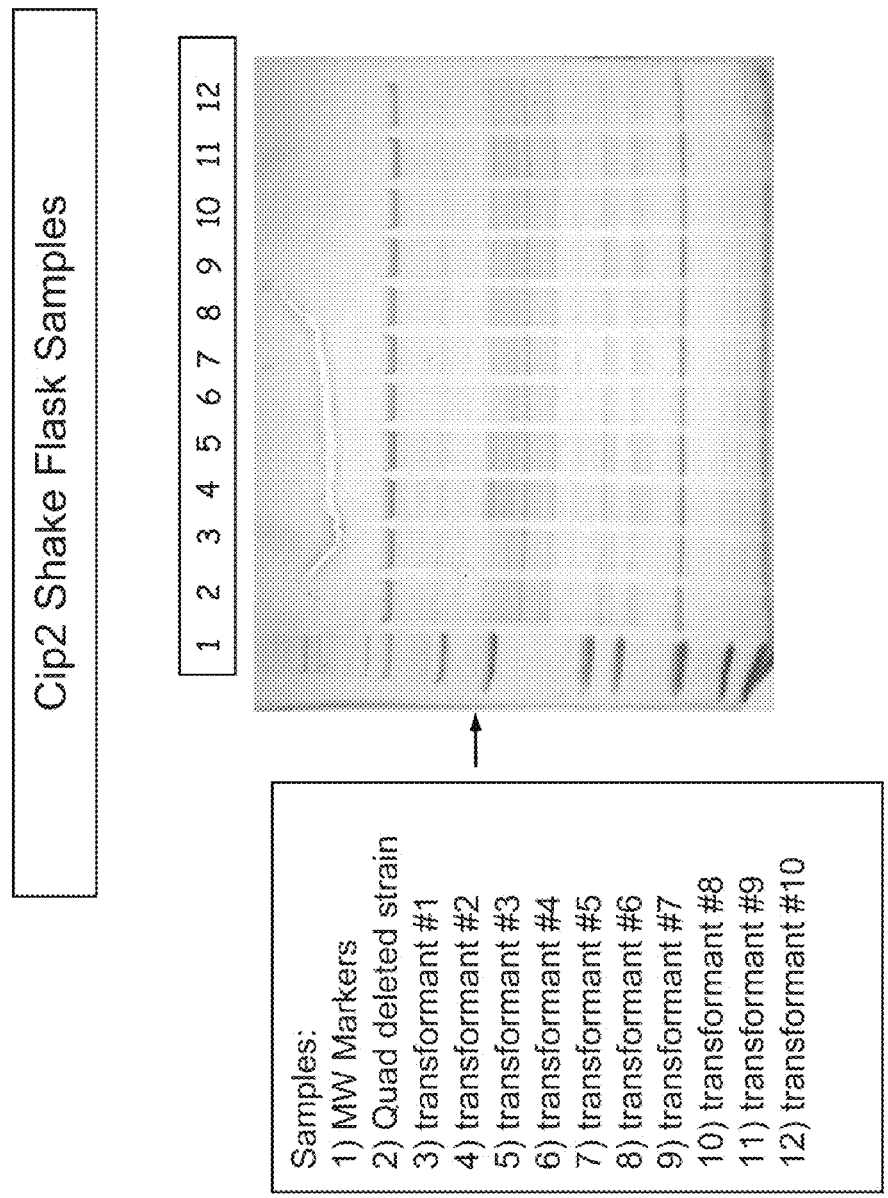
FIG. 21 is a photograph of a SDS-PAGE gel of shake flask supernatant from host cell transformed with an expression vector comprising the cip2 gene. Lane 1 contains the molecular weight markers, Mark 12, from Invitrogen. Lanes 2-12 the supernatant from individual transformant strains. The arrow on the left of the gel designates where on the gel the CIP2 protein would be located if it were expressed and secreted in detectable quantities.

On SDS-PAGE analysis a protein band that was not observed in supernatant from a quad delete strain was observed in the supernatant of some transformants with the pTrex3g vector containing the cip2 open reading frame (FIG. 21). This new protein band had an apparent molecular mass of approximately 56 kDa. This is somewhat higher than the size of 48 kDa predicted from the gene sequence. The discrepency could be accounted for by the post-translational addition of glycosylation. In addition, it is known that some proteins do not migrate according to their size on SDS-PAGE (Saloheimo et al., 1997). This result confirms that Cip2 is a secreted protein.

Figure 22:
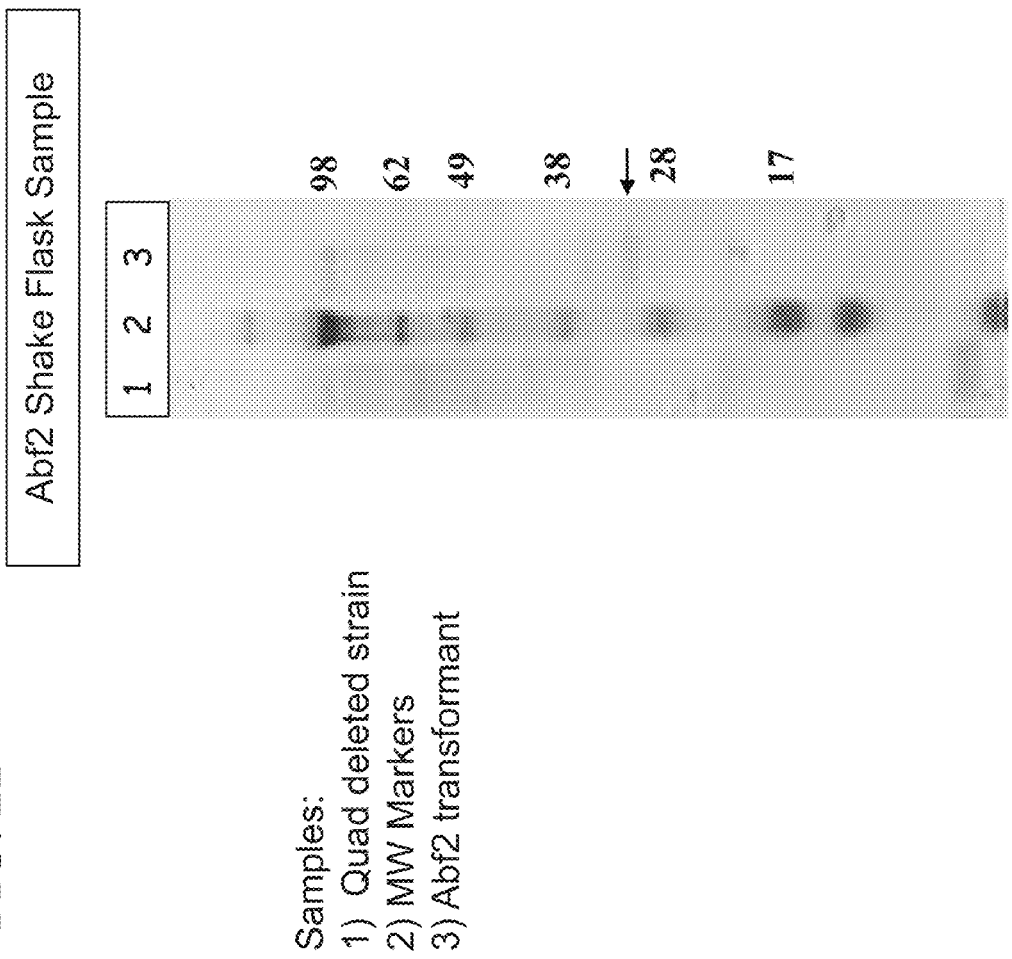
FIG. 22 is a photograph of a SDS-PAGE gel of shake flask supernatant from host cell transformed with an expression vector comprising the abf2 gene. Lane 1 contains the supernatant from the quad delete *Trichoderma* strain described herein. Lane 2 contains the molecular weight markers, Mark 12, from Invitrogen. Lane 3 is contains the supernatant from an individual abf2 transformant. The arrow on the right of the gel designates the band corresponding to where the ABF2 protein would be located if it were expressed.

On SDS-PAGE analysis a protein band that was not observed in supernatant from a quad delete strain was observed in the supernatant of some transformants with the pTrex3g vector containing the abf2 open reading frame (FIG. 22). This new protein band had an apparent molecular mass very close to the 35 kDa predicted from the gene sequence. This result confirms that Abf2 is a secreted protein.

Example 12

Purification of Cip1 Protein and Activity Assays

Cip1 protein was purified from culture supernatant using a BioCAD Sprint (Perseptive Biosystems, Cambridge, Mass.) chromatography workstation by the following protocol. A Poros 20 HP2 10 column was from Perseptive Biosystems (Cambridge, Mass.) hydrophobic interaction chromatography column was equilibrated with 5 column volumes of 0.5M $(NH_4)_2SO_4$/0.02M $NaH_2PO_4$, pH 6.80. The total protein concentration in the supernatant sample was determined using a Bio-Rad (Hercules, Calif.) protein assay kit according to the manufacturers instructions and 20% of the column capacity (20 mg/ml) was applied to the column. The column was washed with 10 column volumes of 0.5M $(NH_4)_2SO_4$/0.02M $NaH_2PO_4$, pH 6.80. Cip1 protein was eluted with 5 column volumes of 0.02M $NaH_2PO_4$, pH 6.80. At this point Cip1 was approximately 70% pure. The eluate was concentrated to 13 ml by ultrafiltration using centrifugal filter units with a nominal molecular weight limit of 5,000 (Biomax 5K; Millipore, Bedford Mass.). A gel filtration column (Superdex 75, Amersham Biosciences) was equilibrated with 2 column volumes of 0.02M $NaH_2PO_4$, pH 6.80 and the concentrated eluate from the previous column was applied. Fractions were collected and analyzed for protein MW by SDS-PAGE and for activity against p-nitrophenyl-6-D-cellobioside (p-NPC). The Cip1 protein was greater than 95% pure at this point.

For p-NPC assays 20 ul p-NPC (7.5 mg/ml) was mixed with 10 ul sample and 100 ul 50 mM sodium acetate, pH 5.0. After incubation at 50° C. for 30 minutes the reaction was stopped by the addition of 100 ul of 100 mM glycine, pH 10. The optical density was measured at a wavelength of 405 nm. Although a specific activity was not determined it was clear that Cip1 had activity against p-NPC. In one experiment the background reaction with no added enzyme gave an OD405 of 0.071 whereas with Cip1 the OD405 was 0.121. This demonstrates that Cip1 protein has some activity on a substrate commonly used to measure activity of cellulases (both endoglucanases and cellobiohydrolases).

Although the foregoing invention has been described in some detail by way of illustration and example for purposes of clarity and understanding, it will be obvious that certain changes and modifications may be practiced within the scope of the appended claims.

Sequence Listing

What is claimed is:

1. An isolated polynucleotide encoding a protein having cellulose binding activity which is:
   (a) a nucleic acid sequence which encodes or is complementary to a sequence which encodes a CIP1 polypeptide having at least 90% sequence identity to the amino acid sequence presented as SEQ ID NO:5;
   (b) a nucleic acid sequence which encodes or is complementary to a sequence which encodes a CIP1 polypeptide having at least 95% sequence identity to the amino acid sequence presented as SEQ ID NO:5;
   (c) a nucleic acid sequence which encodes or is complementary to a sequence which encodes a CIP1 polypeptide having at least 98% sequence identity to the amino acid sequence presented as SEQ ID NO:5;
   (d) a nucleic acid sequence which encodes or is complementary to a sequence which encodes a CIP1 polypeptide having the amino acid sequence presented as SEQ ID NO:5;
   (e) a nucleic acid sequence which encodes or is complementary to a sequence which encodes a CIP1 polypeptide having at least 95% sequence identity to the amino acid sequence presented as SEQ ID NO:3;
   (f) a nucleic acid sequence which encodes or is complementary to a sequence which encodes a CIP1 polypeptide having at least 98% sequence identity to the amino acid sequence presented as SEQ ID NO:3;
   (g) a nucleic acid sequence which encodes or is complementary to a sequence which encodes a CIP1 polypeptide having the amino acid sequence presented as SEQ ID NO:3;
   (h) a nucleic acid sequence presented as SEQ ID NO:2, or the complement thereof, wherein % identity is calculated using the CLUSTAL-W program in MacVector version 6.5, operated with default parameters, including an open gap penalty of 10.0, an extended gap penalty of 0.1, and a BLOSUM 30 similarity matrix; or
   (i) a nucleic acid sequence that hybridizes, under high stringency conditions to the sequence presented as SEQ ID NO:2, or the complement or a fragment thereof, wherein hybridization is conducted at 42° C. in 50% formamide, 6×SSC, 5×Denhardt's solution, 0.5% SDS and 100 µg/ml denatured carrier DNA followed by washing two times in 2×SSPE and 0.5% SDS at room temperature and two additional times in 0.1 SSPE and 0.5% SDS at 42° C.

2. The isolated polynucleotide of claim 1, wherein the enzyme is derived from a *Trichoderma* source.

3. The isolated polynucleotide of claim 2, wherein the enzyme is derived from *Trichoderma reesei*.

4. An expression construct comprising the isolated polynucleotide of claim 1.

5. A vector comprising the expression construct of claim 4.

6. A vector comprising the isolated polynucleotide of claim 1, operably linked to control sequences recognized by a host cell transformed with the vector.

7. A host cell transformed with the vector of claim 5.

8. A host cell transformed with the vector of claim 6.

9. The host cell of claim 7, which is a prokaryotic cell.

10. The host cell of claim 8, which is a eukaryotic cell.

11. A recombinant host cell comprising the isolated polynucleotide of claim 1.

12. The recombinant host cell of claim 11, which is a prokaryotic cell.

13. The isolated polynucleotide of claim 1, wherein said polynucleotide is an RNA.

14. A method of producing an enzyme having cellulose binding activity comprising cultivating the host cell of claim 7 under condition suitable for the host cell to produce the enzyme, and recovering the enzyme.

15. A method of producing an enzyme having cellulose binding activity comprising cultivating the host cell of claim 8 under condition suitable for the host cell to produce the enzyme, and recovering the enzyme.

16. The method of claim 14, wherein the host cell is a filamentous fungi or yeast cell.

17. The method of claim 15, wherein the host cell is a filamentous fungi or yeast cell.

* * * * *